US008278269B2

(12) United States Patent
Martin et al.

(10) Patent No.: US 8,278,269 B2
(45) Date of Patent: *Oct. 2, 2012

(54) CONTROL OF GROWTH AND REPAIR OF GASTRO-INTESTINAL TISSUES BY GASTROKINES AND INHIBITORS

(75) Inventors: Terence Martin, Chicago, IL (US); F. Gary Toback, Chicago, IL (US); Margaret Walsh-Reitz, River Forest, IL (US)

(73) Assignee: The University of Chicago, Chicago, IL (US)

( * ) Notice: Subject to any disclaimer, the term of this patent is extended or adjusted under 35 U.S.C. 154(b) by 934 days.

This patent is subject to a terminal disclaimer.

(21) Appl. No.: 10/473,571

(22) PCT Filed: Mar. 29, 2002

(86) PCT No.: PCT/US02/09885
§ 371 (c)(1),
(2), (4) Date: Jun. 22, 2004

(87) PCT Pub. No.: WO02/078640
PCT Pub. Date: Oct. 10, 2002

(65) Prior Publication Data
US 2005/0054564 A1    Mar. 10, 2005

Related U.S. Application Data

(63) Continuation-in-part of application No. 09/821,726, filed on Mar. 29, 2001, now Pat. No. 6,734,289.

(51) Int. Cl.
*A61K 38/16* (2006.01)
(52) U.S. Cl. ...................................................... 514/7.6
(58) Field of Classification Search ........................ None
See application file for complete search history.

(56) References Cited

U.S. PATENT DOCUMENTS

| 5,102,870 | A  |   | 4/1992  | Florine et al. |         |
|-----------|----|---|---------|----------------|---------|
| 5,644,026 | A  |   | 7/1997  | Yamaguchi et al. |       |
| 6,670,119 | B1 |   | 12/2003 | Yoshikawa et al. |       |
| 6,734,289 | B2 | * | 5/2004  | Martin et al. ......... | 530/399 |
| 6,913,919 | B2 | * | 7/2005  | Botstein et al. ......... | 435/252.3 |
| 7,629,317 | B2 |   | 12/2009 | Toback et al. |          |
| 8,017,576 | B2 |   | 9/2011  | Toback |                 |

FOREIGN PATENT DOCUMENTS

| EP | 0972830 A1 | 1/2000 |
| WO | WO 98/37187 A1 | 8/1998 |
| WO | WO 99/07840 A1 | 2/1999 |
| WO | WO 00/43781 A2 | 7/2000 |
| WO | WO 02/078640 | 10/2002 |

OTHER PUBLICATIONS

Aithal, N.H., et. at (1994) "Glyceraldehyse-3-phosphate Dehydrogenase Modifier Protein is Associated with Microtubules in Kidney Epithelial Cells." *Am. J. Physiol.* 266:F612-619.
Altschul, S.F., et al. (1997) "Gapped BLAST and PSI-BLAST: a New Generation of Protein Database Search Programs." *Nuc. Acids Res.* 25 (17):3389-3402.
Baczako, K et. al.,(1995) "Lectin-Binding Properties of the Antral and Body Surface Mucosa in the Human Stomach—Are Difference Relevant for Helicobacter Pylon Affinity?" *J. Pathol* 176:77-86.
Blaser, M.J. (1987) "Gastric *Campylobacter*-like Organisms, Gastritis, and Peptic Ulcer Disease." *Gastroenterol.* 93:371-383.
Boman, H.G. (1995) "Peptide Antibiotics and Their Role in Innate Immunity." *Ann. Rev. Immunol.* 13:61-92.
Cohen, G.B., et al. (1995) "Modular Binding Domains in Signal Transduction Proteins." *Cell* 80:237-248.
Cregg, J.M., et al. (1993) "Recent Advances in the Expression of Foreign Genes in *Pichia pastoris*." *Bio/Technol.* 11:905-910.
Dignass, A.U., et al. (1998) "Adenine Nucleotides Modulate Epithelial Wound Healing In Vitro." *Eur. J. Clin. Invest.* 28:554-561.
Falk, P., et al. (1993) "An In vitro Adherence Assay Reveals That *Helicobacter pylori* Exhibits Cell Lineage-Specific Tropism in the Human Gastric Epithelium." *Proc. Nat. Acad. Sci. USA* 90:2035-2039.
Goodwin, C.S., et al., (1986) "*Campylocbacter pyloridis*, Gastritis, and Peptic Ulceration." *J. Clin. Pathol.* 39:353-356.
Hasty, P., et al. (1991) "The Length of Homology Required for Gene Targeting in Embryonic Stem Cells." *Mol. Cell. Biol.* 11:5586-5591.
Houston, M.E., et al. (1996) "Lactam Bridge Stabilization of α-Helices: The Role of Hydrophobicity in Controlling Dimeric versus Monomeric α-Helices." *Biochem.* 35:10041-10050.
Janknecht, R., et al. (1991) "Rapid and Efficient Purification of Native Histidine-Tagged Protein Expressed by Recombinant Vaccinia Virus." *Proc. Nat. Acad. Sci. USA* 88:8972-8976.
Jeon, C.J., et al. (1994) "The Transcription Factor TFIIS Zinc Ribbon Dipeptide Asp-Glu is Critical for Stimulation of Elongation and RNA Cleavage by RNA Polymerase II." *Proc. Nat. Acad. Sci. USA* 91:9106-9110.
Johnson, F.R. and McMinn, R.M.H. (1970) "Microscopic Structure of Pyloric Epithelium of the Cat." *J. Anat.* 107:67-86.
Kartha, S. and Toback, F.G. (1985) "Purine Nucleotides Stimulate DNA Synthesis in Kidney Epithelial Cells in Culture." *Am. J. Physiol.* 249:F967-F972.
Lacy, E.R. (1998) "Epithelial Restitution in the Gastrointestinal Tract." *J. Clin. Gastroenterol.* 10(Suppl 1):s72-s77.
Lieske, J.C., et al. (1994) "Renal Epithelial Cells Rapidly Bind and Internalize Calcium Oxalate Monohydrate Crystals." *Proc. Natl. Acad. Sci. USA* 91:6987-6991.s.

(Continued)

*Primary Examiner* — Marianne P Allen
(74) *Attorney, Agent, or Firm* — Barnes & Thornburg LLP; Alice O. Martin

(57) ABSTRACT

A novel group of gastrokines called Gastric Antrum Mucosal Protein is characterized. A member of the group is designated AMP-18. AMP-18 genomic DNA, cDNA and the AMP-18 protein are sequenced for human, mouse and pig. The AMP-18 protein and active peptides derived from it are cellular growth factors. Surprisingly, peptides capable of inhibiting the effects of the complete protein, are also derived from the AMP-18 protein. Cytoprotection and control of mammalian gastro-intestinal tissue growth and repair (restitution) is facilitated by the use of the proteins, making the proteins candidates for therapies in inflammatory bowel disease and gastric ulcers.

6 Claims, 39 Drawing Sheets

OTHER PUBLICATIONS

Lieske, J.C., et al. (1997) "Adhesion of Hydroxyapatite Crystals to Anionic Sites on the Surface of Renal Epithelial Cells." *Am. J. Physiol.* F224-F233.

Mansour, S., et al. (1988) "Disruption of the Proto-Oncogene *int-2* in Mouse Embryo-Derived Stem Cells: A General Strategy for Trageting Mutations to Non-Selectable Genes." *Nature* 336:348-352.

Moore, K.S., et al. (1991) "Antimicrobial Peptides in the Stomach of *Xenpus laevis*." *J. Biol. Chem.* 266 (2a):19851-19857.

Nguyen, J.T., et al. (1998) "Exploiting the Basis of Proline Recognition by SH3 and WW Domains: Design of N-Substituted Inhibitors." *Science* 282:2088-2092.

Nomura, A., et al. (1991) "*Helicobacter pylori* Infection and Gastric Carcinoma Among Japanese Americans in Hawaii." *N. Engl. J. Med.* 325 (16):1132-1136.

Nusrat, A., et al. (1992) "Intestinal Epithelial Restitution." *J. Clin. Invest.* 89:1501-1511.

Park, C.B., et al. (1997) "A Novel Antimicrobial Peptide From the Loach, *Misgurnus anguillicaudatus*." *FEBS Lett.* 411:173-178.

Parsonnet, J., et al. (1991) "*Helicobacter pylori* Infection of the Risk of Gastric Carcinoma." *N. Engl. J. Med.* 325 (16):1127-1131.

Podolsky, D.K. (1997) Healing the Epithelium: Solving the Problem from Two Sides. *J. Gastroenterol.* 32:122-126.

Powell, C.T. (1987) "Characterization of a Novel Messenger RNA and Inummochemical Detection of its Protein from Porcine Gastric Mucosa." *Ph.D. Dissertation*; The University of Chicago.

Quaroni, A., et al. (1979) "Epithelioid Cell Cultures From Rat Small Intestine." *J. Cell Biol.* 80:248-265.

Romanos, M.A. et al. (1992) "Foreign Gene Expression in Yeast: a Review" *Yeast* 8:423-488.

Rotimi, V.O., et al. (1990) "Acidity and Intestinal Bacteria: an In-Vitro Assessment of the Bactericidal Activity of Hydrochloric Acid on Intestinal Pathogens." *Afr. J. Med. med. Sci.* 19:275-280.

Sands, B.E. and Podolsky, D.K. (1996) "The Trefoil Peptide Family." *Ann. Rev. Physiol.* 58:253-273.

Schlessinger, J. and Ullrich, A. (1992) "Growth Factor Signaling by Receptor Tyrosine Kinases." *Neuron* 9:383-391.

Sears, I.B., et al. (1998) "A Versatile Set of Vectors for Constitutive and Regulated Gene Expression in *Pichia pastoris*." *Yeast* 14: 783-790.

Segarini, P.R., et al. (1987) "Membrane Binding Characteristics of Two Forms of Transforming Growth Factor-$\beta$" *J. Biol. Chem.* 262 (30):14655-14662.

Smith, D.B. and Johnson, K.S. (1988) "Single-Step Purification of Polypeptides Expressed in *Escherichia coli* as fusions with Glutathione *S*-transferase." *Gene* 67:31-40.

Toback, F.G. (1980) "Induction of Growth in Kidney Epithelial Cells in Culture by Na$^+$." *Proc. Nat. Acad. Sci.* 77 (11):6654-6656.

Yarden, Y. and Ullrich, A. (1988) "Molecular Analysis of Signal Transduction by Growth Factors." *Biochemistry* 27:3113-3119.

Yoo, O.J. et al. (1982) "Molecular Cloning and Nucleotide Sequence of Full-Length cDNA Coding for Porcine Gastrin." *PNAS* 79:1049-1053.

Yoshikawa, Y., et al. (2000) "Isolation of Two Novel Genes, Down-regulated in Gastric Cancer." *Jap. J. Cancer Res.* 91:459-463.

Database Biosis: Walsh-Reitz et al., "Accumulation of Specific Tight and Adherens Junction Proteins is Stimulated by Antrum Mucosal Protein-18 in Colonic Epithelial Cells in Culture and Mouse In Vivo," Database Accession No. PREV200300571862, Abstract (2003).

Database EMBL (2001): "Human PRO1005 (UNQ489) protein sequence SEQ ID No. 211," Accession No. AAB65209.

Martin et al., "A Novel Mitogenic Protein That is Highly Expressed in Cells of the Gastric Antrum Mucosa," *American Journal of Physiology: Gastrointestinal and Liver Physiology*, 285:2, pp. G332-G343 (2003).

Toback et al., "Peptide Fragments of AMP-18, A Novel Secreted Gastric Antrum Mucosal Protein, Are Mitogenic and Motogenic," *American Journal of Physiology: Gastrointestinal and Liver Physiology*, 285:2, G344-G353 (2003).

Yoshikawa et al., (2000) Isolation of two novel genes, down-regulated in gastric cancer. Japanese Journal of Cancer Research, Japanese Cancer Association, Tokyo, JP, vol. 91, No. 5, 459-463.

Database EMBL (2000), Human signal peptide containing protein, Accession No. AAY87272.

Database EMBL (2001), Accession No. AX055699.

Clackson et al., "A Hot Spot of Binding Energy in a Hormone-Receptor Interface," *Science*, 267, 383-386 (1995).

Database EMBL (2001): "Mus Musculus Adult Male Stomach cDNA, RIKEN Full-Length Enriched Library, Clone: 2210420L15 Product: Weakly Similar to CA11 Protein [*Homo sapiens*], Full Insert Sequence," Accession No. AK008990.

Huang et al., "Transforming Growth Factor Beta Peptide Antagonists and Their Conversion to Partial Agonists," *The Journal of Biological Chemistry*, 272: (43), 27155-27159 (1997).

Kawai et al., "Functional Annotation of a Full-Length Mouse cDNA Collection," *Nature*, 409, 685-690 (2001).

Schmassmann et al., "Roles of Hepatocyte Growth Factor and Its Receptor Met During Gastric Ulcer Healing in Rats," *Gastroenterology*, 113, 1858-1872 (1997).

Tarnawski, "Cellular and Molecular Mechanisms of Ulcer Healing," *Drugs of Today*, 33: (10), 697-706 (1997).

Waltz et al., "Functional Characterization of Domains Contained in Hepatocyte Growth Factor-Like Protein," *The Journal of Biological Chemistry*, 272: (48) 30526-30537 (1997).

Search Report issued in EP 02731209 (2005).

International Search Report issued in PCT/US2006/018014 (2007).

Arseneau et al., "Discovering the cause of inflammatory boewl disease: lessons from animal models," *Current Opinion in Gastroenterology*, 16:310-317 (2000).

Hibi et al., "Animal models of inflammatory bowel disease," *Journal of Gastroenterology*, 37:409-417 (2002).

Israel et al., "Prevention of necrotizing enterocolitis in the rat with prenatal cortisone" (Abstract), *Gastroenterology*, 99(5):1333-8 (1990).

Hsueh et al., "Neonatal necrotizing enterocolitis: Clinical considerations and pathogenetic concepts," *Pediatric and Developmental Pathology*, 6:6-23 (2002).

Shiozaki et al., "Human stomach-specific gene, CA11, is down-regulated in gastric cancer," *International Journal of Oncology*, 4:701-707 (2001).

\* cited by examiner

FIG. 1(1)

```
1    AGCTTTATAA CCATGTGATC CCATCTTATG GTTTCAATCC ATGCACAGGA

51   GGAAAATTGT GGGCACGAAG TTTCCAAAGG GAAAATTTAT AGATTGGTAG

101  TTAATGAAAT ACAGTTTTCC TCCTTGGCAA ATTTAATTTA CTAGCTTCAC

151  TGTATAGGAA AAAGCAGGAA AAAAATTAAA ACCAACTCAC CTCCAAACCT

201  GTTTTGAGCT TTTACTTGTC TGCCCAATTG ATAGTTTCTA CTCTCTGCTT

251  TTGATGAAAA TATTTTTTAT TATTTTAATG TAACTTCTGA AAACTAAATT

301  ATCTAGAAGC AAATAAAAAG ATATTGCTTT TATAGTTCCC AGAAGGAAAA

351  AACAAACACT AGGAAAGTTC TATCTATCAG ATGGGGGAGA TGTGATGGAG

401  GCAGTGATAT TTGAGCTGAG CCTTGAACAA TGAACAGGAG TCTACCAAGC

451  GAGAGGCTAG CGGGTGGCCC TCAAGATAAA ACAACAGCAT GTACAAAGGC

501  ATGGAGACAT ACACATCTTG ACTCTTCCAG GAATGGTGGG AACGCTGGTG

551  GAGCTAGAAT GTAGGTACAT AGCATAAAGT GGCAGACGGG AAGCCTTTGG

601  AAATCTTATT ACATAGGACC CTGGATGCCA TTCCAATGAC TTTGAATTTT

651  CTGTAGGCTG CCAGCGAAAT TTCCAAGCGT GATAGAGTCA TGTCTATCTA

701  TGCACTTCAG AAAGACAACC TCAGGGTTAA TGAAGAAAAT GCATTGGAAT

751  ATAAGAAACT GGTGACCAGA GTGATCAATT GCATGACTGT TGTGAAAGTC

801  CAGGTGAGGG GAGCTGTGGG CAAGGTCAGA GTTGAGAGGC ATTTCAGAGA

851  TAAAATGACA GTAACTAAGT AGATGTCAGG CTGAGAAGAA AGGGCTGTAC

901  CAGATATATG GTGCTATCAT TAAGTGAGCT CAACATTGCA GAAAAGGGGT

951  AGGTTTGGTG GGAGTTGCTC ACAAAACATG TTTAGTCTAA GCAAAACCAT

1001 TGCCATGGGC TCAGATAAAA GTTAAGAAGT GGAAACCATT CCTACATTCC

1051 TATAGGAGCT GCTATCTGGA AGGCCTAGTA TACACGTGGC TTTTCAGCTG

1101 TGATTTTGTT TGATTTTAGG GATTATTCTT TTTCTGAATC TGAGCAATGT
```

1151 TAGCGTGTAA AATACTCACA CCCACAGCTT TGACTGGGTG AGAAGTTATC

1201 ATAAATCATA TTGAGTTTGT TGTGATACCT TCAGCTTCAA CAAGTGATGA

1251 GTCAGGTCAA CTCCATGTGA AAGTTCCTTG CTAAGCATGC AGATATTCTG

1301 AAAGGTTTCC TGGTACACTG GCTCATGGCA CAGATAGGAG AAATTGAGGA

1351 AGGTAAGTCT TTGACCCCAC CTGATAACAC CTAGTTTGAG TCAACCTGGT

1401 TAAGTACAAA TATGAGAAGG CTTCTCATTC AGGTCCATGC TTGCCTACTC

1451 CTCTGTCCAC TGCTTTCGTG AAGACAAGAT GAAGTTCACA GTGAGTAGAT

1501 TTTTCCTTTT GAATTTACCA CCAAATGATT GGAGACTGTC AATATTCTGA

1551 GATTTAGGAG GTTTGCTTCT TATGGCCCCA TCATGGAAAG TTTGTTTTAA

1601 AAAAATTCTC TCTTCAAACA CATGGACACA GAGAGGGGAA CAACACACAC

1651 CAGGTCCTGT TGGGGGGTGG AGAGTGAGGG GAGGGAACTT AGAGGACAGG

1701 TCAATAGGGG CAGCAAACCA CCATGGCACA CATATACCTA TGTAACAAAC

1751 CTGCACGTTC TGCACATGTA TCCCTTTTTT TTAGAAGAAG AAATAATGAA

1801 AAAAAACCTT TTTTCTATTT ATATAATCAT GGCATTTATA AGCATCTCTA

1851 TAGAGAAGGA TAATTGTGCT GAGATTAGAC AGCTGTCTGA GCACCTCACA

1901 CTGACCTATT TTTAACAAAA TGACTTTCCA CATCACCTGA TTTCGGCTCC

1951 ATGCRGGGTA AGCAGTTCCT AAGCCCTAGA AAGTGCCGAT CATCCCTCAT

2001 TCTTGAATTC CTCCTTTTAT TTACCAAAAT TCCTGAGCAT GTTCAGGAAA

2051 GATGAAAAGC TTATTATCAA AATAAGTGGC TGAGATAGAC TTCTTGTCAC

2101 ATTTGTTACA GTAAAATGGG TCTCCAAGAA AGAAAGATTT GCCTTGGGCT

2151 CTAGCATGGC CATTTATTTA AGAAAGCATC TGAAACATGA AGCTACCACA

2201 GCATCTCTCC TGTGGTTCCA GACGGAAGCC TGAGAGTCTA GGAGGAGGTG

2251 GACCGAGAAA CCCTGCCAAA GTAACTAGTA GTGCCGGGTT TCTCACAACA

2301 CGATGCAAAG GGGCTAGAAT CAGATGACTA TTTTCATGTT TCAACATACT

2351 ACACACTGGA AAACGTTACG GCAGACTCTA CTTTATAATG GGGCTGCAAA

2401 TGTAAAATGA CTACTAGAAC TAGGTCCTCT TAATAGCAGC AAAGTTTAAA

2451 AGGGTCAGAG GGAGCTCCAG ACACAGGTTA GATTTGATTT CTCTCCTAGT

2501 TCTGCTGTGA ACAAGAGGTA TAAGTTTGGC CAACTCACTT AACCCCTGAA

2551 GCTCAGTTAC CTTATCTGTA AAATGATTGC ATTGTACTAG GTGTTCTCTA

2601 AAATTTCTTC TACCTCTGAC TTTTTAGGAG ACTAATTTTT AACTCCTTTT

2651 TAAGCTATTG GGAGAAAAAT TTAATTTTTT TTCAAAAGTT ACCTTGAATC

2701 TCTAGAGCAG TTCTCAAAAC TATTTTGTCC CAGGCAAAGG AAATGAGACT

2751 AGGTACCCAG AATGAGGCAC CCTGCATAAA GCTCTGTGCT CTGAAAACCA

2801 ATGTCAGGGA CCCTGTGATA AATAATTAAA CCAAGTATCC TGGGACACTG

2851 CTAGTGACAT CGCCTCTGCT GATCACTCTT GCCAGCGAGA CACTCTATAC

2901 TTGCTTTCTC ATCATTGGCA TCCAAACTGC CTACTAATCC ATTGCTTTGG

2951 AAAGTTTTTT TTAATAAAAA GATTATTTCT ATTAGGAGGA AAACATCCCA

3001 TGTTAAATAG GAAAATTAAC TGAAATCATT TTCAGATGTG ATTTTTAGCA

3051 CTTATAGCCA TTTCAAACCA TGGTATTCAT TTATACTATG CTATTTATTG

3101 TAAAACTTCT TTTTTTTTCC AAGGAAAATA AGATAGTTTG CTTTATTTTA

3151 AAACAGTAAC TTTCTTATAT TGGGGCACTG ACCAAAATTC AATACTGGTA

3201 CAAATATGTT ACCTAGGGGG TCAAAATATG TGCCAGGTGA ATTTTCTGAA

3251 TTTCTCTAAA GAGAGAATTT TAAACCTTAT AAAACAATTA GAAACAAGTG

3301 AGTGAGAGGT GAGCATCAAC AACCTGTGTA ACATAAGCCA CAGTACAAAT

3351 TTAAGCTGAA TAACCAAGCC ATGTCAGTTA TCCCAAATCA TTTTTGTTAA

3401 TATTTAGGAG GATACACATA TTTTCAATAA CTTAAAAGTG AATCTTTACT

3451 CCTATCTCTT AATACTCGAA GAAGTATAAC TTTCTTCTTT TACTAGATTT

3501 AAATAATCCA AATATCTACT CAAGGTAGGA TGCTGTCATT AACTATAGCT

3551 GAGTTTATCC AAAATAGAAA AATCATGAAG ATTTATAAAG CATTTTAAAA

3601 ATAATCATTT ATAGCAAGTC CTTGAAAGCT CTAAATAAGA AAGGCAGTTC

3651 TCTACTTTCT AATAACACCT ATGGTTTATA TTACATAATA TAATTCAACA

3701 AAACAGCATT CTGACCAATG ATAATTTATA GGAAATTCAT TTGCCAAGTA

3751 TATGTTTTAT TATAAAGTTA ATATTTTGAC CAATCTTAAA AATTTTTAAA

3801 CTCTATTCTG ACATTTCCAG AAGTATTATC TTAGCAAGTC ATCTTTATGA

3851 TACCACTTAT TAAACTGAAG AGAAACAAGA TGGTACATTC TGGGTTTTAC

3901 TTTAAAAGGG ATTTGATTCA ATAATTTGAT TTATCACTAC TTGAAAATTA

3951 CATTTTCTTC CTCAGACTGG ATGGCAATGA GATGAAAGCA GCTTTCCTGG

4001 CTCTCAACTT CCCTTCTTCA TCAATTTTTC CAGCGTTTCA TAAGGCCTAC

4051 ACTAAAAATT CTAAAACTAT ATATCACATT AATATAATTA CTTATAATTA

4101 ATCAGCAATT TCACATTATC GTTAAAACCT TTATGGTTAA AAAATGCAAG

4151 GTAAGAGAAG AAAAAAACAC ATTGAACTAG AACTGAACAC ATTGGTAAAA

4201 TTAGTGAATA CTTTTCATAA GCTTGGATAG AGGAAGAAAG AAGACATCAT

4251 TTTGCCATGT AACAGGAGAC CAATGTTATT TGTGATTTCA GATTGTCTTT

4301 GCTGGACTTC TTGGAGTCTT TCTAGCTCCT GCCCTAGCTA ACTATGTAAG

4351 TCTCACCTTT TCAAGTTTGC TACCAAAATG CATTTGCAAG GAAATGTGAT

4401 ATTAAATCAC TCTCAATCTC TTATAAACTT CAGAATATCA ACGTCAATGA

4451 TGACAACAAC AATGCTGGAA GTGGGCAGCA GTCAGTGAGT GTCAACAATG

4501 AACACAATGT GGCCAATGTT GACAATAACA ACGGATGGGA CTCCTGGAAT

4551 TCCATCTGGG ATTATGGAAA TGTAGGTAGT CAACGTGCAA TTTTCACTTT

4601 ATTGTTTAAA AATACGACTT CTTTTTAACA AAAAATGTGC ATGTTAACCA

4651 TAAAGAAATT AAAAATAAAT TCTAATTACA CATAGCATAC AGTTATAAGT

4701 AAAGGTGACC ATTTTGCTCA TCCGATTTTG TTCCCTAGAG ATAACTACTG

4751 TTAATAAGTG TTGCATGATC AGTTAAAATT CAAACCAACA AACACTATGT

4801 TCAAGGGATT GTGGGTATAT ACAACAAATA TGAACATCCT TTTGCCTTGC

4851 CTGCAGATAC CCTCAATAAT GCTGAAAGAC TTATACAACA TTACTGCTTC

4901 CAAAGCTTAG ACTATCTCAC TTTGTTTTCA AAGGAGGTTT TACGACCTTC

4951 TAAAGAGATT GAAATTGACA TTTCACCTAA AACTCGGGAA ATGTAAATGA

5001 CAATATTAAT TGGTAAGAGA GGAAAGAAGA AAGAAAGAAG GAAGGAAAGA

5051 AAGAAAGAAG GAAGGAAGGA AAGAAAGAAA GAAAGAAAGA AAGAGAGAGA

5101 AAGAAAGAAA AAGAAAAAAG AGAGAAAGAG AGAAGGAAAG AAAGAGAGAA

5151 GGAAAGGAAA AGAGAAGCAA AGAAAGAGAG GAGCAAAGAA AGGAACACTT

5201 AGCACTAGTT GGGAGACCCA ACTCTGGAAT TATCAGCTAT ATATTTAACA

5251 AACGTTATAC TTTTAAATAG CAAACTCTTT ATTGTTTCAA TTTTATCTGG

5301 TCAATTGGAA AAATAATTTT TGTCTTATCT GTCTCCTTGA AATGTGAGGA

5351 TCAAAGGAGA CTAAAACATG ATAGCTTTTA AAGTCTATTT CAGTAAAACA

5401 GACTTATATA GAGGGGTTTT TATCATGCTG GAACCTGGAA ATAAAGCAAA

5451 CCAGTTAGAT GCTCAGTCTC TGCCCTCACA GAATTGCAGT CTGTCCCCAC

5501 AAATGTCAGC AATAGATATG ATTGCCAAGC AGTGCCCCAT CCAGTGCTCT

5551 TATCCCAGCT CATCACGATC TTGGAGTTCC CATTTCTCTC TGCAGGTGGA

5601 ACTGACCTCT GATAAGAAAA GCTCCTCGGA GAACACATGC CTCACTATTT

5651 GCCATCTACT TTAACAGGGC TTTGCTGCAA CCAGACTCTT TCAAAAGAAG

5701 ACATGCATTG TGCACAAAAT GAACAAGGAA GTCATGCCCT CCATTCAATC

5751 CCTTGATGCA CTGGTCAAGG AAAAGAAGGT AAAAATAAAA GGCTTTTTAT

5801 TTTTGGTGAG GGGAGAGGTT TTACATCCTT CAGTAAATAA CGAGAAGATC

5851 ACAGTCATTC CCTCTTGACT ACAGTATGTT GTAGTGTGCA GCACAAAGGG

5901 GGAAGTTATT GGTGATTGCC TGAGGGAAGG CAACTTCTGC CACATCAAAT

5951 GCTGTGGCTC ACACCTACCT CTACAACCGC TGAGCAAAGC ACTTGAAACC

6001 TTGACTGTTA GAGGAGCAAA GCTCTGGTCA CACCAATAGG AGCCTCAGTA

6051 CTTTGCCAAG GACATTTTTC TGCAAGAGTT AGTTAGGGTT ATTAGATTTA

6101 GCAAATGAAA ATAGAAGATA TCCAGTTAGG TTTGAATTTT AGGTAAGCAG

6151 CAGGTCTTTT TAGTATAATA TATCCTATGC AATATTTGGG ATATACTAAA

6201 AAAAGATCCA TTGTTATCTG AAATTCAAAT GTAACTGGGT ATTGTATATT

6251 TTGTCTGGCC ATACTAATCC AGGTGAGTGG AAAGAAGAGA TCCATAATGT

6301 TTTAAAATAT TTGCCTGAGT TCATATTCCT ATAACTGATA AATGAGTACC

6351 TTTCATTGAC AAGGTAGAGA AAATAAATAA ACTGCATTCT CAGAAGATGA

6401 TTATTACATA GTCTAATCCA AGGAATCTAT GATGACCAAA TGAGGTCCAA

6451 GTTGCAGAAT AAATTAAGCC TCAGACTTCT GTGTTTATGA GAAGCTGAGG

6501 TTTCAAACCA GGTAAATCCC TTAGGACACT TAGAAATGCT AAGATATACA

6551 GAATAAGCTA GAAATGGCTC TTCTTCATCT TGATTATGGA AAAATTTAGC

6601 TGAGCAACAC TCACTGTTGG CCTCGTATAC CCCTCAAGTC AACAAACCAC

6651 TGGGCTTGGC ATTCATTCTC TCCCATTCTT CCTTTCTACC TCTCTTTTCC

6701 ACACTCAGCT TCAGGGTAAG GGACCAGGAG GACCACCTCC CAAGGGCCTC

6751 ATGTACTCAG TCAACCCAAA CAAAGTCGAT GACCTGAGCA AGTTCGGAAA

6801 AAACATTGCA AACATGTGTC GTGGGATTCC AACATACATG GCTGAGGAGA

6851 TGCAAGGTGA GTAGCATCCC TACTGTGCAC CCCAAGTTAG TGCTGGTGGG

6901 ATTGTCAGAC TATCCTCGCG CGTGTCCATA GTGGGCACCA GTGATGCAGG

6951 GATGGTCATC AAGGCCAACA TTTGTGCAGT GCTTGCTCTG TGCCAGGTAC

7001 TGTTCTATGT GCTTTAAGTG TGTTAACTCG GTTCTTCACA GCAATCTTAT

7051 AGGTTCTATT TTAATCCTAC TTTATGGATG AGGAAACTGA GGTACAGAGA

7101 GGTCACAAAA TCCTTGCCTG GGTCAATTCC AAGCATTTTG GCTGTGGATT

7151 CTGTGCTCTT AAATATTATG GAACACTGCC TTTTAAGTGT GAATCAAGAG

7201 TAGACTCAAG TCATATTCAA AAGAATGCAT GAATGGCTAA ATGAAAGAAG

7251 AATGCTAATA GAATCTATTA ACTTTCTATA GCTCAGACAA TCACTTAATT

7301 TCTGGACATT CAAAGAACAG CTGCACACAA ACAAAGTGTC TACCTAGGGA

7351 CCTAACTTAA TGGCAATTTT CCAGATCTCT GAATTGATTG ATTTCATCAC

7401 AACAAGTAGA TAAACCTTGA CATTAGCACA TAGCTAGTTT GGAAACCCCT

7451 ACTCCCCCAA TCCCCTCCAA GAAAAGAGTC CTTAAATAGA CATTAATATA

7501 GGCTTCTTCT TTTCTCTTTA TTAGAGGCAA GCCTGTTTTT TTACTCAGGA

7551 ACGTGCTACA CGACCAGTGT ACTATGGATT GTGGACATTT CCTTCTGTGG

7601 AGACACGGTG GAGAACTAAA CAATTTTTTA AAGCCACTAT GGATTTAGTC

7651 ATCTGAATAT GCTGTGCAGA AAAAATATGG GCTCCAGTGG TTTTTACCAT

7701 GTCATTCTGA AATTTTTCTC TACTAGTTAT GTTTGATTTC TTTAAGTTTC

7751 AATAAAATCA TTTAGCATTG AATTCAGTGT ATACTCACAT TTCTTACAAT

7801 TTCTTATGAC TTGGAATGCA CAGGATCAAA AATGCAATGT GGTGGTGGCA

7851 AGTTGTTGAA GTGCATTAGA CTCAACTGCT AGCCTATATT CAAGACCTGT

7901 CTCCTGTAAA GAACCCCTTC AGGTGCTTCA GACACCACTA ACCACAACCC

7951 TGGGAATGGT TCCAATACTC TCCTACTCCT CTGTCCACTG CTTAA

FIG.1(7)

```
  1 CATGCTTGCC TACTCCTCTG TCCACTGCTT TCGTGAAGAC AAGATGAAGT
 51 TCACAATTGT CTTTGCTGGA CTTCTTGGAG TCTTTCTAGC TCCTGCCCTA
101 GCTAACTATA ATATCAACGT CAATGATGAC AACAACAATG CTGGAAGTGG
151 GCAGCAGTCA GTGAGTGTCA ACAATGAACA CAATGTGGCC AATGTTGACA
201 ATAACAACGG ATGGGACTCC TGGAATTCCA TCTGGGATTA TGGAAATGGC
251 TTTGCTGCAA CCAGACTCTT TCAAAAGAAG ACATGCATTG TGCACAAAAT
301 GAACAAGGAA GTCATGCCCT CCATTCAATC CCTTGATGCA CTGGTCAAGG
351 AAAAGAAGCT TCAGGGTAAG GGACCAGGAG GACCACCTCC CAAGGGCCTG
401 ATGTACTCAG TCAACCCAAA CAAAGTCGAT GACCTGAGCA AGTTCGGAAA
451 AAACATTGCA AACATGTGTC GTGGGATTCC AACATACATG GCTGAGGAGA
501 TGCAAGAGGC AAGCCTGTTT TTTTACTCAG GAACGTGCTA CACGACCAGT
551 GTACTATGGA TTGTGGACAT TTCCTTCTGT GGAGACACGG TGGAGAACTA
601 AACAATTTTT TAAAGCCACT ATGGATTTAG TCATCTGAAT ATGCTGTGCA
651 GAAAAAATAT GGGCTCCAGT GGTTTTTACC ATGTCATTCT GAAATTTTTC
701 TCTACTAGTT ATGTTTGATT TCTTTAAGTT TCAATAAAAT CATTTAGCAT
751 TG
```

| | | |
|---|---|---|
| 1 | MKFTTVFAGLLGVFLAPALANYNIDVNDDNNNAGSGQQSVSVNNEHNVAN | 50 |
| 51 | VDNNNGWDSWNSIWDYGNGFAATRLFQKKTCIVHKMKKEVMPSIQSLDAL | 100 |
| 101 | VKEKKLQGKGPGGPPPKGLMYSVNPNKVDDLSKFGKNIANMCRGIPTYMA | 150 |
| 151 | EEMQEASLFFYSGTCYTTSVLWIVDISFCGDTVEN | 185 |

FIG.4(1)

```
  1 GAATTCAAAC AGCAGGCCAT CTTTCACCAG CACTATCCGA ATCTAGCCAT
 51 ACCAGCATTC TAGAAGAGAT GCAGGCAGTG AGCTAAGCAT CAGACCCCTG
101 CAGCCCTGTA AGCTCCAGAC CATGGAGAAG AGGAAGGTTG TGGGTTCAAG
151 GAGCTTTTCA GAGTGGAAAT CTGTGGATCA GTGATTTATA AAACACAGTT
201 TCCCCCTTTA TTAGATTTGA ACCACCAGCT TCAGTTGTAG AAGAGAACAG
251 GTTAAAAAAT AATAAGTGTC AGTCAGTTCT CCTTCAAAAC TATTTTAAAC
301 GTTTACTTAT TTTGCCAAGT GACAGTCTCT GCTTCCTCTC CTAGGAGAAG
351 TCTTCCCTTA TTTTAATATA ATATTTGAAA GTTTTCATTA TCTAGAGCAG
401 TGGTTCTCAT CCTGTGGGCC ATGAGCCCTT TGGGGGGGTT GAACGACCCT
451 TTCACAGGGG TCACATATCA GATATCCTGC ATCTTAGCTA TTTACATTAT
501 GATTCATAAC AGTAGCAAAA TTAGTTAGGA AGTAGGAACA AAATAACGTT
551 ATGGTTGTGG TCACCACTAT GTTAGAGGGT CCGCAGCATT CAGAGGGTTG
601 AGAACTGTTG TTCTAGAGGC AAATAAGAAG ACAGAGTTCC TTGATAGGGC
651 CCAGAGGCAG TGAAAGAAGT TTCCACGTAG AAAGTGAAGA AGGTCTGGTG
701 TCCGAAGCAG TGAGGAACTT AAAAAAAGAA AACCAAAAAC ATTGCCAACT
751 AACAGTCCAG GAGAAGAGCG GGGCATGAAA GGCTGAGTTC CCATGGGATG
801 CCTTGAATGG AATCAGAGTG TGGGAAAATT GGTGTGGCTG GAAGGCAGGT
851 GCCGGGCATC TCAGACGCTG GTAGCTGGGG AAACAGGAAA CCCCTTTAGG
901 ATCCCAAGAT GCCATTCCAA TGAGCTTGAG ATTTTTCTCA TGGACTGCCA
951 GTGAATGTTT CTACGCTCCG GAAATTAATG TTTACTTATT TTCCATATTC
1001 TAGGGGAGAA CCCTGGGAAA AATGGAGGAC ATTCATTGAA ATATCTGAGT
1051 CCTGGGATAA GGCAGGCTTG GTCCTACAAC TCTGGTAAAA GTCCATCAGG
1101 AAGTGCCTTG ACCAAGGCTG GAGTGGAGAG CTGTTGGTGA GATGTAAGGG
```

1151 CAAGGTTTAG TTGCTAGATA TGTAGATGGC AAGATGGTGC TGCCAACAGC

1201 CCCCAGAGCT CTAACCCACT GAGAAACCCA GGAATGAATG ATGGGAGATG

1251 GCTTTGGTGC CAGCTGCTAG TGACATGGCT GGAAAGCTGC ACTGGCTTCG

1301 AGGCCAGACA ATTCCTCAAG GAAACATCTG GCCAGGGTGC AAGGGCCAGT

1351 TTCCTTCCTT GGAGTTCCTT TCACAGCTAA GAACATCATC CCCCAACCAC

1401 TGGTTTTGTT AAAAAGTTTT CAGTATGACT TGAGCATGGT CAAGAAGCAT

1451 AGAGAGGGGG AAATAAGGGT GGAAGGAGCT GGAGAAAGCT TACAATAGGA

1501 CTGGGTAAAG GAAGGAGAA GAAACCATTC CCGCATTCCC ATAGGAGCCA

1551 GTACCAGGAA GGGCAGGTGT ACACACAGAT CTCATCTAAG GCCATGTTTG

1601 GTTTAGGGAT TACTCTTCTC CCGAATCTGA GCAGCAGCAA TACGTAAAAT

1651 ACCCACACCC ATGGCTTCCA TATTCCAGAA CTTATCACAA ACCGTGTAGA

1701 GTTTACTGAG ATACCTTCGT CAGAGGATGA GTCAGAGGCC TCCTGCCTAA

1751 GGGCCCTACT GAGCAGGCAG CTAAAGGCTT CCGGGCCTCT GCAGCTCCAC

1801 AGATACAGGA GAGGGAAGCA GATAAGCCGT GGACTCCACC TGAGCACACC

1851 TAGCTTGAGC AAAGCTGGTC AGGTACAAAT AGCAGAGGGC TGAATGTCTG

1901 TGAGCACGCC GCCTGATCCT CTGCTCCACC ACACTCCTGC CGCCATGAAG

1951 CTCACAGTAA GTCAGATCTT CTTTTCAATG CAGCACCATA CAACATTAAT

2001 AGTCAGGGGT GAGGGGGTCT GACTCTTACG GCACTGTTAC CATAGTGGAA

2051 ATATTCTCCT TTCTTTTCAT GGAATCATGG TGTTTACAAG CATGTCCATA

2101 GAGAAGAAGA ATTGCCCCGG AAGAGCCTGT CACAGGCTGA ATACTGTAGA

2151 ATTGTCTTTC ACACCATCTG TTCCAAGGTT CTACTTAAGA CGAGCAGTCT

2201 CTGGGCTCCA GAAAGAGTCT TTCTTAGCCT TGATCTCTTT CTTATTTCTG

2251 ATTTCTCCTT TCTTATCCAT GATTTCCACT TTTACCAGTT CTGGGCA

2301 TCCGGTCAGA CTGGAAGATC ACTGTTGTCA AAACTAGTCT TCAACACTCT

2351 TGGCTGTTAA CATGAAAACA ACGGTCCTTG GGCCCTGTGC AAGCATTTCT

2401 TGGAGAAAGT CTCTGGGGAT GAAGCTATCT CAGTTTCCCC ACTGAAGTCC

2451 TAGGATACAG AGGCTCAAAC AGAGTGCACA TATTCAATTT CAGCATACTC

2501 TATTGGCGCT GCTTTATGAA TCATATGAAT TTATGGAATT GGAAATGTAA

2551 ACTATGACCA AGAAGCGTCC ACCTCAGAAC AGGTTGGGTG GGGAACTCCA

2601 AGCACAGGCC AGAGGGCTGC GTTTCTCTTC TAGTTCTGTC TAGAGGAGTG

2651 GTTCTCGACC TTCCTAATGC TGTGACCCTT TAATACAGTT CCTCACGTTG

2701 TCGTGACTCC CAGCCATAAA ATTACTTTCA TTGCTACTGC ATAACTGTAA

2751 TTTTGCTACC ATTATGAGTT GTAATGTAAA TATCTGATAT GCAAGATACC

2801 AGATAACCTA AGAAACGGTT GTTTGACCTT TAAAGGGGTC ACAACCCACA

2851 GGTGGAGAAC TACTGGTCTA GGGTCCTTTA CAGTCCTTTA GCTGCCTCAT

2901 TTACAGGAGA TAACATCATG CTCAAAAACT CCCTCCACAT TTGGCTTTTT

2951 GGGTTGTTTT GTTTTGTTTT TCAAGACAGG GTTTCTCTGT GTAGCCCTGG

3001 CTGTCCTGGA ACTCACCTTT GTAGACCAGG CTGGCCTCGA ACTCAGAAAT

3051 CCGCCTGCTT CTGCCTCCTG AGCGCTGGGA TTAAAGGCGT GCGCCACCAT

3101 GTCTGGCTCA CATCTGGCTT TTTAAGAGAC CGATTTTAAC TTCTTGCATT

3151 GAAAATAAAT ATAGTAGAAA TGCTTAACCT ACTAAGACAA TAAAAACAGG

3201 ATTCCTTCTG CTAGGAAGAA CACGTTCCAG ACTAAGGAAA AAAACCTTTT

3251 CAGGGCTTTC ATTACACTGT GCCATGCACT AATTTTATGT TTTCTTCATC

3301 AGTTTTCAGT GTCTGAAATT CAGTGTCAAA ATTCTAAGAC TACATATGA

3351 TATCATTACA GTAACTCAGC AATTCTATGT TACCAGTAAG TTTTTCTGTA

3401 GTTTAAAAAA AAGGTGGAAG AAGAAAGCAC AGATAGTTTA GCACATGGGT

3451 AAAATCAGTA ACTATTTCTG ATGAGCTTGG TGAAGATGCT GTAAACCATG

3501 CGACCACCAG TCCTGTTCTC TGTGCTTTCA GATGTTCGTC GTGGGTCTGC

3551 TTGGCCTCCT TGCAGCTCCT GGTTTTGCTT ACGTAAGTCT CATTTTTCTG

3601 AAGTTCATTG TCAAAACTGC ATTTACAGTG AAATGTGATC TTAAGTCACC

3651 CTCTGCTTCT TATGAACATT AGACGGTCAA CATCAATGGT AATGATGGCA

3701 ATGTAGACGG AAGTGGACAG CATTCGGTGA GCATCAATGG TGTGCACAAC

3751 GTGGCCAATA TCGACAACAA TAACGGCTGG GACTCCTGGA ATAGCCTCTG

3801 GGACTATGAA AACGTATGTA ATGGACACAC AGGGTAAAGA TATGGTGTAG

3851 CCACCACCCA TTAAAATTTC TGAGGTGAAT TCTAGCTGTT CATGAACATT

3901 AAAAGCTACC AGTAAAAGTG CCCATTCCAC TCAAAACAAT TTTACTTTTT

3951 TGCATATAAT TATTGCTAAT AAGTATTACA CAATAGGTCG AAATTCAAAG

4001 GGATCAATAG TAAGGATAAA AACTATGTAC AAAGACAAAC ACAGCATCCT

4051 TTGGTCTTCC CTGCAGAGAG TCTCCATGAT GTTAAAGGTC CAATGTTTTA

4101 TGGAGGCTGA ATGAAATACG AATGCCTCTG TGATGGAAAA GGCCCAACAT

4151 CTTATGGAGA ATGAGTGAAG TATGAATGCT ATTAGTTGTA AGAGAAGGCG

4201 ATGCAAAGCA ACACTTGGCA CCACCTGCCA ATTACTACTT TCCTATTTAA

4251 ATGTAGTTTA AAAAGCAAAG CCTGTCTTCC CTGCCTCCTG GAAACACTGC

4301 GGATGGAGGT AGACCAAGGT ATGACAGCCT TTAAAAGTTT GTCAGCAAAA

4351 CACTCCCCCA TACACACATA CACACACCCT CCTACTACAC TGGAACTGAA

4401 GCAAAGGCAG TGGGTTAGAT ATATCCACCC TCTAAGAGTT TGCAGGTCAT

4451 CTATATATGA TAGCCAGAGA CACAACTGCA GGACAGCCAG ACTCTGAGCA

4501 CTCTCCCCAG CTCCTTGTAG CTCTGTTTCA GTGGTGACTT GTGACAAGAA

4551 TCCTGGGGAA CCTGTGCCTC ACTGTTCTCT GTCTTCTTTA ATAGAGTTTC

4601 GCTGCCACGA GACTCTTCTC CAAGAAGTCA TGCATTGTGC ACAGAATGAA

4651 CAAGGATGCC ATGCCCTCCC TTCAGGACCT CGATACAATG GTCAAGGAAC

4701 AGAAGGTAAA GTCCTGCCTT CTTCTTTGGA GTGACAGGAA GTCTTACAGT

4751 CTCCAGTACA CAGTGAAGTC ACCCCCATTC CCTCTTTGGT GGAGCATGAC

4801 AGCATGTTTG TCATGATAAA TGCCACAAAC ATGTAAAACT GTTCAGTGTC

4851 TGCCTGAATG GAGGGTGGCT TCCACTGTGT CAGATGCCGT GGCCCACATC

4901 TGCCTCTGCA GGGTCCAGTA AAGCACTGGC TATCTTGAGT GTCAGAGACC

4951 CAAAGGTCTG TACACTTCAG TACAAGCCCT CCATATTTCA AGGGCACACT

5001 CCTACAGTCG TTGGGGTTAT CAGAACTAGC AAACATAGAG ACTGGATTTT

5051 CAGATGAAAA GAAATCCTTT TTAAAGTCTA AGTATGCCTT ATACAATGTT

5101 TGAGATATTC TCAATACTAA AAAAAAAAAA ATTGTTGCTT GCTTGAAAAT

5151 CAAATGTAAC CAAGTGTCCT ATATCCAGTG TCAATCATGG CTGTAGTAGA

5201 TGGGAAGAGG GAGCCCGTGG TTTTCACAGT CAGACGCCTG AGTTATTCTT

5251 CTAAGTGATA AATTGGTTCC TATAACAAGC AAGCCAGTGA ATATAAATAA

5301 GCTCTATCTC AGAAGTTATC CTGTAGTGCT ACCCTAGAAT CTAAGAGAGC

5351 AAAAGTGCTT CAAATTTCAG AATAAGTTTT GCTTTGGACT TCTGTTTTTC

5401 TAAACAACTA TAACTTCAAA CCATCTAAGC CTCGTGGGAC ACTTAGAAAT

5451 ACCAAGCCAT TCAAAGCTAG AATTGTTTCT TCACCTTACT TGAAAACAAA

5501 ATGACAACCA AAAATTGTCC CCACTGCCCT TGTACATCTT CAGATCAGTA

5551 AAGTCCTGGG CTCAGGGATC ATTCACTTTC TTTCTTTCCT TTCACACTCA

5601 ACTTCAGGGT AAAGGGCCTG GAGGAGCTCC TCCCAAGGAC TTGATGTACT

5651 CCGTCAACCC TACCAGAGTG GAGGACCTGA ATACATTCGG ACCAAAGATT

5701 GCTGGCATGT GCAGGGGCAT CCCTACCTAT GTGGCCGAGG AGATTCCAGG

5751 TGTGTACCCT GAGATGCTGT ATATCCCAAT GCAGTACTGA GAGAGCCATC

5801 AGACACTCTA AAGTGTGACC ACAGACGGAC CAATCATGTG GATTATCAGA

5851 GCAAACACTT GCTTGCTCCT TGTCAGACAG TTGTCCATGC TTCAAAAGTT

5901 CATTAAAAAA AATAGTTCAC AGGCTCCTCA CAGAAACCTT AGTAGAATCC

5951 ACAGCTTCTG CTCTTAGTCT TACTTTTTAG AAACTGAGAC CAGAGAAAG

6001 GTCACAAAAC TTTTGTCTGG CTCAGGTTCT ATGTCTTTAA CTTTATAGAA

6051 TACCGTCTTT CTGGGTGGGT GGGCTCTAGA GTAAACTTCA AGTGAGTTCA

6101 AGGAAAGCAT GAGAAGTAGG GAAGACCAAA TGAAAGGAGA ATGCCAATGA

6151 AATCTATCGA TTCTATAGCG CCAATGCTTA ACTCCTAGGC GTTCAAAGAA

6201 TAGTATCCAC AAGGTGTCAG CCTAAGATCC TAATCTAACA GCAAGTTTTC

6251 AGATCTCTGA AGTGAAAAGA GAAAGCAAGA GAGGAACAGA GACAGAAACA

6301 GTAAGAGACA GAGAGGCAGA GACAAAGAGA CAGGGAGAAT AGAGAGGGAT

6351 TAAAATTAAT ATATAGTTTA GAAATTACGA CTCCTCACAG TCCCTGCAGA

6401 GTCCTAGGAT AGGCACTGAT TTGGACTTCT TTTCTTCTCA CTAGGACCAA

6451 ACCAGCCTTT GTACTCAAAG AAGTGCTACA CAGCTGACAT ACTCTGGATT

6501 CTGCGGATGT CCTTCTGTGG AACATCAGTG GAGACATACT AGAAGTCACA

6551 GGAAAACAAC CCGTGGGCTC TGACCATCGC AATGCTTGAT TATGAGAGTG

6601 TTCTCTGGGG GTTGTGATTA GCTTCTTTAA GGCTCAATAA ACCCACGTGG

6651 CAGCACATCC AGTTTGTAAT GACATGCCTC ATGACTTCTA TGGGAGTCCA

6701 ATGTGGCACC TGCCAGCCTG TATTCAGGAC CTCTCCGCTA TAAAGCATCC

6751 CTCCAGAGTT TTCAAATACT ACAAAGCACA GCCTGGGTTT GGGCTCAGAT

6801 AGGCCACTGC TGCCTGACTA CATTACAGAC AAACAAGTTT TAAAAGAAAG

6851 AAAAAAGAGC TCAGAGTGGC TGGAATCAGC AAGGGTGTTT TTCCTGCAAG

6901 GAGCCAGAAG TATCAATAAT CACCCAAGGA GGAGACACTG GGAATGAGAG

6951 ACTAGAACAC ACGCCTGCAG ATACGGAGAA CCTCAGCATT GCCGCTCTCT

7001 CCCATAACTG CACACCCCCT TCTGTAAACT CTGCTTCTTT CTTTCACCTG

7051 AAGATGGCCC TTGCTTTTTT TTATTATAGG ACANGATAAC TAGACCAGAA

7101 AGTCAACCTG ACTCTCTACA TTTATATGTC TTCCCAGNTC AAGAAATATT

7151 ATTTACTGGT GAATGGCACT TCTATATTCC CTTGGTTCAA TAAGTCTACA

7201 GGATCCATTC ATTGACAGGC AAGAGTGAG ATCACATGAT ACCCAAGCAC

7251 ATGGGTCTTT CCTTGAAGGA GAAGGATCCA

1 ATGTTCGTCGTGGGTCTGCTTGGCCTCCTTGCAGCTCCTGGTTTTGCTTACACGGTCAAC

61 ATCAATGGTAATGATGGCAATGTAGACGGAAGTGGACAGCATTCGGTGAGCATCAATGGT

121 GTGCACAACGTGGCCAATATCGACAACAATAACGGCTGGGACTCCTGGAATAGCCTCTGG

181 GACTATGAAAACAGTTTCGCTGCCACGAGACTCTTCTCCAAGAAGTCATGCATTGTGCAC

241 AGAATGAACAAGGATGCCATGCCCTCCCTTCAGGACCTCGATACAATGGTCAAGGAACAG

301 AAGGGTAAAGGGCCTGGAGGAGCTCCTCCCAAGGACTTGATGTACTCCGTCAACCCTACC

361 AGAGTGGAGGACCTGAATACATTCGGACCAAAGATTGCTGGCATGTGCAGGGGCATCCCT

441 ACCTATGTGGCCGAGGAGATTCCAGGACCAAACCAGCCTTTGTACTCAAAGAAGTGCTAC

501 ACAGCTGACATACTCTGGATTCTGCGGATGTCCTTTTGTGGAACATCAGTGGAGACATAC

561 TAG

FIG.6

1 MKLTMFVVGL LGLLAAPGFA YTVNINGNDG NVDGSGQQSV SINGVHNVAN

51 IDNNNGWDSW NSLWDYENSF AATRLFSKKS CIVHRMNKDA MPSLQDLDTM

101 VKEQKGKGPG GAPPKDLMYS VNPTRVEDLN TFGPKIAGMC RGIPTYVAEE

151 IPGPNQPLYS KKCYTADILW ILRMSFCGTS VETY

FIG.7

```
  1  atgcctgact tctcacttca ttgcattggt gaagccaaga tgaagttcac 51  aattgccttt gctggacttc ttggtgtctt cctgactcct gcccttgctg 101  actatagtat cagtgtcaac gacgacggca acagtggtgg aagtgggcag 151  cagtcagtga gtgtcaacaa tgaacacaac gtggccaacg ttgacaataa 201  caatggatgg aactcctgga atgccctctg ggactataga actggctttg 251  ctgtaaccag actcttcgag aagaagtcat gcattgtgca caaaatgaag 301  aaggaagcca tgccctccct tcaagccctt gatgcgctgg tcaaggaaaa 351  gaagcttcag ggtaagggcc caggggggacc acctcccaag agcctgaggt 401  actcagtcaa ccccaacaga gtcgacaacc tggacaagtt tggaaaatcc 451  atcgttgcca tgtgcaaggg gattccaaca tacatggctg aagagattca 501  aggagcaaac ctgatttcgt actcagaaaa gtgcatcagt gccaatatac 551  tctggattct taacatttcc ttctgtggag gaatagcgga gaactaa
```

FIG.8

1 MKFTIAFAGL LGVFLTPALA DYSISVNDDG NSGGSGQQSV SVNNEHNVAN

51 VDNNNGWNSW NALWDYRTGF AVTRLFEKKS CIVHKMKKEA MPSLQALDAL

101 VKEKKLQGKG PGGPPPKSLR YSVNPNRVDN LDKFGKSIVA MCKGIPTYMA

151 EEIQGANLIS YSEKCISANI LWILNISFCG GIAEN

FIG. 9

| | | | |
|---|---|---|---|
| Human | 1 | MKFTTVFAGLLGVFLAPALANYNIDVNDDNNNAGSGQQSVSVNNEHNVAN | 50 |
| Pig | 1 | MKFTIAFAGLLGVFLTPALADYSISVNDDGNSGGSGQQSVSVNNEHNVAN | 50 |
| | 51 | VDNNNGWDSWNSIWDYGNGFAATRLFQKKTCIVHKMKKEVMPSIQSLDAL | 100 |
| | 51 | VDNNNGWNSWNALWSYRTGFAVTRLFRKKSCIVHKMKKEAMPSLQALDAL | 100 |
| | 101 | VKEKKLQGKGPGGPPPKGLMYSVNPNKVDDLSKFGKNIANMCRGIPTYMA | 150 |
| | 101 | VKEKKLQGKGPGGPPPKSLRYSVNPNRVDNLDKFGKSIVAMCKGIPTYMA | 150 |
| | 151 | EEMQEASLFFYSGTCYTTSVLWIVDISFCGDTVEN | 185 |
| | 151 | EEIQGANLISYSEKCISANILWILNISFCGGIAEN | 185 |

|       | 1          |            |            |            | 50         |
|-------|------------|------------|------------|------------|------------|
| Human | MKFTIVF.AG | LLGVFLAPAL | ANYNIDVN.D | DNNNAGSGQQ | SVSVNNEHNV |
| Pig   | MKFTIAF.AG | LLGVFLTPAL | ADYSISVN.D | DGNSGGSGQQ | SVSVNNEHNV |
| Mouse | MKLTM.FVVG | LLGLLAAPGF | A.YTVNINGN | DGNVDGSGQQ | SVSINGVHNV |

|       | 51         |            |            |            | 50         |
|-------|------------|------------|------------|------------|------------|
| Human | ANVDNNNGWD | SWNSIWDYGN | GFAATRLFQK | KTCIVHKMNK | EVMPSIQSLD |
| Pig   | ANVDNNNGWN | SWNALWDYRT | GFAVTRLFEK | KSCIVHKMKK | EAMPSLQALD |
| Mouse | ANIDNNNGWD | SWNSLWDYEN | SFAATRLFSK | KSCIVHRMNK | DAMPSLQDLD |

|       | 101        |            |            |            | 150        |
|-------|------------|------------|------------|------------|------------|
| Human | ALVKEKKLQG | KGPGGPPPKG | LMYSVNPNKV | DDLSKFGKNI | ANMCRGIPTY |
| Pig   | ALVKEKKLQG | KGPGGPPPKS | LRYSVNPNRV | DNLDKFGKSI | VAMCKGIPTY |
| Mouse | TMVKEQK..G | KGPGGAPPKD | LMYSVNPTRV | EDLNTFGPKI | AGMCRGIPTY |

|       | 151        |            | 188        |
|-------|------------|------------|------------|
| Human | MAEEMQEASL | FFYSGTCYTT | SVLWIVDISF | CGDTVEN    |
| Pig   | MAEEIQGANL | ISYSEKCISA | NILWILNISF | CGGIAEN    |
| Mouse | VAEEIPGPNQ | PLYSKKCYTA | DILWILRMSF | CGTSVETY   |

FIG. 10

```
mrgshhhhhgs    21  NTNIDVNDDNNNAGSGQQSVS
51  VDNNNGWDSWNSIWDYGNGFAATRLFQKKTCIVHKMNKEVM
101 VKEKKLQGKGPGGPPPKGLMYSVNPNKVDDLSKFGKNIANM
151 EEMQEASLFFYSGTCYTHSVIWIVDISFCGDTVEN
```

Predicted Structure for the preAMP-18 ORF

Human

```
HUMAN   1 MKFTIVFAGLLGVFLAPALALANYNIDVADDNNMASGQQSVSVNHEHNVAN   50
          ||||||||| |||||||||||| |  |  |  |||  |||||||||||||||
PIG     1 MKFTIAFAGLLGVFHTPALADYSISVNDDGNSGGSGQQSVSVNHEHNVAN   50

51 VDRHNGWDSWNSTWDYGNGFIXXTRLFQNKFTCIWHKMNREVNPSIQSIDAL  100
            |||||||||||||||||||||| |  |  |  ||   | |  | |  |  |
PIG    51 VDNNNGWNHBRRALWDVXTTGTAWTRLFBEKSCEVHXHKAKANFSLQALDAL 100

101 VRBKKLQSKGPGGEPPKGLAMYSVNPNKVDDESKNGKNLAMCRELPTYKA  150
            |||  | | ||| | |    |  |   |    |  |    |||  | ||
PIG   101 VESKKLQGKGPGGPFFKJLRYSVAPNRVDNLDNFQKSLVANCKEGEPTYKA 150

151 HHMQBASLFFYSGTCHTSVLMXVDISFCGDTVEN*                 186   *=termination
            |  |  |  ||   |      |   || | ||
PIG   151 ERIQGANLISYSEKCIISAWIIWILMISFCGGIAEN*                186
```

FIG. 14

FIG. 27
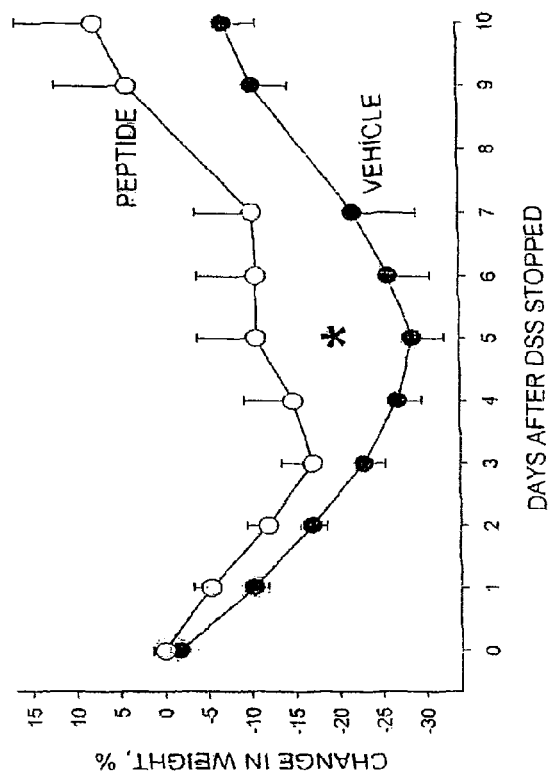
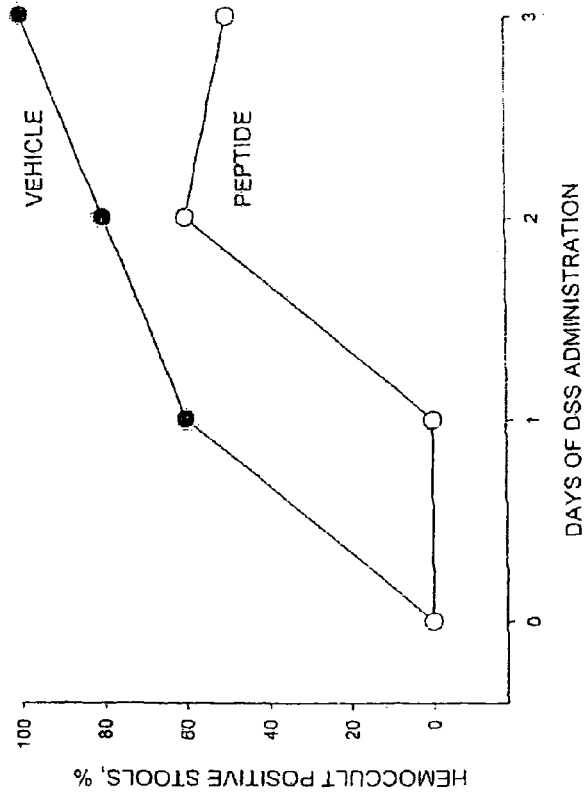

US 8,278,269 B2

CONTROL OF GROWTH AND REPAIR OF GASTRO-INTESTINAL TISSUES BY GASTROKINES AND INHIBITORS

This application is a continuation-in-part of U.S. Ser. No. 09/821,726 filed Mar. 29, 2001 now U.S. Pat. No. 6,734,289 and also claims priority to PCT/US02/09885, filed Mar. 29, 2002.

SEQUENCE LISTING

The instant application contains a Sequence Listing which has been submitted in ASCII format via EFS-Web and is hereby incorporated by reference in its entirety. Said ASCII copy, created on Aug. 29, 2011, is named "94882_Amd_SEQ_ST25.txt" and is 33,490 bytes in size.

BACKGROUND

A novel group of Gastric Antrum Mucosal Proteins that are gastrokines, is characterized. A member of the gastrokine group is designated AMP-18. AMP-18 genomic DNA, and cDNA molecules are sequenced for human and mouse, and the protein sequences are predicted from the nucleotide sequences. The cDNA molecule for pig AMP-18 is sequenced and confirmed by partial sequencing of the natural protein. The AMP-18 protein and active peptides derived from its sequence are cellular growth factors. Surprisingly, peptides capable of inhibiting the effects of the complete protein, are also derived from the AMP-18 protein sequence. Control of mammalian gastro-intestinal tissues growth and repair is facilitated by the use of the protein or peptides, making the protein and the derived peptides candidates for therapies.

Searches for factors affecting the mammalian gastro-intestinal (GI) tract are motivated by need for diagnostic and therapeutic agents. A protein may remain part of the mucin layer, providing mechanical (e.g., lubricant or gel stabilizer) and chemical (e.g. against stomach acid, perhaps helping to maintain the mucus pH gradient and/or hydrophobic barrier) protection for the underlying tissues. The trefoil peptide family has been suggested to have such general cytoprotectant roles (see Sands and Podolsky, 1996). Alternatively, a cytokine-like activity could help restore damaged epithelia. A suggestion that the trefoil peptides may act in concert with other factors to maintain and repair the epithelium, further underlines the complexity of interactions that take place in the gastrointestinal tract (Podolsky, 1997). The maintenance of the integrity of the GI epithelium is essential to the continued well-being of a mammal, and wound closing after damage normally occurs very rapidly (Lacy, 1988), followed by proliferation and differentiation soon thereafter to reestablish epithelial integrity (Nursat et al., 1992). Thus protection and restitution are two critical features of the healthy gastrointestinal tract, and may be important in the relatively harsh extracellular environment of the stomach.

Searches for GI proteins have met with some success. Complementary DNA (cDNA) sequences to messenger RNAs (mRNA) isolated from human and porcine stomach cells were described in the University of Chicago Ph.D. thesis "Characterization of a novel messenger RNA and immunochemical detection of its protein from porcine gastric mucosa," December 1987, by one of the present inventors working with the other inventors. However, there were several cDNA sequencing errors that led to significant amino acid changes from the AMP-18 protein disclosed herein. The protein itself was isolated and purified only as an aspect of the present invention, and functional analyses were performed to determine utility. Nucleic acid sequences were sought.

SUMMARY OF THE INVENTION

A novel gene product designated Antrum Mucosal Protein 18 ("AMP-18") is a gastrokine. The protein was discovered in cells of the stomach antrum mucosa by analysis of cDNA clones obtained from humans, pigs, and mice. The protein is a member of a group of cellular growth factors or cytokines, more specifically gastrokines. The AMP-18 cDNA sequences predict a protein 185 amino acids in length for both pig and man. The nucleotide sequences also predict a 20-amino acid N-terminal signal sequence for secreted proteins. The cleavage of this N-terminal peptide from the precursor (preAMP-18) was confirmed for the pig protein; this cleavage yields a secreted protein 165 amino acids in length and ca. 18,000 Daltons (18 kD) in size. Human and mouse genomic DNA sequences were also obtained and sequenced. A human genomic DNA was isolated in 4 overlapping fragments of sizes 1.6 kb, 3 kb, 3.3 kb and 10.1 kb respectively. The mouse genomic DNA sequence was isolated in a single BAC clone.

The gastrokine designated AMP-18 protein is expressed at high levels in cells of the gastric antrum. The protein is barely detectable in the rest of the stomach or duodenum, and was not found, or was found in low levels, in other body tissues tested. AMP-18 is synthesized in lumenal surface mucosal cells, and is secreted together with mucin granules.

Studies in humans confirm the location and expression of the AMP-18 peptide in human gastric mucosa.

Compositions of AMP-18 isolated from mouse and pig antrum tissue stimulate growth of confluent stomach, intestinal, and kidney epithelial cells in culture; human, monkey, dog and rat cells are also shown to respond. This mitogenic (growth stimulating) effect is inhibited by specific antisera (antibodies) to AMP-18, supporting the conclusion that AMP-18, or its products, e.g. peptides derived from the protein by isolation of segments of the protein or synthesis, is a growth factor. Indeed, certain synthetic peptides whose amino acid sequences represent a central region of the AMP-18 protein also have growth-factor activity. The peptides also speed wound repair in tissue culture assays, indicating a stimulatory effect on cell migration, the process which mediates restitution of stomach mucosal injury. Thus, the protein and its active peptides are motogens. Unexpectedly, peptides derived from sub-domains of the parent molecule can inhibit the mitogenic effect of bioactive synthetic peptides and of the intact, natural protein present in stomach extracts.

There are 3 activities of the gastrokine proteins and peptides of the present invention. The proteins are motogens because they stimulate cells to migrate. They are mitogens because they stimulate cell division. They function as cytoprotective agents because they maintain the integrity of the epithelium (as shown by the protection conferred on electrically resistant epithelial cell layers in tissue culture treated with damaging agents such as oxidants or non-steroidal anti-inflammatory drugs NSAIDs).

The synthesis of AMP-18 is confined to lumenal mucosal lining epithelial cells of the gastric antrum of humans and other mammals. Inside cells the protein is co-localized with mucins in secretion granules, and appears to be secreted into the mucus overlying the apical plasma membrane. Recombinant human AMP-18 in *E. coli* exerts its mitogenic effect at a concentration an order of magnitude lower than growth-promoting peptides derived from the center of the mature protein. Peptide 77-97, the most potent mitogenic peptide, is amino acid sequence-specific AMP peptides appears to be cell-type specific as it does not stimulate growth of fibroblasts or HeLa cells. Mitogenesis by specific AMP peptides appears to be mediated by a cell surface receptor because certain peptides that are not active mitogens can competitively inhibit, in a concentration-dependent manner, the growth-stimulating effects of peptide 58-99 and antrum cell extracts. AMP-18 and its derived peptides exhibit diverse effects on stomach and intestinal epithelial cells which suggest they could play a critical role in repair after gastric mucosal injury. These include cytoprotection, mitogenesis, restitution, and maturation of barrier function after oxidant- and/or indomethacin-mediated injury. Possible mechanisms by which AMP-18 or its peptide derivatives mediate their pleiotropic effects include stimulation of protein tyrosine kinase activity, prolongation of heat shock protein expression after cell stress, and enhanced accumulation of the tight junction-associated protein ZO-1 and occludin. Certain of these physiological effects can occur at concentrations that are relatively low for rhAMP-18 (<50 nM) compared to the concentrations of other gastric peptide mediators such as trefoil peptides or the α-defensin, cryptdin 3 (>100 µM). Immunoreactive AMP-18 is apparently released by cells of the mouse antrum after indomethacin gavage, and by canine antrum cells in primary culture exposed to forskolin, suggest that the protein is subject to regulation. These results imply that AMP-18 could play a role in physiological and pathological processes such as wound healing in the gastric mucosal epithelium in vivo.

The invention relates a group of isolated homologous cellular growth stimulating proteins designated gastrokines, that are produced by gastric epithelial cells and include the consensus amino acid sequences VKE(K/Q)KXXGKGPGG(P/A)PPK (SEQ ID NO: 10) wherein XX can be LQ or absent (which results in SEQ ID NOS 25 and 26, respectively). An isolated protein of the group has an amino acid sequence as shown in FIG. 7. The protein present in pig gastric epithelia in a processed form lacking the 20 amino acids which constitute a signal peptide sequence, has 165 amino acids and an estimated molecular weight of approximately 18 kD as measured by polyacrylamide gel electophoresis. Signal peptides are cleaved after passage through endoplasmic reticulum (ER). The protein is capable of being secreted. The amino acid sequence shown in FIG. 3 was deduced from a human cDNA sequence. An embodiment of the protein is shown with an amino acid sequence as in FIG. 6, a sequence predicted from mouse RNA and DNA.

A growth stimulating (bioactive) peptide may be derived from a protein of the gastrokine group. Bioactive peptides rather than proteins are preferred for use because they are smaller, consequently the cost of synthesizing them is lower than for an entire protein.

In addition, a modified peptide may be produced by the following method:
(a) eliminating major protease sites in an unmodified peptide amino acid sequence by amino acid substitution or deletion; and/or
(b) introducing into the modified amino acid analogs of amino acids in the unmodified peptide.

An aspect of the invention is a synthetic growth stimulating peptide, having a sequence of amino acids from positions 78 to 119 as shown in FIG. 3.

Another peptide has a sequence of amino acids from position 97 to position 117 as shown in FIG. 3.

Another peptide has a sequence of amino acids from position 97 to position 121 as shown in FIG. 3.

Another peptide has a sequence of amino acids from position 104 to position 117 as shown in FIG. 3.

An embodiment of an isolated bioactive peptide has one of the following sequences: KKLQGKGPGGPPPK (SEQ ID NO: 11), LDALVKEKKLQGKGPGGPPPK (SEQ ID NO: 12), or LDALVKEKKLQGKGPGGPPPKGLMY (SEQ ID NO: 13). An embodiment of an inhibitor of a protein of the gastrokine group has the amino acid sequence KKTCIVHK-MKK (SEQ ID NO: 14) or KKEVMPSIQSLDALVKEKK. (SEQ ID NO: 15) (see also Table 1)

The invention also relates a pharmaceutical composition including at least a growth stimulating peptide.

A pharmaceutical composition for the treatment of diseases associated with overgrowth of gastric epithelia, includes an inhibitor of a protein of the group of gastrokines or of a growth stimulating peptide derived from the gastrokine proteins.

A pharmaceutical composition for the treatment of diseases of the colon and small intestine includes at least a growth stimulating peptide of the present invention. Examples of such diseases include ulcerative colitis and Crohn's Disease.

Antibodies to the protein product AMP-18 encoded by the human cDNA expressed in bacteria were produced in rabbits; these antibodies reacted with 18 kD antrum antigens of all mammalian species tested (human, pig, goat, sheep, rat and mouse), providing a useful method to detect gastrokines. An antibody to a protein of the group recognizes an epitope within a peptide of the protein that includes an amino acid sequence from position 78 to position 119 as in FIG. 3.

The invention is also directed to an isolated genomic DNA molecule with the nucleotide sequence of a human as shown in FIG. 1 and an isolated cDNA molecule encoding a human protein, that the nucleotide sequence as shown in FIG. 2.

Another aspect of the invention is an isolated DNA molecule having the genomic sequence found in DNA derived from a mouse, as shown in FIG. 4.

Genomic DNA has value because it includes regulatory elements for gastric expression of genes, consequently, the regulatory elements can be isolated and used to express other gene sequences than gastrokines in gastric tissue.

An aspect of the invention is a mouse with a targeted deletion in a nucleotide sequence in the mouse genome that, when expressed without the deletion, encodes a protein of the group of gastrokines of the present invention.

An aspect of the invention is a method of making a gastrokine protein or a peptide derived from a gastrokine protein. The method includes:
a) obtaining an isolated cDNA molecule with a sequence such as that shown in FIG. 2;
(b) placing the molecule in a recombinant DNA expression vector;
(c) transfecting a host cell with the recombinant DNA expression vector;
(d) providing environmental conditions allowing the transfected host cell to produce a protein encoded by the cDNA molecule; and
(e) purifying the protein from the host cell.

Host cells in which expression has been successful include baculovirus, which allows large amounts of gastrokines to be provided for commercial and research uses. For example, human AMP-18 protein without the signal peptide was produced.

A recombinant human protein AMP-18 expressed in *E. coli* has the sequence in FIG. 14, left panel.

An aspect of the invention is a method to stimulate growth of epithelial cells in the gastrointestinal tract of mammals. The method includes the steps of:
 (a) contacting the epithelial cells with a composition comprising a gastrokine protein or a peptide derived from a protein of the group; and
 (b) providing environmental conditions for stimulating growth of the epithelial cells.

A method to inhibit cellular growth stimulating activity of a protein of the group includes the steps of:
 (a) contacting the protein with an inhibitor; and
 (b) providing environmental conditions suitable for cellular growth stimulating activity of the protein.

The inhibitor may be an antibody directed toward at least one epitope of the protein, e.g. an epitope with an amino acid sequence from position 78 to position 119 of the deduced amino acid sequence in FIG. 3 or an inhibitor peptide such as those in Table 1.

A method of testing the effects of different levels of expression of a protein on mammalian gastrointestinal tract epithelia, includes the steps of:
 (a) obtaining a mouse with an inactive or absent gastrokine protein;
 (b) determining the effects of a lack of the protein in the mouse;
 (c) administering increasing levels of the protein to the mouse; and
 (d) correlating changes in the gastrointestinal tract epithelia with the levels of the protein in the epithelia.

Kits are contemplated that will use antibodies to gastrokines to measure their levels by quantitative immunology. Levels may be correlated with disease states and treatment effects.

A method to stimulate migration of epithelial cells after injury to the gastrointestinal tract of mammals, includes the steps of:
 (a) contacting the epithelial cells with a composition comprising a peptide derived from the protein; and
 (b) providing environmental conditions allowing migration of the epithelial cells.

A method for cytoprotection of damaged epithelial cells in the gastrointestinal tract of mammals, includes the following steps:
 (a) contacting the damaged epithelial cells with a composition including a protein of the gastrokine group or a peptide derived from the protein; and
 (b) providing environmental conditions allowing repair of the epithelial cells.

The damaged cells may form an ulcer.

BRIEF DESCRIPTION OF THE DRAWINGS

FIG. 1(1)-1(7) is a human genomic nucleotide sequence (SEQ ID NO: 1) of a pre-gastrokine; sequence features were determined from cDNA and PCR of human genomic DNA amph-ge8.seq Length: 7995 predicted promoter: 1405; exon 1: 1436-1490; exon 2: 4292-4345; exon 3: 4434-4571; exon 4: 5668-5778; exon 5: 6709-6856; exon 6: 7525-7770; polyA site: 7751.

FIG. 2 is a human cDNA sequence (SEQ ID NO: 2); the DNA clone was obtained by differential expression cloning from human gastric cDNA libraries.

FIG. 3 is a human preAMP-18 protein sequence (SEQ ID NO: 3) predicted from a cDNA clone based on Powell (1987) and revised by the present inventors; N-21 is the expected N-terminus of the mature protein.

FIG. 4(1)-4(7) is a mouse preAMP-18 sequence (SEQ ID NO: 4) determined from RT-PCR of mRNA and PCR of BAC-clones of mouse genomic DNA sequences:
 predicted promoter: 1874 experimental transcription start site: 1906 translation initiation site: 1945 CDS 1: 1906-1956; CDS 2: 3532-3582; CDS 3: 3673-3813; CDS 4: 4595-4705; CDS 5: 5608-5749; CDS 6: 6445-6542; polyA site: 6636.

FIG. 5 is a mouse cDNA sequence (SEQ ID NO: 5) for preAMP-18.

FIG. 6 is mouse preAMP-18 amino acid sequence (SEQ ID NO: 6); RT-PCR performed on RNA isolated from mouse stomach antrum: Y-21 is the predicted N-terminus of the mature protein; the spaces indicated by mean there are no nucleotides there to align with other sequences in FIG. 11.

FIG. 7 is a cDNA expressing porcine AMP-18 (SEQ ID NO: 7).

FIG. 8 is pig pre-gastrokine (pre-AMP-18) protein sequence (SEQ ID NO: 8) predicted from a cDNA clone based on Powell (1987) D-21 is the N-terminus of the mature protein—confirmed by sequencing of the protein isolated from pig stomach.

FIG. 9 is a comparison between the amino acid sequences of human (SEQ ID NO: 3) versus pig (SEQ ID NO: 8) pre-gastrokine.

FIG. 10 shows a computer-generated alignment comparison of human (SEQ ID NO: 3), pig (SEQ ID NO: 8) and mouse (SEQ ID NO: 6) predicted protein sequences determined from sequencing of cDNA clones for human and pig AMP-18, and by polymerase chain reaction of mouse RNA and DNA using preAMP-18 specific oligonucleotide primers; in each case the first 20 amino acids constitute the signal peptide, cleaved after passage through the endoplasmic reticulum membrane.

FIG. 14 shows Left Panel. Alignment of the open reading frames (ORF) derived from the cDNA clones for AMP-18 for the precursor proteins of human (SEQ ID NO: 3) and pig (SEQ ID NO: 8) antrum. Similarity was 78.50% and identity was 75.27%. Computer analysis was carried out using the GAP and PEPTIDESTRUCTRE programs of the Wisconsin Package (GCG). Right Panel. Model of the predicted secondary structure for the human preAMP ORF. Attention is drawn to the asparagine rich N-terminal domain, the short tryptohopan (W)-rich and glycine-proline (GP) regions, and the conserved positions of the four cysteine (C) residues. Possible amphipathic helices are indicated.

FIG. 27 shows Left Panel. Mice (n=10) were given 3% DSS, and stools were assayed daily. Fewer animals given AMP peptide (3 mg/kg body weight/day, s.c.) than vehicle and homocult-positive stool. Right panel. After animals received DSS for 4 days, they were switched to water (day 0 on graph). Mice given AMP peptide daily lost less weight than those given vehicle by day 5 (P<0.04). Weight of peptide-treated animals on days 4 and 5 appeared to increase; it declined in those given vehicle.

DETAILED DESCRIPTION OF THE INVENTION

1. General

Figure 11:
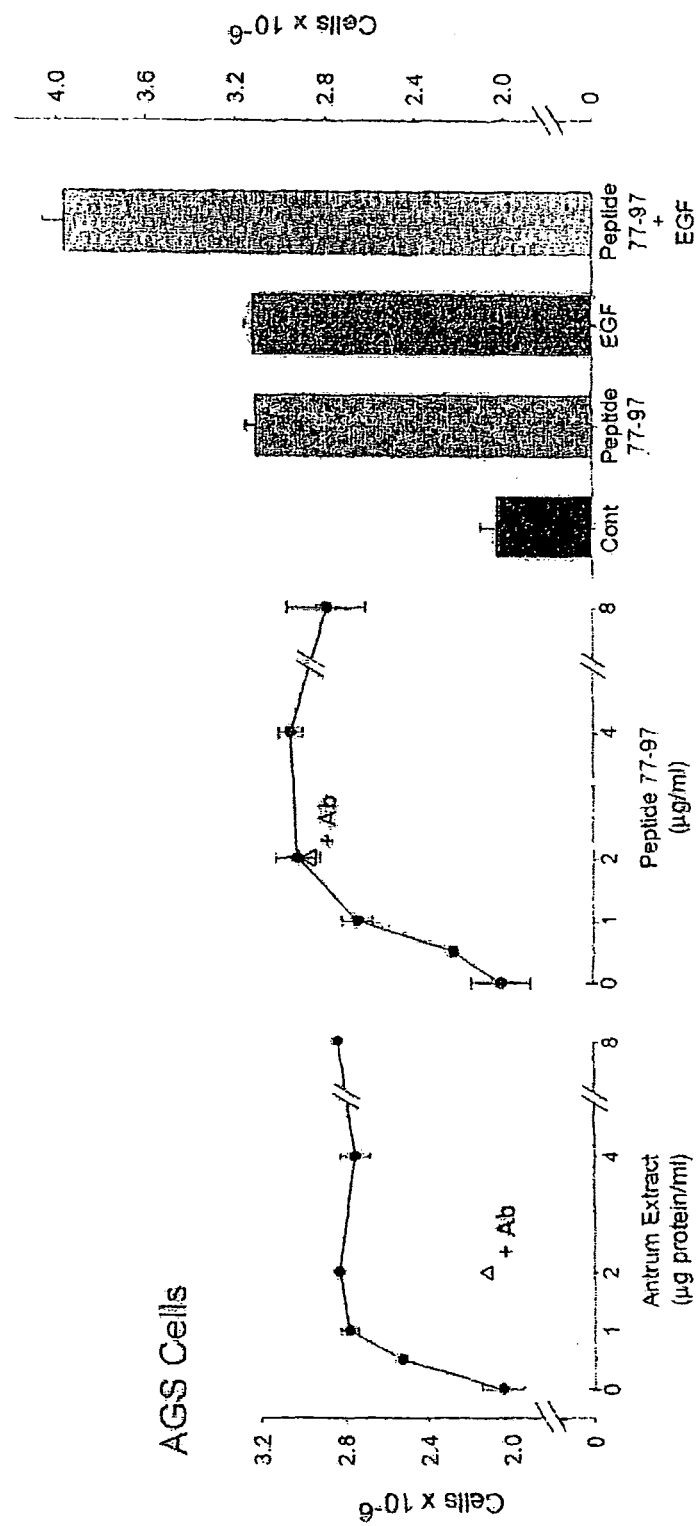
FIG. 11 shows the effect of porcine gastric antrum mucosal extract, human AMP peptide 77-97, of the mature protein (same as peptide 97-117 of human precursor protein: Table 1) and EGF on growth of gastric epithelial cells; AGS cells were grown in DMEM containing fetal bovine serum (5%) in 60-mm dishes; different amounts of pig antrum extract, HPLC purified peptide 77-97, and/or EGF were added; four days later the cells were dispersed and counted with a hemocytometer; antrum extract and peptides each stimulated cell growth in a concentration-dependent manner; the bar graph shows that at saturating doses, peptide 77-97 (8 µg/ml) or EGF (50 ng/ml) was mitogenic; together they were additive suggesting that the two mitogens act using different receptors and/or signaling pathways; anti-AMP antibodies inhibited the antrum extract but did not inhibit peptide 77-97.
Figure 12:
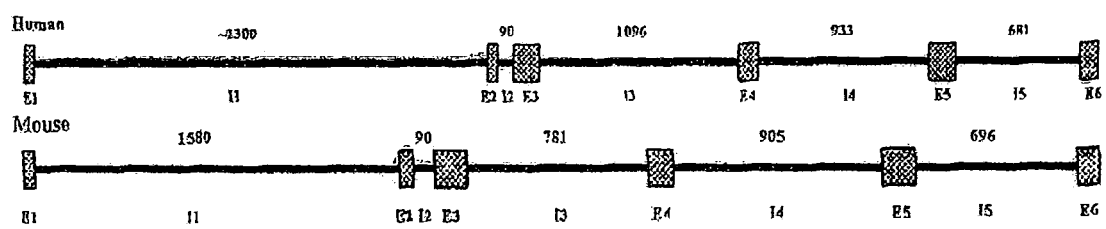
FIG. 12 shows the structure of the human and mouse preAMP-18 genes; the number of base pairs in introns are shown above the bars; exons are indicated E1-E6 and introns 11-15; there are minor differences in intron length.

A novel gene product, a member of a group of gastrokines, was detected in mammalian gastric antrum mucosal by a differential screen of cDNA libraries obtained from different regions of the pig stomach. The cDNA sequence predicted a protein of 185 amino acids including a signal peptide leader sequence. A cDNA was also isolated from a human library. The predicted amino acid sequence identity between pig and human in 76.3%. The sequences predicted a 20 amino acid signal peptide characteristic for secreted proteins. The cleavage of this N-terminal signal peptide was confirmed for the pig protein. Antibodies to the product of the human cDNA expressed in bacteria were raised in rabbits; these antibodies reacted with 18-20 kD antrum antigens of all mammalian species tested (pig, goat, sheep, rat and mouse). In agreement with mRNA levels, the AMP-18 protein is expressed at high levels only in the gastric antrum; it is barely detectable in the rest of the stomach or duodenum, and was not detected in a variety of other tissues tested. AMP-18 is synthesized in the lumenal surface mucosal cells; immuno-electron microscopy locates AMP-18 in the secretion granules of these cells. Partially purified AMP-18 preparations from mouse and pig antrum tissue are mitogenic to confluent stomach and kidney epithelial cells in culture; this effect is inhibited by the specific antisera, implying that AMP-18, or its products, is a growth factor.

AMP-18 is likely secreted with the mucus and functions, perhaps as peptide derivatives, within the mucus gel to maintain epithelial integrity directly, and possibly to act against pathogens. In view of the growth factor activity observed on epithelial cell lines in culture, it is likely that AMP-18 or its peptide derivative(s) serves as an autocrine (and possible paracrine) factor for the gastric epithelium. The function of AMP-18 may not be simply as a mitogen, but in addition it may act as differentiation factor providing the signals for replenishment of the mature lumenal surface cells. The AMP-18 protein or its derivatives are likely important to the normal maintenance of the highly dynamic gastric mucosa, as well as playing a critical role in the restitution of the antrum epithelium following damage. This protein has not been characterized in any publication, however, related nucleic acid sequences have been reported as ESTs and as a similar full length gene. Limitations of EST data cannot yield information on starting sequences, signal peptides, or sequences in the protein responsible for bioactivity, as disclosed in the present invention. A number of these ESTs have been reported for mammalian stomach cDNAs, but related ESTs have also been reported or pancreas and also pregnant uterus libraries. Although expression of AMP-18 RNA in these other tissues appears to be low (as indicated for pancreas by PCR analysis), these results suggest that this growth factor may have broader developmental and physiological roles than that implied by the specific high levels of expression found for the stomach.

The AMP-18 protein appears to be expressed at the surface of the cellular layers of the gastrointestinal (GI) tract. The expressing cells may be releasing stored growth factor where needed-in the crypts and crevices of the GI tract where cellular repair is needed due to surface damage.

AMP-18 may act on the mucosal, apical surfaces of the epithelial cells, collaborating with prostaglandins and other growth factors that operate via basolateral cell surface receptors on the serosal side. The protein or its derivatives are likely important for the normal maintenance of the highly dynamic gastric mucosa, in face of the mechanical stress and high acidity of the stomach. AMP-18 may play a critical role in the repair of the stomach epithelium following damage by agents such as alcohol, nonsteroidal anti-inflammatory drugs (NSAIDs), or pathogens, in particular *Heliobacter pylori*, which predominantly infects the antrum and is a causative agent of gastric ulcers and possibly cancers.

2. Bioactivity

A synthetic peptide (42 amino acids, a "42-mer") representing a central region of the AMP-18 amino acid sequence also has growth factor activity, which is inhibited by specific antisera; some related shorter peptides also have stimulatory activity, while others can inhibit the activity of the 42-mer. This result suggests that a saturatable epithelial receptor exists for AMP-18, and opens direct avenues to analyzing the bioactive regions of the protein and identifying the putative receptor(s). Because AMP-18 does not resemble in structure any known cytokine or cytoprotectant protein (such as the trefoil peptides), the analysis of the interactions of the protein, and its active and inhibitory related peptides, with cells offers the opportunity to reveal novel molecular interactions involved in cell growth control.

BSC-1 cell growth was stimulated by gel-fractionated porcine antrum extract; porcine extract protein (250 µg) was loaded into each of 2 lanes and subjected to electrophoresis in a polyacrylamide gel (12.5%); the 5 thin slices (2-3 mm) from each area between $M_r$ 14 kDa and 21.5 kDa were cut from the experimental lanes. Each pair of slices was placed in a silanized microfuge tube with 200 µl sterile PBS, 3% acetonitrule and 1% BSA, and macerated; proteins were eluted from the gel for 18 hr at 22° C. with vigorous shaking; the samples were then microcentrifuged and a sample of a supernatant was added to a confluent culture of BSC-1 cells; the number of cells was counted 4 days later; maximal growth stimulation was observed in cultures receiving extracts eluted from gel slices corresponding to a $M_r$ of 18 kDa; antisera to recombinant human AMP-18 added to the culture medium completely inhibited growth stimulation by the 18 kDa fraction (+Ab); values are means of 2 cultures; SE is less than 10% of the mean.

The biological activity (mitogenic for epithelial cells in the gastro-intestinal tract) of the AMP-18 is located in the C-terminal half of the protein. The epitopic sequence(s) appear(s) to be immediately N-terminal to the mitogenic sequence.

The biological activity that is a growth factor, is exhibited by a peptide comprising at least 42 amino acids from positions 78 to 119 of the full-length protein sequence. An antibody to this region blocked mitogenic activity. Although a peptide having an amino acid sequence of 104 to 117 had mitogenic activity, an antibody to this region did not block (inhibit) the activity. A peptide with an amino acid sequence from positions 97-117 has the same mitogenic activity as a peptide with the 42 amino acid sequence, but is less expensive to produce as a synthetic peptide.

3. Inhibition of Bioactivity

Epithelial cell growth that was stimulated by murine or porcine antrum cell extract was blocked by rabbit antiserum to a complete, recombinant human AMP-18 precursor protein; confluent cultures of BSC-1 cells were prepared; murine or porcine antrum cell extract was prepared and its protein concentration was measured; cell extracts alone and with different dilutions of the antiserum, or antiserum alone (1:100 dilution was added to the culture medium, and the number of cells was counted 4 days later). Growth stimulation by murine antrum gastrokines was maximally inhibited by the antiserum (93%) at a dilution of 1:400, whereas stimulation by the porcine antrum protein extract was totally inhibited at a dilution of 1:100. Scored values were means for 3 cultures; standard error of the mean (SE) was less than 10% of the mean.

Antibodies to the AMP-18 protein have diagnostic uses to determine different levels of the protein in the gastro-intestinal tract in vivo. Ulcers are likely to develop if less than normal levels of AMP-18 protein are present. Normal values are determined by technologies known to those of skill in the art, that is, obtaining representative samples of persons to be tested (age, sex, clinical condition categories) and applying standard techniques of protein quantitation. The effects of aspirin and indamethacin on AMP-18 levels are also useful to monitor deleterious levels of the drugs including the non-steroidal anti-inflammatory drugs (NSAIDs). Stomach cancer cell lines do not express the AMP-18 proteins at least by detection methods disclosed herein.

4. Genomic DNA

Genomic AMP-18 DNA sequences have been cloned for human and mouse as a prelude to the analysis of the gene regulatory elements, which presumably determine the great differences in the levels of expression of the gene in tissues where the gene may be active. Upstream and downstream flanking sequences have been isolated from mouse genomic DNA preparatory to a gene knockout. The flanking genomic sequences likely determine the very different levels of expression of the gene in the stomach and few other tissues where it may be expressed. With the involvement of different regulatory elements, gastrokine genes could be expressed as a growth factor in other tissues.

5. Uses of Gastrokines of the Present Invention

Because the AMP-18 protein and certain peptides derived from it can stimulate growth and wound repair by stomach and intestinal epithelial cells (as well as kidney) these gastrokine molecules are candidates for therapeutic agents to speed recovery of the injured GI tract following pharmacological interventions, radiotherapy, or surgery. In addition, the antibodies developed to gastrokines may be used in kits to measure the levels of AMP-18 protein or peptide in tissue of blood in diverse pathological states. These novel molecules have great therapeutic potential in the treatment of gastric ulcers, and inflammatory bowel disease, whereas new agents that inhibit its function could prove useful in the treatment of cancers of the GI tract.

The stomach is not a congenial location for many bacteria, and those that can survive the acidity do not establish themselves there (Rotimi et al., 1990). It is of interest therefore that the antrum region is the favored site for the attachment, penetration and cytolytic effects of *Helicobaccter pylori*, an agent which infects a major proportion of the human population (>60% by the seventh decade) and has been associated with gastritis, gastric and duodenal ulcers (Goodwin et al., 1986; Blaser, 1987) and gastric adenocarcinomas (Nomura et al., 1991; Parsonnet et al., 1991). Thus as an epithelial cell growth factor, AMP-18 may act to ameliorate the damage caused by bacterial infiltration and cytolysis. Given the conjunction of the specific antrum expression of AMP-18 and the preferred site of binding of *H. pylori*, it is possible that the bacteria use AMP-18 as a tropic factor. *H. pylori* attaches to cells of the antrum having fucose-containing mucin granules (Falk et al., 1993; Baczako et al., 1995). These granules also may contain AMP-18. Anti-microbial peptides have been found in the stomach of the amphibian *Xenopus laevis* (Moore et al., 1991). Some domains of the AMP-18 structure resemble that of the magainins, and possibly AMP-18 interacts with enteric bacteria.

6. Isolation of Pig AMP-18

Antisera against human AMP-18 protein were used to assist in the purification of the protein from extracts of pig antrum mucosa. Immunoaffinity methods applied to total tissue extracts have not proven very effective, but by using immunoblots to monitor cell-fractionation, gradient centrifugation and gel electrophoresis sufficient amounts of the pig 18 kDa polypeptide was purified to confirm by sequencing that the native N-terminus is the one predicted by cleavage of 20 amino acids from the N-terminus of the ORF precisely at the alanine-aspartate site anticipated for signal peptide removal. Despite the abundance of asparagine residues in the mature protein, none fit the consensus context characteristic of glycosylation. Fairly extensive regions of the protein may possess amphipathic helix forming propensity. The latter may represent units within the protein yielding bioactive peptides after processing. Using circular dichroism the synthetic peptide representing amino acids 126-143 in the human preAMP sequence (FIG. 3) is readily induced to become helical in moderate concentrations of trifluoroethanol conditions used to assess helix propensity for some bioactive peptides, including anti-microbial peptides of the magainin type (see, for example, Park et al., 1997).

7. Preparation of Active Recombinant Human AMP-18 in E. coli

Figure 13:
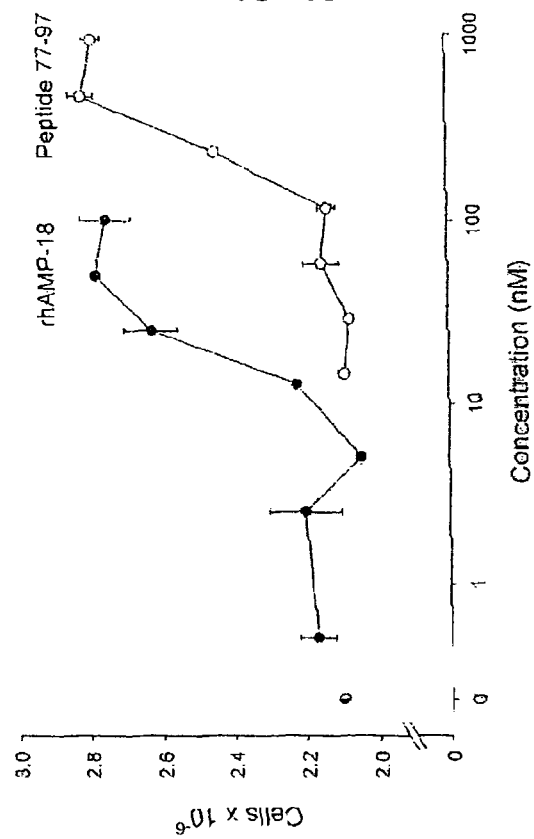
FIG. 13 shows Left panel. Amino acid sequence of recombinant human AMP-18 (residues 21-185 of SEQ ID NO: 3) expressed in E. coli. Note the His6-tag (SEQ ID NO: 16) within a 12 amino acid domain (SEQ ID NO: 9) at the N-terminus that has replaced the putative hydrophobic signal peptide. Right panel. Effect of rhAMP-18 and AMP peptide 77-97 on growth of confluent cultures of IEC-18 cells. Although maximal growth stimulation is similar, the half-maximal concentration 3° ($K_{1/2}$) for rhAMP-18 (~30 nM) is about an order of magnitude lower than for the peptide (~300 nM).

A cDNA encoding human AMP-18 was designed in which the 20-amino acid hydrophobic signal peptide sequence was replaced with an N-terminal 12-amino acid peptide that included a starch of 6 histidine residues (FIG. 13, left panel). Expression of this modified cDNA sequence was predicted to yield a 177-amino acid protein product ($M_r$ 19, 653) that could be readily purified using Ni-NTA resin to bind the His6-tag (SEQ ID NO: 16). The cDNA sequence lacking the region coding for the N-terminal signal peptide (see FIG. 14) was amplified by PCR using oligonucleotides that provided suitable linkers for inserting the product into the BamH1 site of a QE30 expression vector (QIAGEN); the sequence of the recombinant vector was confirmed. The recombinant human (rh) AMP-18 engineered with the His6-tag (SEQ ID NO: 16) was subsequently expressed in E. coli cells. To harvest it, the bacteria were lysed and aliquots of the soluble and insoluble fractions were subjected to SDS-PAGE followed by immunoblotting using the specific rabbit antiserum to the rhAMP-18 precursor. Very little of the expressed protein was detected in the soluble fraction of the lysate.

Urea (6 M) was employed to release proteins from the insoluble fraction solubilize rhAMP-18 containing the His6-tag (SEQ ID NO: 16), and make it available to bind to the $Ni^{2+}$-charged resing from which it was subsequently eluted with a gradient of imidazole (0 to 200 mM). The amount of eluted rhAMP-18 was measured using the BCA assay, and the appearance of a single band at the predicted size of 19-20 kD was confirmed by SDS-PAGE followed by immunoblotting. To determine if eluted rhAMP-18 renatured to assume a structure that was mitogenic, aliquots of the eluate (following removal of urea and imidazole by dialysis) were added to cultures of IEC-18 cells and the number of cells was counted 4 days later. FIG. 13 (right panel) indicates that the recombinant protein stimulates cell proliferation to the same maximal extent as does mitogenic AMP peptide 77-97 (or soluble antrum tissue extracts from pig shown in FIG. 11), but that it does so at a half-maximal concentration an order of magnitude lower than for peptide 77-97. AMP peptide 77-97 refers to the mature protein; same as peptide 97-117 of human precursor protein: Table 1. These observations indicate that biologically active recombinant human AMP-18 that can be utilized in diverse clinical situations is available. The mitogenic potency of rhAMP-18 is in the nanomolar range which would be expected for a native gastric cell growth factor that participates in the maintenance and repair of the stomach in vivo.

8. Stimulation of Growth and Restitution of Stomach and Intestinal Epithelial Cells by AMP-18 and Derived Peptides To characterize the capacity of gastric and intestinal cells to respond to AMP-18, AGS gastric adenocarcinoma cells, HAE human gastric antrum mucosa primary cultures transformed with SV40 large T antigen, rat diploid small intestinal epithelial cells of the IEC-6 (FIG. 15) and IEC-18 lines, NCI N-87 gastric carcinoma cells, and SK-GT5 gastroesophageal adenocarcinoma cells were studied; human WI-38 fibroblasts and HeLa cells served as non-GI control cell lines. Mitogenesis was assayed by performing cell counts 3 to 4 days after exposing cells to the agent of interest, trypsinizing the culture to prepare single cells, and confirming this while counting them in a hemocytometer.

Figure 15:
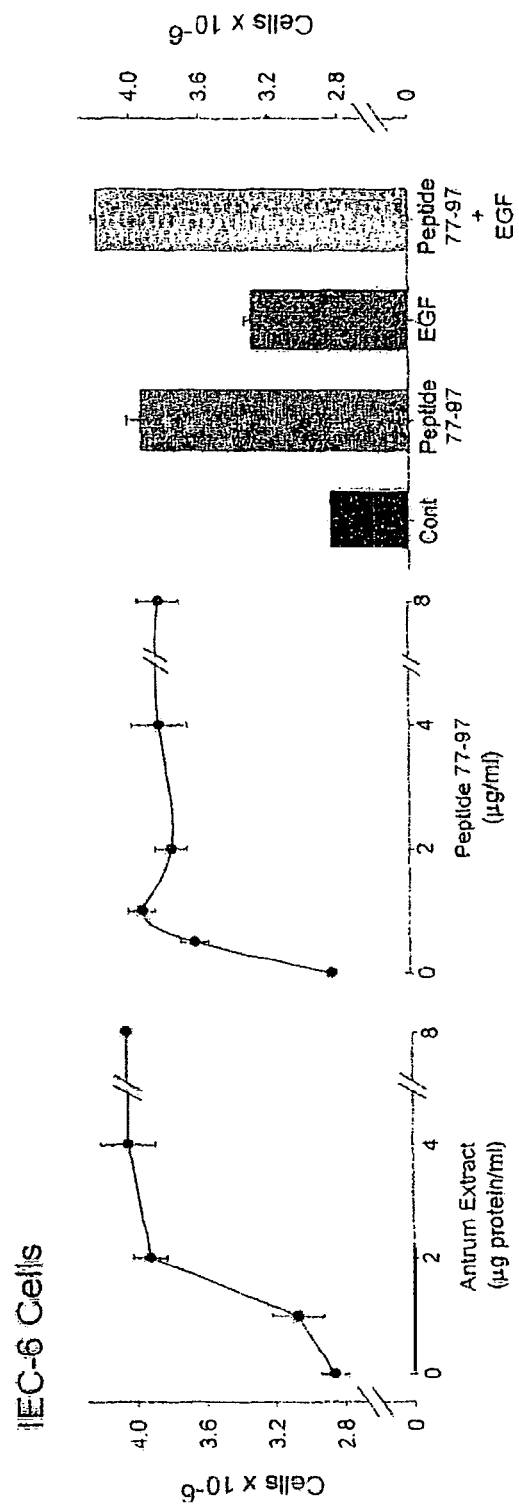
FIG. 15 shows the effect of porcine antrum cell extract, peptide 77-97, and EGF on growth of intestinal epithelial cells. IEC-6 cells were grown in 60-mm dishes. Antrum cell extract (left panel) and peptide 77-97 (center panel) each stimulated growth in a concentration-dependent manner. Peptide 77-97 (1 µg/ml) appeared more potent than EGF (50 ng/ml) (right panel). Values are means±SE for 3 cultures.
Figure 16:
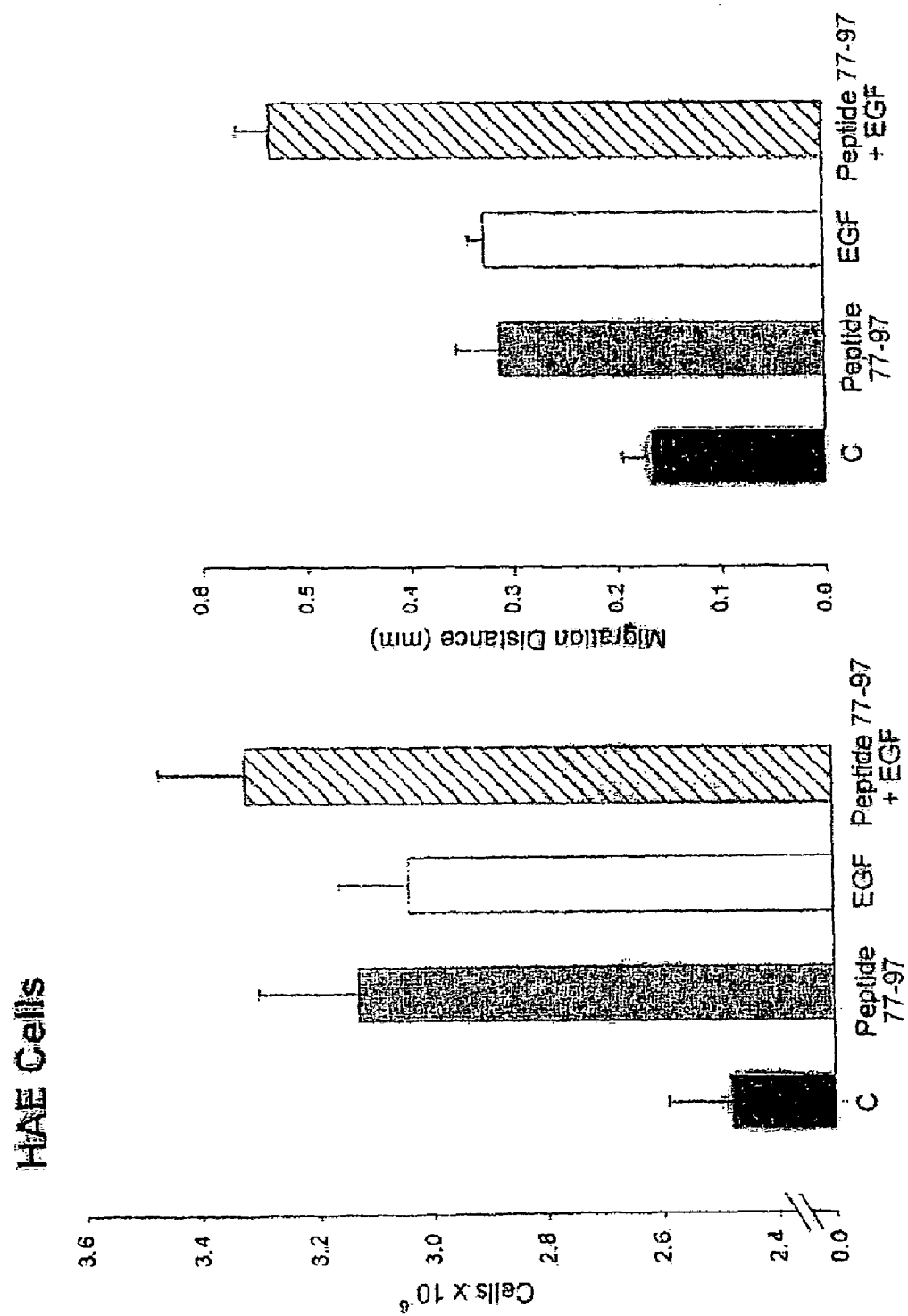
FIG. 16 shows the effect of AMP peptide 77-99 and EGF on growth and wound restitution by human antrum epithelial cells. To measure growth (left panel), HAE cells were plated in 60-mm dishes. Peptide 77-97 (8 µg/ml), or EGF (50 ng/ml), or both were added to the medium and the number of cells counted 4 days later. Peptide 77-97 and EGF each stimulated proliferation, and appeared to be additive. Values are means±SE for 3 cultures. To measure migration (right panel), cells were grown in 60-mm dishes to prepare a confluent monolayer. The medium was aspirated and replaced with fresh medium containing 0.01% calf serum (CS). The monolayer was mechanically wounded by scraping with a razor blade. Detached cells were removed by aspirating medium, and rinsing the remaining cells twice with fresh medium containing 0.01% CS. Fresh medium (5 ml) containing CS (0.01%) and insulin (100 U/L) was added to wounded cultures. Either peptide 77-97 (8 µg/ml), EGF (50 ng/ml), or both were added to duplicate cultures. Migration was assessed at 24, 48 and 72 hr after wounding by measuring the distance (in mm) that cells had migrated from the wound edge using a microscope eyepiece reticle (10-mm long; 0.1-mm markings). Migrating cells at 12 randomly chosen sites along a 0.25-mm stretch of the wound edge were measured at 40-fold magnification. Migration at 2 different sites was measured for each of 2 separate wounds made in each culture. Values are the mean distance cells moved into the denuded area from the edge of 4 different wounds in 2 cultures±SE. Cells exposed to peptide 77-97 migrated further from the wound edge than those exposed to vehicle at 72 hr. EGF also stimulated cell movement, and the two agents acting together markedly enhanced migration.
Figure 18:
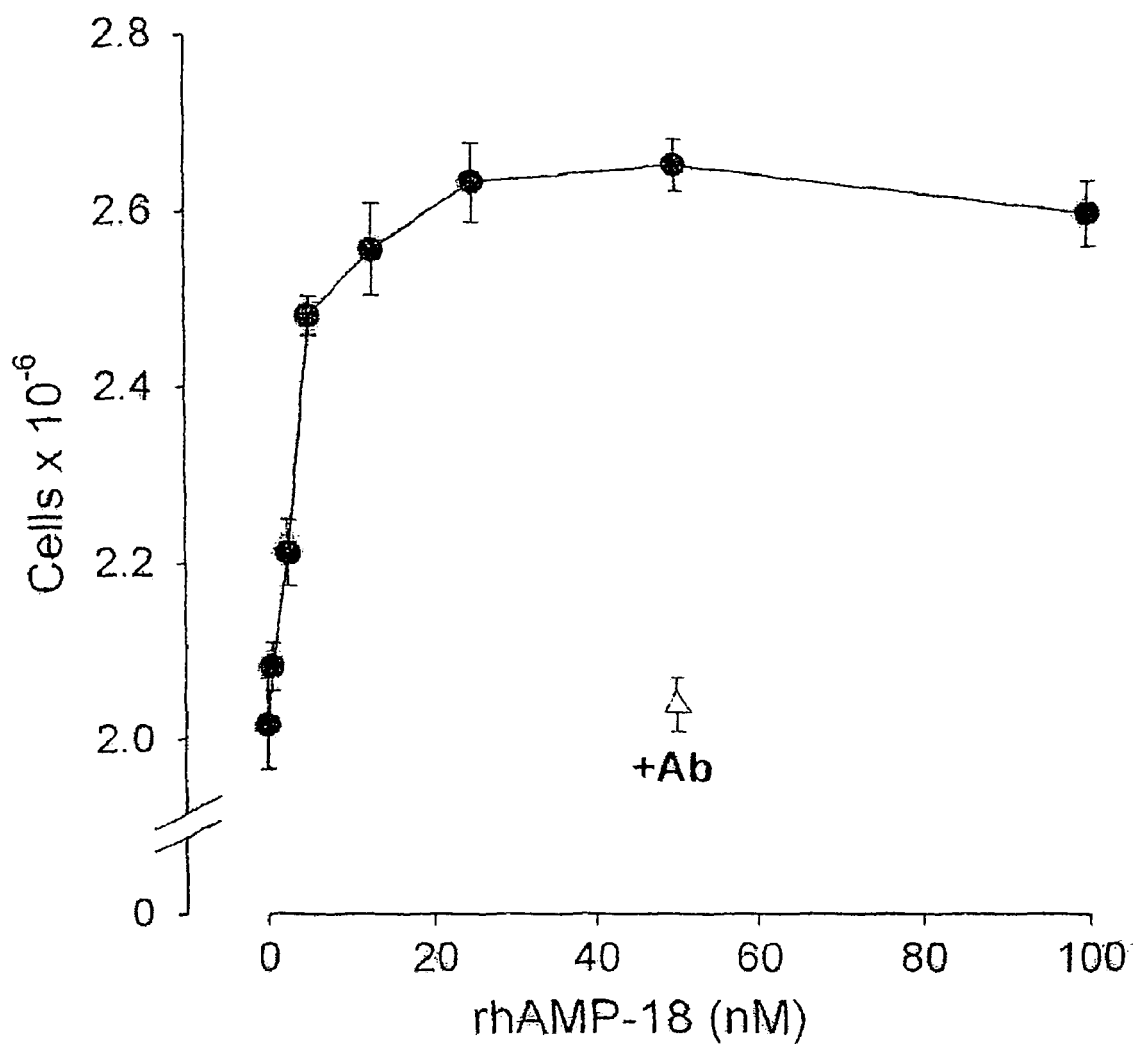
FIG. 18 shows the effect of rabbit antiserum to AMP-18 on mitogenic effect of rhAMP-18 on confluent IEC-18 cells. When rhAMP-18 (50 nanomolar) was preincubated for 30 min with antiserum (1:100 dilution)+Ab), growth stimulation was reduced by ~95%; preimmune serum had no effect on cell growth. The half-maximal concentration ($K_{1/2}$) for growth stimulation of this recently purified rhAMP-18 is about 5 nanomolar.

Antrum extracts containing AMP-18, peptide 77-97, or EGF each stimulated growth of AGS cells, and as expected, the rabbit antiserum to recombinant human AMP-18 precursor protein inhibited the activity of the antrum extract but not of peptide 77-97 which lacks the epitope (FIG. 11. Growth stimulation by peptide 77-97 was additive with that of EGF. Growth of AGS cells is not stimulated by scrambled peptide 77-97 or by peptide 67-85, and peptide 67-85 completely inhibits growth stimulation by peptide 58-99. HAE cells were used to test whether AMP-18 can exert an effect on epithelial cells that exist in he local environment of its synthesis. These cells, provided by Dr. Duane Smoot, Howard University College of Medicine, are not completely immortalized and therefore have limited passage number. Growth stimulation of HAE cells by peptide 77-97 was apparently additive with that of EGF (FIG. 16, left panel). Not only does the AMP peptide stimulate growth but it also acted as a motogen, resulting in more rapid migration (restitution) of cells into scrape wounds made in confluent cultures. This enhancement of wound restitution also showed high additivity with EGF (FIG. 16 right panel). Whether there is a synergism or not, the observed additivity supports that AMP-18 may play an important role in maintaining an intact stomach mucosal epithelium, and in facilitating its repair after injury. The growth of rat diploid IEC-6 cells was also stimulated by the antrum extract, peptide 77-97, and EGF, although the peptide appeared a more potent mitogen than EGF (FIG. 15). Near-maximal growth stimulation was detected at an AMP peptide concentration of 0.5 μg/ml (0.23 μM) (FIG. 15, center panel), a much lower value than the concentration needed for trefoil peptides (1 μg/μl) (~150 μM) or the α-defensin, cryptdin 3 (660 μm/ml) (~140 μM) to exert their effects in culture. The maximal mitogenic effect of rhAMP-18 on IEC-18 cells has been observed at 5 nanomolar (FIG. 18). The mitogenic effect of peptide 77-97 was corroborated by measuring [$^3$H]thymidine incorporation into DNA in IEC-6 cells which was stimulated by 68% (P<0.001) from 16,668±616 to 28,036±882 by the peptide. Stimulation of wound restitution was comparable to EGF, and apparently additive with it. Scrambled peptide 77-97 did NOT stimulate growth of IEC-18 cells or BSC-I cells at concentrations up to 8 μg/ml. Growth of gastric NCI N-87 cells and gastric SK-GT5 cells was also stimulated by peptide 77-97, antrum extract, of EGF in a concentration-dependent manner. AMP-18 antiserum blocked the mitogenic effect of antrum extract, or EGF in a concentration-dependent manner. AMP-18 antiserum blocked the mitogenic effect of antrum extract on these two gastric epithelial cell lines, but not the proliferative effects of peptide 77-97 or EGF. Preimmune serum had no effect on growth. These results suggest that AMP-18 and its peptide derivatives could function in vivo to stimulate growth and restitution during repair after injury. Growth of human fibroblastic (WI-38) or epidermoid (HeLa) cells at concentrations up to 8 μg/ml, suggesting that its mitogenic effect is relatively epithelial-cell specific. AMP peptide 77-97 does not stimulate growth.

9. Competitive Inhibition of IEC-18 Cell Growth by AMP Derived Peptides

Figure 17:
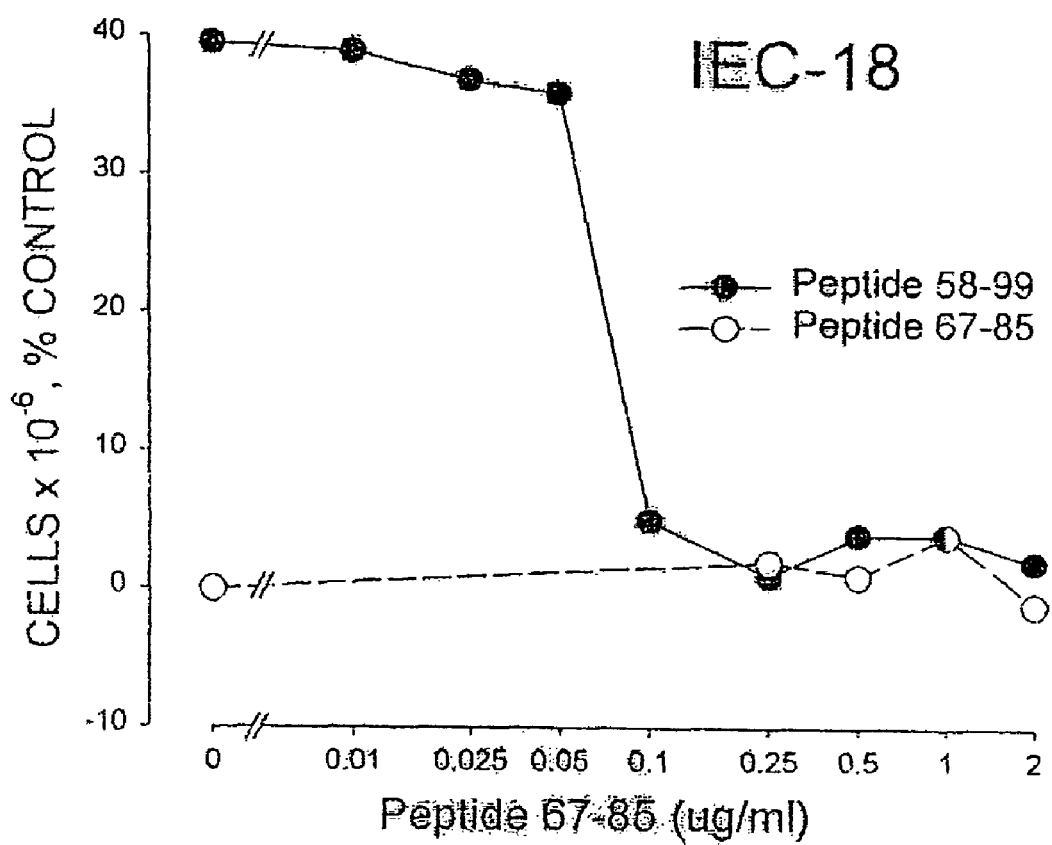
FIG. 17 shows the effect of AMP peptide 67-85 on growth of intestinal epithelial cells stimulated by peptide 58-99. Confluent cultures of IEC-18 cells were prepared. One day later, medium was aspirated and replaced with 5 ml of DMEM containing CS (0.5%) and insulin, without (control) or with mitogenic peptide 58-99 (8 µg/ml). Sister plates receiving 1 ml medium and different amounts of peptide 67-85 were incubated at 1 hr at 38° C. on a $CO_2$ incubator, and then an additional 4 ml of medium was added to each dish. Peptide 58-99 was added to 2 of the 4-sister plates at each concentration of peptide 67-85, and the number of cells was counted. In the absence of peptide 67-85, cell number increased by 290%, whereas cells exposed to peptide 58-99 increased in number by 407%, and EGF-treated (50 ng/ml) cells increased by 402% (not shown) during the next 3 days. Stimulation of cell growth by mitogenic peptide 58-99 was completely abolished by preincubation of cells with 0.25 µg/ml of peptide 67-85. When added alone, peptide 67-85 (0.25 to 8 µg/ml) was not a mitogen. Values for the number of cells per culture are shown relative to multiplication of cells exposed to the vehicle during the same period.

To gain additional information about the interaction between AMP peptides and their binding site(s) on the cell surface, non-transformed rat IEC-18 cells were studied. Progressively increasing the concentration of non-mitogenic peptide 67-85 blocks growth-stimulation by peptide 58-99 if this mitogenic 42-mer exerts its effect by a receptor-mediated mechanism. Peptide 58-99 stimulated an increase in cell number of 407% compared to 290% by the vehicle in a 3-day assay. As the concentration of peptide 67-85 was raised progressively to ~0.1 μg/ml, the growth-stimulatory effect of peptide 58-99 was nearly abolished (FIG. 17). This result suggests that the two peptides compete for the same surface "receptor" site.

10. Antiserum to AMP-18 Neutralizes the Mitogenic Effect of rhAMP-18

Ongoing studies reveal that rabbit antiserum to AMP-18 precursor recognizes rhAMP-18 on immunoblots. The antiserum also blocks the mitogenic effect of porcine antral tissue extracts (FIG. 11) and AMP peptide 58-99, and immunolocalizes AMP-18 in cells of human and murine gastric antral tissue. FIG. 18 shows that the antiserum neutralizes the mitogenic effect of rhAMP-18 in confluent cultures of IEC-18 cells, thereby extending its utility to study the recombinant as well as native protein.

Using GI epithelial cells, results suggest that the cytoprotective effect of rhAMP-18 may be mediated by its capacity to facilitate accumulation of tight junction (TJ) proteins, and that it is a potent mitogen. The results also imply that AMP peptide 77-97 is an appropriate surrogate for rhAMP-18, although the peptide requires a relatively higher concentration to exert its physiological effects (FIG. 13).

To improve the yield of rhAMP-18, an EDTA-free protease-inhibitor cocktail is used, lysozyme is added to digest *E. coli* cell debris, and recombinant protein is eluted from $Ni^{2+}$ beads with 1M imidazole.

11. AMP Peptide Stimulates Restitution of Gastric and Intestinal Epithelial Cells after Scrape-Wounding.

Figure 19:
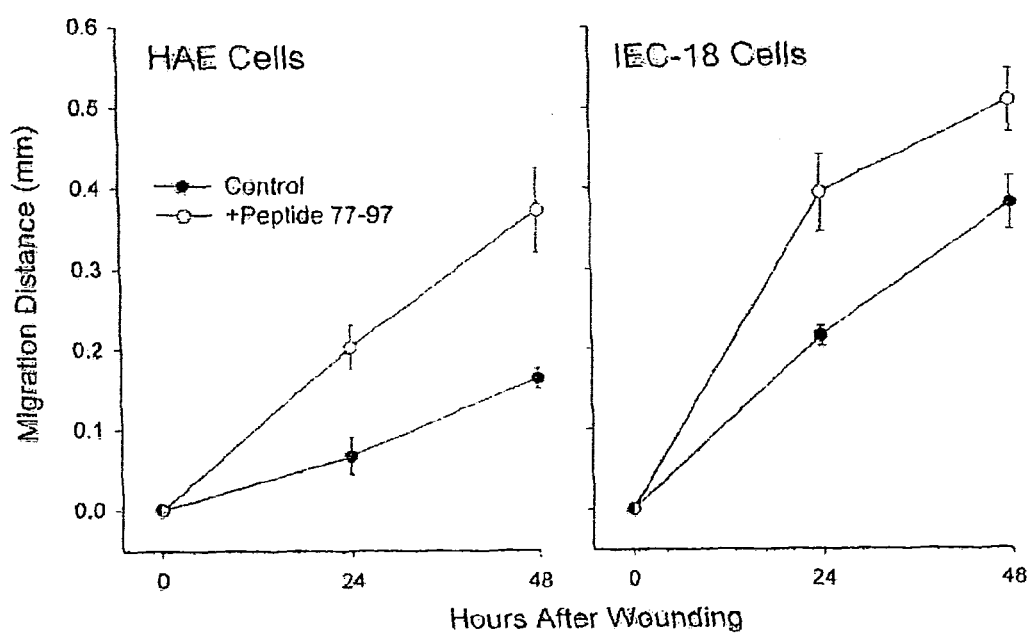
FIG. 19 shows the effect of AMP peptide 77-97 on wound restitution in human antrum (HAE) and rat intestinal (IEC-18) epithelial cells. Confluent monolayer cultures were mechanically wounded by scraping with a razor blade, and the distance that cells migrated from the wound edge was measured using a microscope eyepiece reticle. Cells migrated further in the presence of AMP peptide at each time point studied (P<0.005).

Data presented in FIG. 19 were obtained after 24 to 48 hr exposure to AMP peptide, times before a mitogenic effect can be detected by an increase in cell number. The results indicate that AMP peptide stimulates restitution in scrape-wounded human gastric adenocarcinoma-derived cells of the HAE line, and in nontransformed rat intestinal cells of the IEC-18 line. Thus AMP peptide rapidly stimulates restitution of gastric and intestinal epithelial cells in culture, and presumably could speed resurfacing of the injured gastric mucosa in vivo.

12. AMP Peptide Induces Tyrosine Kinase Activity Suggesting that its Functional Effects are Mediated by a Cell Surface Receptor To obtain evidence that the physiological effects of AMP-18 are specific and receptor-mediated, AMP peptide was tested to see if it induces tyrosine phosphorylation in GI epithelial cells.

IEC-18 cells were treated with AMP peptide 77-97 at a concentration previously shown to be in excess of that required for maximal growth stimulation for different periods of time up to 60 min. The cells were then lysed, the protein extracted and separated on SDS-polyacrylamide gels, blotted, and the blot probed with 4G10 anti-phosphotyrosine monoclonal antibody. The blot showed that exposure of cells to AMP peptide (8 μg/ml) results in tyrosine phosphorylation of several proteins after two min, including those having molecular masses of 42- and 55-kDa, suggesting a role for activated ERK1 and ERK2 in AMP-18 signaling. There was a decline in the extent of tyrosine phosphorylation of several of the proteins after 5 min, and persistence of others for up to 60 min.

AMP peptide and presumably AMP-18 may signal their mitogenic, motogenic, and cytoprotective effects via a cell surface receptor, and possibly stimulate tyrosine phosphorylation of specific cell proteins.

Figure 20:
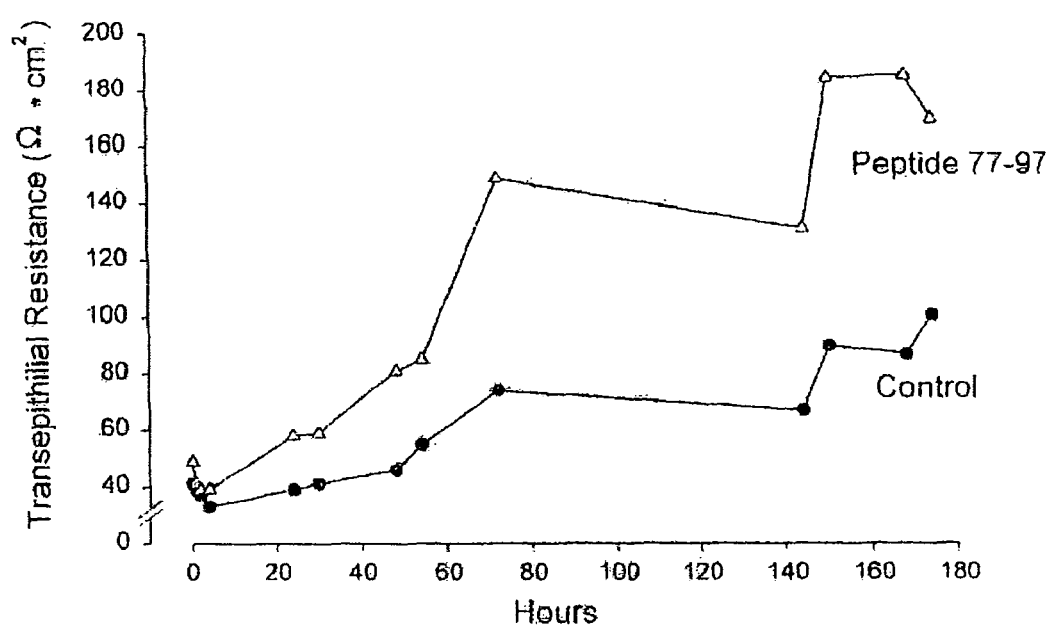
FIG. 20 shows the effect of AMP peptide 77-97 on maturation of TER. Monolayer cultures of MDCK cells were grown on permeable polycarbonate filters (0.4-µm pore size) (Transwell) in DMEM containing FBS (2%) without (control) or with peptide 77-97 (8 µg/ml) for 8 days. TER was measured 24 hr after the cells were plated, and at specified times thereafter using an epithelial volt-ohm meter (EVOM, Millipore). Following each measurement, medium containing FBS without or with peptide was changed (0, 48, and 144 hr), and additional peptide 77-97 (8 µg/ml) was added at 30 and 72 hr. At 72 hr, TER in cultures that received peptide 77-97 was twice as high as in control cultures. Values are means for 3 cultures; variance is <10% of the mean. TER was measured from 3 different areas on filter.

13. AMP Peptide 77-97 Enhances Development of Barrier Function of Epithelial Cells and is Cytoprotective Maintenance of barrier function is essential for preventing entry of foreign antigens and bacteria from the gastric lumen, and for other functions such as vectorial transport of electrolytes, water and nutrients. Acting alone or in concert with other agents, AMP-18 might mediate the rapid return of barrier function following mucosal injury. To determine whether AMP peptide 77-97 could facilitate development of barrier function, and could also serve as a cytoprotective agent to prevent loss of function when reactive oxygen metabolites, indomethacin, or dextran sulfate sodium (DSS), increases mucosal permeability and compromises cell integrity needed to maintain epithelial tight junctions. Cell lines known to develop relatively high values for TER as a marker of epithelial tight junctions were used. Initially, peptide 77-97 modulates maturation of TER in monolayer cultures of well-characterized, nontransformed MDCK cells. FIG. 20 shows that exposure to the peptide increases TER in the monolayer by 24 hr, and to a greater extent thereafter. This observation suggests that AMP-18 or AMP peptide could speed recovery of the GI epithelium after injury, and enhance development of barrier function.

Figure 21:
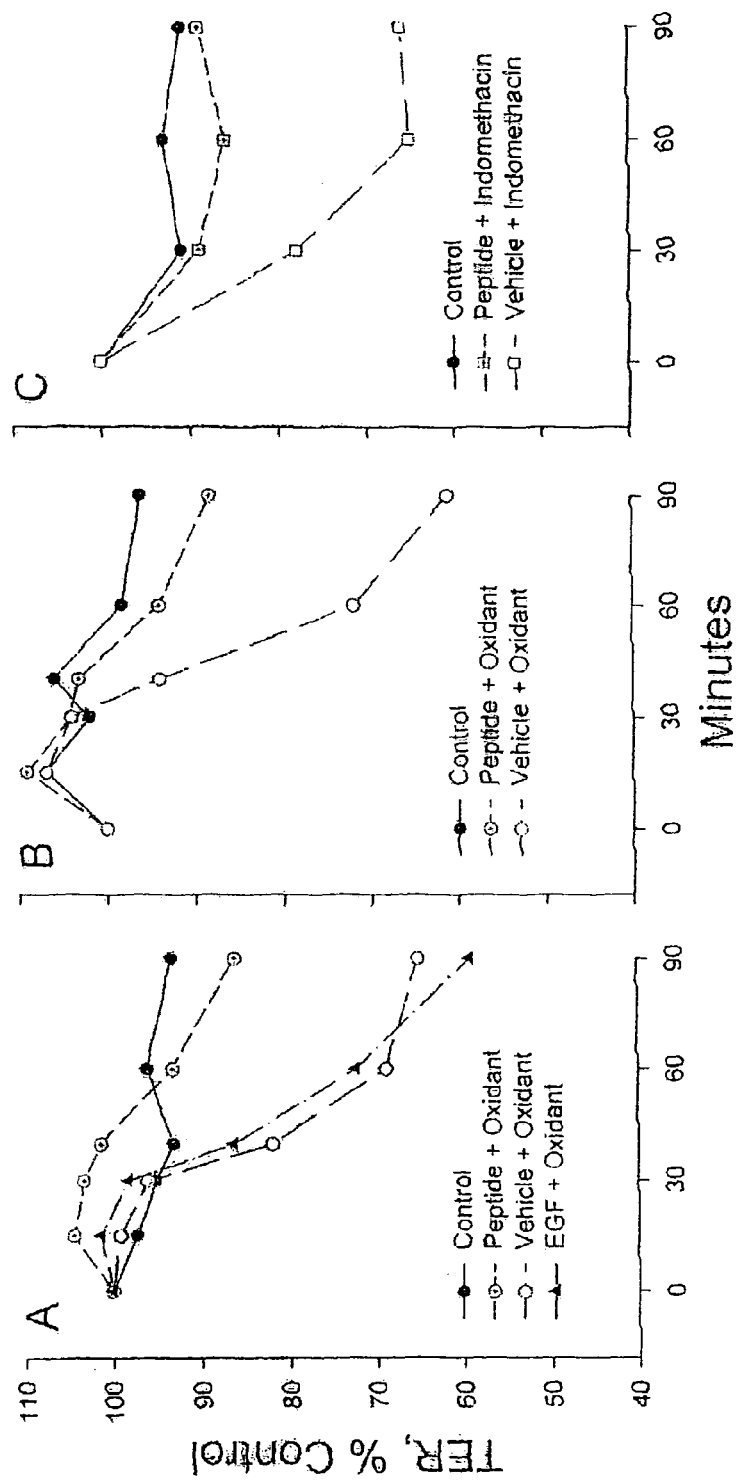
FIG. 21 shows the effect of AMP peptide 77-97 on TER in monolayers injured with the oxidant monochloramine or indomethacin. Panel A: When a stable TER was reached (330 $\Omega \cdot cm^2$) in MDCK cell monolayers the medium was changed to DMEM containing FBS (0.2%), and either peptide 77-97 (8 µg/ml) or EGF (50 ng/ml). After 18 hr, peptide 77-97 or EGF were added to the specified wells. One hour later monochloramine (0.1 mM), like the other agents, was added to the apical and basal compartments of the Transwell. Monochloramine-injured cultures treated with vehicle or EGF sustained ~35-40% loss of TER 90 min after oxidant exposure, whereas the TER of oxidant-injured cells treated with peptide 77-97 was similar to control cultures not exposed to the oxidant. Panels B, C: Caco2/bbe (C2) subclone monolayers were grown on collagen-coated polycarbonate filters until a stable TER was reached (225 $\Omega \cdot cm^2$). Spent medium was replaced with fresh medium containing FBS (0.1%) alone or with peptide 77-97 (8 µg/ml). After 18 hr, monochloramine (0.3 mM, B) or indomethacin (0.1 mM, C) was added to both compartments of the Transwell. At time 0, cultures received either vehicle (control), vehicle plus oxidant or indomethacin, or peptide 77-97 and oxidant or indomethacin. TER of injured cultures treated with vehicle decreased by ~35% at 90 min, whereas peptide-treated cultures declined ~10%. The peptide did not alter TER of non-injured cells (not shown).

To determine whether AMP peptide protects barrier function in a tissue culture model of mucosal oxidant injury, cell monolayers were subjected to reactive oxygen metabolite injury using monochloramine. The results in FIG. 21 (panel A) indicate that after 60 min of exposure to monochloramine, MDCK cells treated with vehicle or EGF show a substantial loss of TER, whereas the TER of cultures treated with peptide 77-97 is similar to non-injured monolayers. These results are of considerable interest because they suggest that AMP peptide but not EGF is cytoprotective under this set of conditions, whereas these two molecules were previously found to be equivalent and additive mitogens and motogens for gastric and intestinal epithelial cells. The cytoprotective effect of peptide 77-97 was also apparent in Caco2/bbe (C2) cells derived from a human colonic adenocarcinoma line in the setting of oxidant (FIG. 22, panel B) or indomethacin-mediated (panel C) injury.

14. Cytoprotective Effect of AMP Peptide Following DSS Injury

Figure 22:
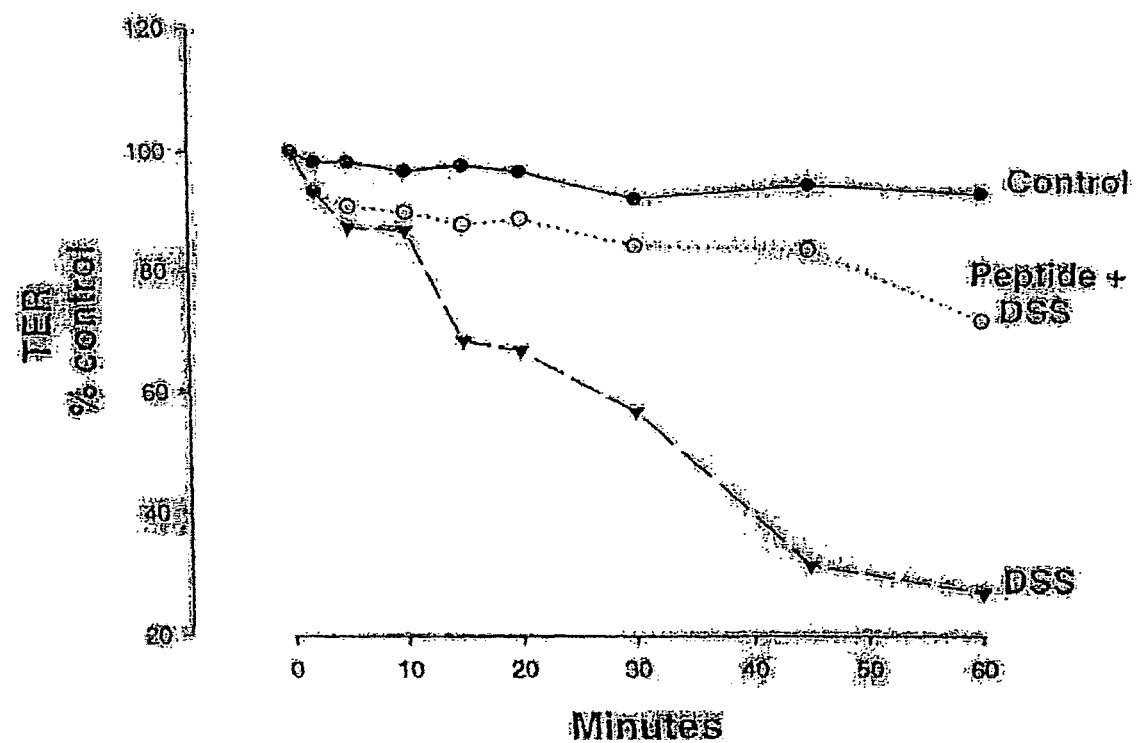
FIG. 22 shows the effect of AMP peptide 77-97 on TER following injury by DSS. C2 cell monolayers were grown in DMEM containing FBS (5%) and transferrin (10 µg/ml) on collagen-coated polycarbonate filters until a stable TER was reached (225 $\Omega cm^2$). At time 0, cells were exposed to no DSS (control), or DSS (4%) in the upper compartment of the Transwell. AMP peptide 77-97 (8 µg/ml) was added to the upper and lower compartments of the Transwell 1 day prior to the addition of DSS at time 0. TER of DSS-injured cultures treated with vehicle decreased by ~70% at 45 min, whereas peptide-treated cultures declined ~10% at that time. The peptide did not alter TER of non-injured cells. Values are means for $\geq 6$ cultures.

To evaluate the potential capacity of AMP peptide to exert a cytoprotective effect in colitis in vivo, a solution of dextran sulfate sodium (DSS) was added to the culture medium of C2 cell monolayers used to model the colonic epithelium. DSS-mediated injury of barrier function was quantified be measuring TER in these monolayer cultures. FIG. 22 indicates that DSS (4%) reduced the TER to ~30% of the control value after 45 min, and that AMP peptide was cytoprotective. This observation provides a strong physiological rationale for evaluating AMP peptide as a therapeutic agent in the murine model of DSS-mediated colitis.

To determine whether AMP peptide could speed recovery of TER after DSS-induced colonic cell injury, a highly sought-after functional characteristic of an agent designed to treat IBD, C2 cell monolayers were exposed to DSS (5%) for 10 min which reduced TER to 33±6% of the control value. DSS was removed by aspirating the medium and replacing it with fresh medium. AMP peptide 77-97 (8 μg/ml) or vehicle was added to the culture medium, and TER was measured 18 hr later. In the presence of the vehicle, TER increased from 33% to 66±7% of the control value, whereas cells exposed to AMP peptide reached a value 112±4% of control. The salutary results in a tissue culture model of DSS-mediated colitis suggest that AMP peptide can speed recovery of barrier function in the injured colonic epithelium in vivo.

Figure 23:
FIG. 23 shows the effect of AMP peptide 77-97 on ZO-1 and occludin after oxidant injury of C2 cells. This immunoblot shows that protein levels in the insoluble fraction are ~two-fold greater after exposure of cells to AMP peptide than to the vehicle.
Figure 24:
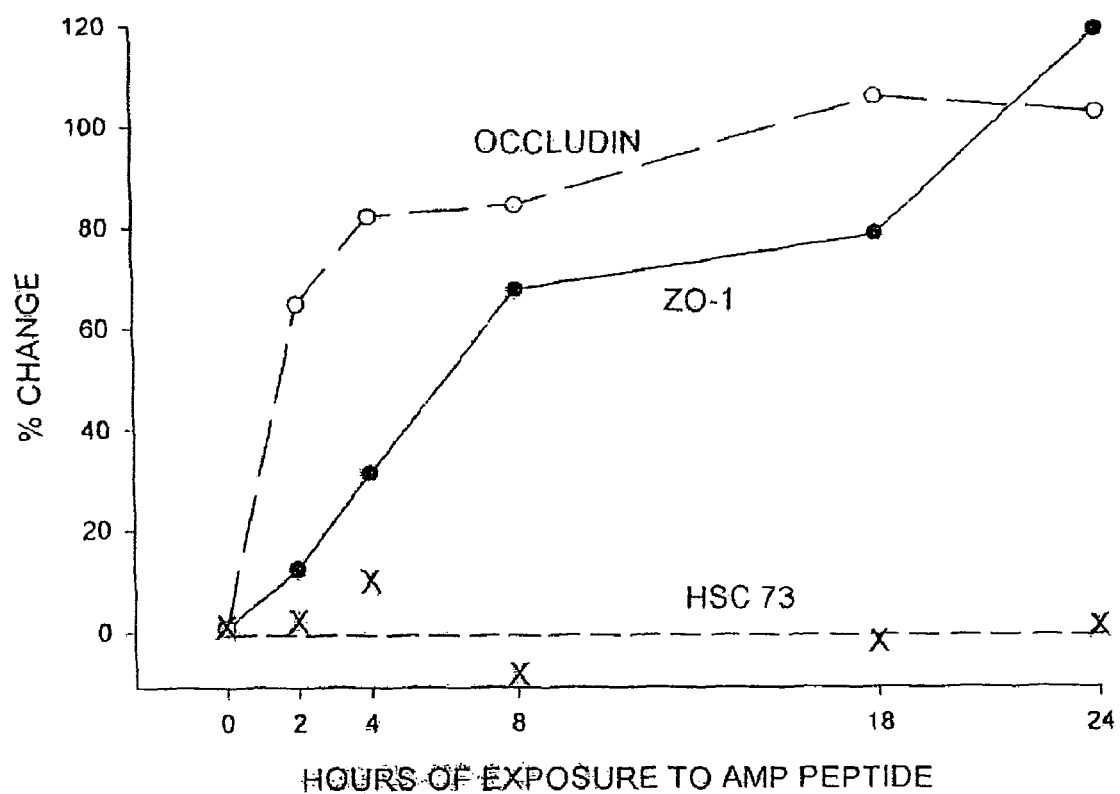
FIG. 24 shows the effect of AMP peptide on C2 cells. Cultures were exposed to the peptide for different periods of time and the insoluble fraction was obtained. Proteins were separated, immunoblots were probed with specific antisera, and the amount of each protein was quantified using laser densitometry.

15. The Cyprotective Effect of AMP Peptide in Colonic Epithelial Cells may be Mediated by Increased Accumulation of Tight Junction Proteins FIG. 21B shows that AMP peptide 77-97 blunts the fall in transepithelial electrical resistance (TER) in Caco2/bbe (C2) cells after oxidant injury. To find out how the peptide exerts its cytoprotective effect, C2 cell monolayers were treated with AMP peptide, and oxidant injury was induced with monochloramine 18 hours later. Changes in the levels of specific tight junction (TJ) proteins were checked. Cells were lysed, and proteins of the insoluble/particulate fraction were studied by immunoblotting. FIG. 23 shows that there is more immunoreactive ZO-1 and occludin in AMP peptide-treated than in vehicle-treated cells at time 0, and for 60 minutes following oxidant-induced injury, suggesting that the greater abundance of these TJ proteins thereby blunts loss of TER in the monolayer and preserves barrier function. These observations implied that AMP peptide enhanced TJ protein accumulation during the 18 hours before cells were subjected to oxidant injury. Non-injured cells were studied and showed that AMP peptide (or rhAMP-18) rapidly increased the amount of immunoreactive ZO-1 and occludin compared to untreated cells (FIG. 24). These changes appear relatively specific for ZO-1 and occludin as they were not observed for several other TJ proteins (ZO-2, claudin-1, claudin-2, claudin-5), or heat shock protein (HSC) 73.

16. Cytoprotective Effect of rhAMP-18

Figure 25:
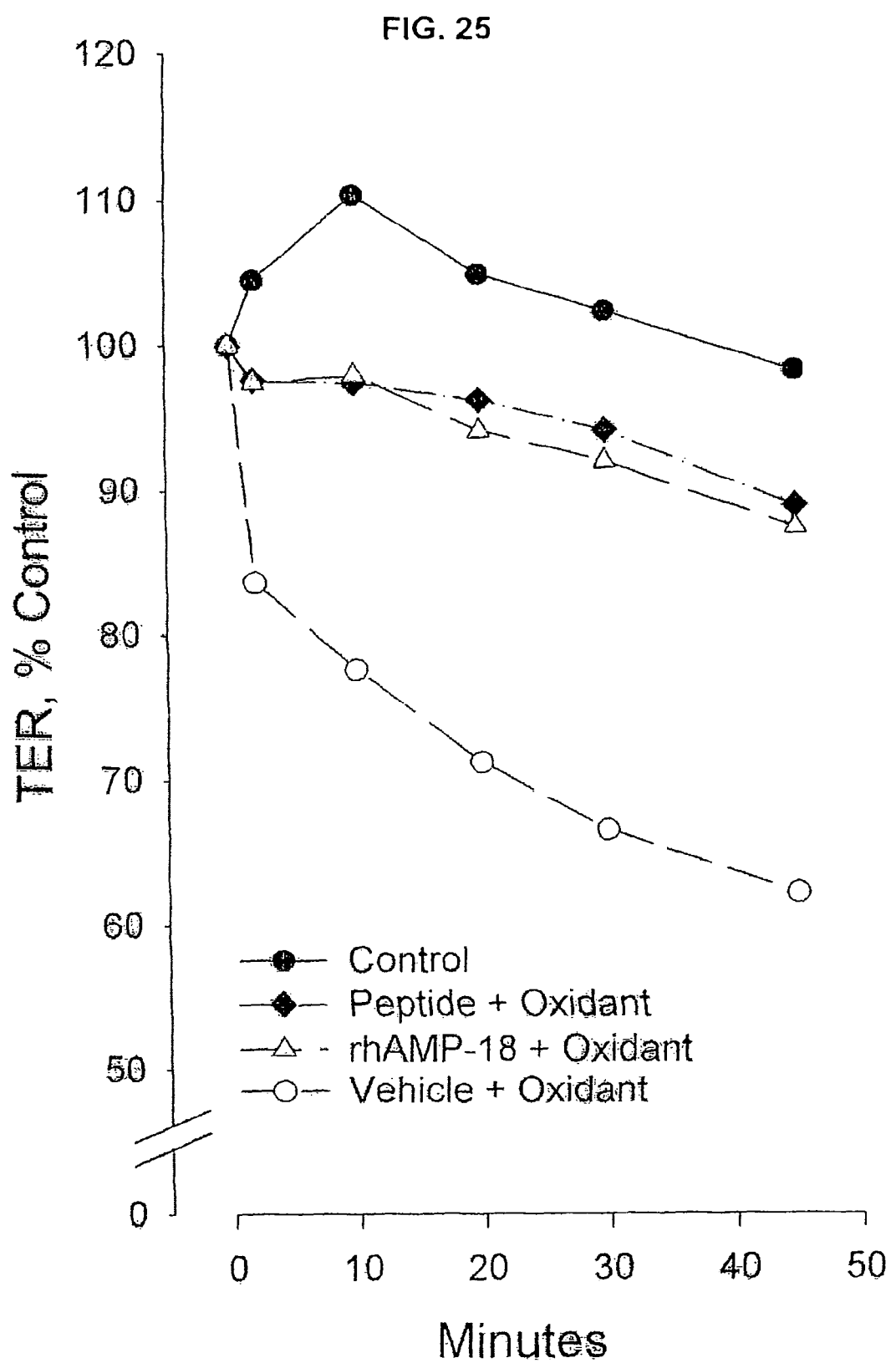
FIG. 25 shows the effect of rhAMP-18 on TER of monolayers subjected to oxidant injury. Confluent C2 cell monolayers were prepared on Transwells until a stable TER was established. Medium was replaced with fresh medium containing FBS (0.1%) alone (control), or with either rhAMP-18 (100 nanomolar) or peptide 77-97 (3.7 micromolar). After 18 hr, monochloramine (0.3 mM) was added to both compartments of the Transwell, and cultures received either vehicle (control), vehicle plus oxidant, rhAMP-18 and oxidant, or peptide 77-97 and oxidant, after which TER was measured.
Figure 26:
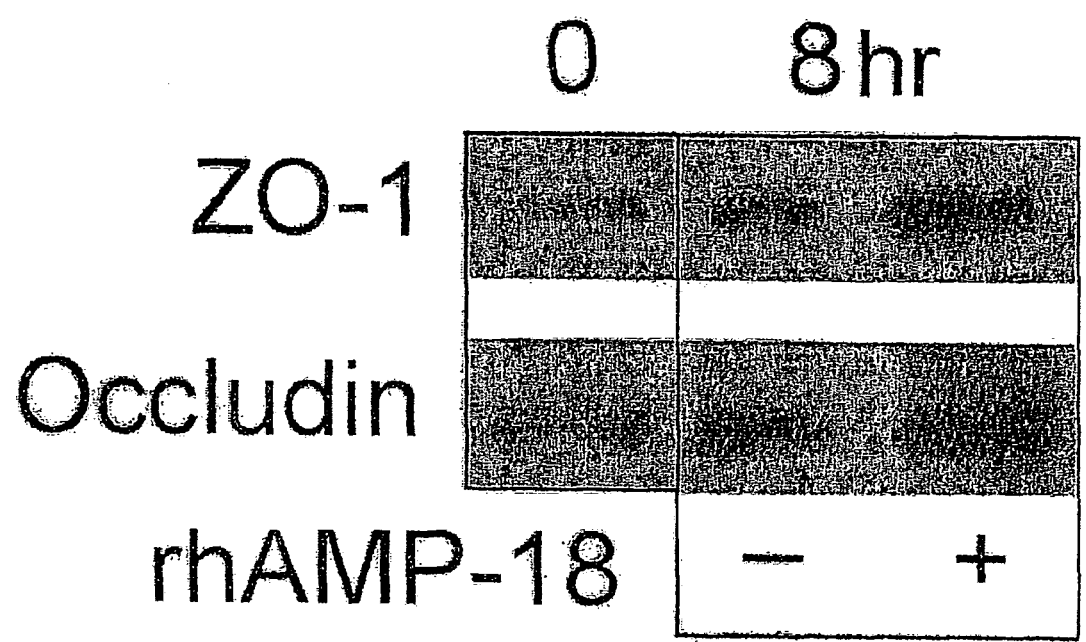
FIG. 26 shows the effect of rhAMP-19 on levels of ZO-1 and occluding in C2 cells. Monolayer cultures were treated with rhAMP-19 (100 nanomolar) or the vehicle for 8 hr. Following cell lysis, an insoluble (particulate) fraction representing cell membranes and cytoskeleton-associated TJ protein was prepared and then subjected to immunoblotting. The amount of immunoreactive ZO-1 and occludin is about two-fold greater in rhRMP-18-treated (+) cells than vehicle-treated (1) cells as estimated by laser densitometry of the same immunoblot. Equal protein loading in each lane was documented by re-probing the blot with an antibody to heat shock protein 73 which is constitutively expressed by these cells.

A sufficient amount of purified rhAMP-18 was prepared to test whether rhAMP-18 was cytoprotective compared to AMP peptide 77-87 which blunted the fall in transepithelial electrical resistance (TER) in Caco2/bbe (C2) cells following monochloramine-mediated oxidant injury (FIG. 21B). FIG. 25 shows that exposure to monochloramine reduces TER by ~35% at 45 min, whereas cells pre-treated with either rhAMP-18 or peptide 77-97 exhibited only a ~10% decline in TER. FIG. 26 indicates that treatment of C2 cells with rhAMP-18 for 8 hr increases the amount of immunoreactive ZO-1 and occludin compared to vehicle-treated cells. These results suggest that AMP-18 could mediate its cytoprotective effect by enhancing accumulation of specific TJ proteins and thereby preserve barrier function along the GI tract following mucosal injury.

17. Administration of AMP Peptide Delays Appearance of Blood in the Stool and Reduces Weight Loss in Mice with DSS Induced Colitis To evaluate the therapeutic efficacy of AMP peptide, DSS colitis was induced in C57/BL6 male mice by giving animals (12-15 µm each) 3% DSS ($M_r$ 36-44 kDa) in the drinking water. Evidence of colitis (blood in the stool) was found as early as day 1 (FIG. 27, left panel), and in all animals by day 4. AMP peptide, administered daily by subcutaneous (s.c.) injection, delayed the appearance of hemoccult-positive stool, and also reduced the extent of weight loss (FIG. 27, right panel). These positive findings strongly support AMP peptide as a useful therapeutic agent in colitis and other diseases that injure the mucosal surface of the GI tract.

The synthesis of AMP-18 is confined to lumenal mucosal lining epithelial cells of the gastric antrum of humans and other mammals. Inside cells the protein is co-localized with mucins in secretion granules, and appears to be secreted into the mucus overlying the apical plasma membrane. Recombinant human AMP-18 prepared in *E. coli* exerts its mitogenic effect at a concentration an order of magnitude lower than growth-promoting peptides derived from the center of the mature protein. Peptide 77-97, the most potent mitogenic peptide, is amino acid sequence-specific, and appears to be cell-type specific as it does not stimulate growth of fibroblasts or HeLa cells. Mitogenesis by specific AMP peptides appears to be mediated by a cell surface receptor because certain peptides that are not active mitogens can competitively inhibit, in a concentration-dependent manner, the growth-stimulating effects of peptide 58-99 and antrum cell extracts. AMP-18 and its derived peptides exhibit diverse effects on stomach and intestinal epithelial cells which suggest they could play a critical role in repair after gastric mucosal injury. These include cytoprotection, mitogenesis, restitution, and maturation of barrier function after oxidant, DSS, and/or indomethacin-mediated injury. Possible mechanisms by which AMP-18 or its peptide derivatives mediate their pleiotropic effects include stimulation of protein tyrosine kinase activity, prolongation of heat shock protein expression after cell stress, and/or enhanced accumulation of the tight junction-associated proteins ZO-1 and occludin. Certain of these physiological effects can occur at concentrations that are relatively low for rhAMP-18 (<50 nM) compared to the concentrations of other gastric peptide mediators such as trefoil peptides or the α-defensin, cryptdin 3 (>100 µM). Immunoreactive AMP-18 is apparently released by cells of the mouse antrum after indomethacin gavage, and by canine antrum cells in primary culture exposed to forskolin, suggesting that the protein is subject to regulation. AMP-18 likely plays a role in physiological and pathological processes such as wound healing in the gastric mucosal epithelium in vivo. The capacity of AMP peptide to delay the onset of bloody stool in the DSS model of mouse colitis, and reduce the extent of weight loss suggests therapeutic efficacy in diverse diseases that injure the mucosa of the GI tract (inflammatory bowel diseases, gastric ulcer, and the like)

Materials and Methods

1. Isolation of Antrum-Specific cDNA Clones cDNA clones for the gastrointestinal (GI) peptide gastrin, which regulates gastric acid secretion as well as mucosal and pancreatic cell growth (Yoo et al., 1982) were isolated. From these screens several other mRNAs expressed relatively specifically in the antrum of the stomach were found. The open reading frame (ORF) in one of these RNAs was highly conserved between pig and man, and predicted a novel conserved protein of no immediately apparent function. Using specific antibodies, it was shown that similar protein species are present in the stomach antrum mucosa of all mammals tested. There is tissue specificity of expression of these sequences and they are apparently ubiquitously present in the antrum mucosa of mammalian species.

2. RNA Expression

The isolation of the cDNA clones was predicted on a preferential expression in the mucosa of the stomach antrum and this has been confirmed initially by Northern blot hybridization of RNAs from various tissues probed with the cDNA sequences and subsequently by protein analysis. The Northern blots showed the specificity of mRNA expression within the gastrointestinal tract of the pig. Highest mRNA expression was in the antrum mucosa, variable amounts in the adjacent corpus mucosa and undetectable levels in fundus, esophagus and duodenum. The non-mucosal tissue of the antrum and corpus contained little RNA reacting with the cDNA probe.

3. Antibodies to Expressed Protein

The open reading frames (ORFs) of the human and pig cDNA clones predict very similar relatively low molecular weight (MW) proteins, which have no close homologs to known proteins in the computer databases and therefore give little indication of possible function. As an approach to study the biological role of the presumptive proteins, the full cDNA sequences were expressed in *E. coli*, using a vector that also encoded an N-terminal His6-tag (SEQ ID NO: 16). Unfortunately, as expressed in bacteria the polypeptide products are insoluble and not readily amenable to biochemical studies. However, the bacterial product of the human cDNA was separated on sodium dodecyl sulfate (SDS) gels used as an immunogen in rabbits to elicit antisera. The sera were screened against protein extracts of antral tissue from a number of mammalian species. This procedure has successfully produced several high-titer, low background antisera capable of recognizing both the immunogen and proteins of about 18 kDa expressed in the antrum of the mammals tested. The bacterially-expressed protein migrates more slowly because it contains the signal peptide sequence was well as a His6-tag (SEQ ID NO: 16). The preimmune sera showed no significant 18 kDa reactivity. The cross-reactivity of the antisera raised against the protein expressed from the human cDNA clone with proteins of very similar MW in antrum extracts from a variety of mammals (pig, goat, sheep, rat and mouse; the last consistently migrates slightly more rapidly in SDS gels) supports the level of conservation of amino acid sequence predicted by comparison of the ORFs of the human and pig cDNAs (See FIG. 10). In subsequent experiments, human AMP-18 with a signal peptide was produced in bacteria.

The preimmune sera give insignificant reactions on Western blots of all tissue extracts, while the two immune sera (at up to 1:50000 dilution) both give major bands of 18-20 kDa only, and those only in stomach antrum extracts, and to a lesser degree in the adjacent corpus extracts. The sera were raised against bacterially-expressed protein so there is no possibility of other exogenous immunogens of animal origin.

As determined by immunoblots, the specificity of expression to the antrum is even greater than the Northern blots would suggest, and the strength of the signal from antrum extracts implies a relatively high abundance of the protein, although quantitative estimates were not made. Significant antigen was not detected in non-stomach tissues tested.

The immunohistochemistry showed insignificant staining of antral tissue by both preimmune sera, while both immune sera stained the surface mucosal cells very strongly at considerable dilutions. The preimmune sera did not lead to immunogold staining in the immunoelectron microscope study. The growth factor activity of antrum extracts is inhibited by both immune, but not preimmune sera. Finally, the results with a synthetic peptide, which has growth factor activity, is inhibited by the immune but not the preimmune sera, and carries epitopes recognized by the immune but not the preimmune sera, further validate the specificity of these reagents.

4. Northern Blot Hybridization of RNAs From Pig Gut Mucosal Tissues

Total RNA was electrophoresed, transferred to a membrane and hybridized with a labeled pig AMP-18 cDNA probe. The source of the RNA sample for each lane was: 1. Distal duodenum; 2. Proximal duodenum; 3. Antrum; 4. Adjacent corpus; 5. Fundus; 6. Esophagus. Equal amounts of RNA were loaded. The signal from RNA of the antrum adjacent corpus was variable. Size markers (nucleotides) were run on the same gel for comparison.

5. Immunoblots Using A Rabbit Antiserum Raised Against the Bacterial-Expressed Protein Directed By the Human Antrum-Specific cDNA Clone Whole tissue proteins were dissolved in SDS buffer, electrophoresed, and transferred to membranes that were reacted with immune serum (1:50000). Bound antibody molecules were detected using peroxidase-labeled anti-rabbit antibody. Preimmune serum gave no specific staining of parallel blots at 1:200 dilution. Lanes: 1,6,13,17 contained markers. 2 HeLa cells. 3 mouse TLT cells. 4 expressed human protein+HELA cells. 7 mouse corpus. 8 mouse antrum. 9 mouse duodenum. 10 mouse intestine. 11 mouse liver. 12 expressed human protein+TLT cells. 14 mouse antrum. 15 mouse brain. 16 mouse Kidney. 18 pig antrum. 19 mouse antrum.

Immunoblots of high percentage acrylamide gels showed that the antisera recognized epitopes on the synthetic peptide 78-119. The reaction of peptide 78-119 with the antibodies was not unexpected because this region of the sequence was predicted to be exposed on the surface of the protein and to be antigenic. Not only does this further substantiate a belief that AMP-18 or its immediate precursor, is a growth factor, for epithelial cells, but also provides a basis for analysis of the bioactive (and antigenic) regions of AMP-18, and a tool for the assessment of cell receptor number and identity. Chemical synthesis of peptides also makes available a convenient and rapid source of considerable quantities of pure "wild-type" and "mutant" reagents for further cell studies. The synthetic peptide 78-119 apparently acts by the same mechanism as the antrum protein, because their maximal effects are not additive.

6. Sequence and Predicted Structure of the Pre-AMP Open Reading Frame

The predicted amino acid sequences for human and pig are 76% identical. The predicted signal peptides are not bold; the N-terminus of native pig AMP has been shown to be aspartate (FIG. 10).

7. Structure of the Native Protein

The ORF's of the human and pig cDNAs predicted polypeptides of similar general structure (FIG. 10). The predicted molecular weights for the otherwise unmodified human and pig proteins was 18.3 and 18.0 respectively; these values are in good agreement with electrophoretic mobility in SDS the of antrum proteins reacting with the antisera of the present invention.

The antisera was used to assist in the purification of the protein from extracts of pig antrum mucosa. Immunoaffinity methods applied to total tissue extracts have not proven very effective, but by using immunoblots to monitor cell-fractionation, gradient centrifuigation and gel electrophoresis sufficient amounts of the pig 18 kDa polypeptide was purified to confirm by sequencing that the native N-terminus is one predicted by cleavage of about 20 amino acids from the N-terminus of the ORF precisely at the alanine-aspartate site anticipated for signal peptide removal. Despite the abundance of asparagine residues, none fit the consensus context for glycosylation. Fairly extensive regions which may possess amphipathic helix forming propensity. The latter may represent units within the protein or as peptides after processing. Using circular dichroism the synthetic peptide representing amino acids 126-143 in the human preAMP sequence (FIG. 3) is readily induced to become helical in moderate concentrations of trifluoroethanol conditions used to assess helix propensity for some bioactive peptides, including anti-microbial peptides of the magainin type (see for example Park et al., 1997).

8. Localization of AMP-18

The antisera to AMP-18 have proven to be excellent histochemical probes, reacting strongly with sections of the mouse antrum region but not with the fundus, duodenum or intestine, confirming the results of the immunoblots. The preimmune sera give negligible reactions even at much higher concentration. The AMP-18 protein appears to be concentrated in mucosal epithelial cells lining the stomach lumen, although lesser signals in cells deeper in the tissue and along the upper crypt regions suggest that cells may begin to express the protein as they migrate toward the lumenal layer. Higher magnification of the histochemical preparations indicates only a general cytoplasmic staining at this level of resolution; there are some patches of intense staining that may be the light microscope equivalent of granule-packed regions of some lumenal surface cells seen by electron microscopy (EM). The localization of AMP-18 in the antrum mucosa is therefore very different from those cells synthesizing gastrin which are deep in the mucosal layer.

9. Immunoelectron Microscope Localization of the AMP-18 Antigens in the Mouse Stomach Antrum Mucosal Cells The tissue pieces were fixed in 4% formaldehyde and processed for embedding in Unicryl. Thin sections were reacted with rabbit anti-human AMP-18 antisera (1:200); bound antibodies detected by Protein-A conjugated to 10 nm colloidal gold. The reacted sections were stained with lead citrate before viewing (20,000×). The gold particles are visible over the semi-translucent secretion granules, which appear much more translucent here than in the standard glutaraldehyde-osmium-epon procedure (11,400×) because of the requirements for immuno-reactivity. Negligible background was seen on other cytoplasmic structures.

The general structure of the protein implies a possible secretory role so a precise intracellular localization would be valuable. This requires EM immuno-cytochemical procedures. Standard embedding and staining methods reveal that, as previously reported by many others, the antrum region (e.g. Johnson and McMinn, 1970) contains mucosal epithelial cells which are very rich in secretory granules. Preliminary immuno-EM data show the immune sera used at 1:200-1:800 dilution react specifically with the secretion granules. The latter appear somewhat swollen and less electron opaque than in standard fixation conditions and the differences in density are harder to discern, but overall the cell structure is quite well-preserved for stomach tissue fixed and embedded under the less stringent conditions required to preserve immuno-reactivity. At 1:100 dilution, the preimmune sera exhibited negligible backgrounds with no preference for the secretion granules.

10. Growth Factor Activity on Epithelial Cell Cultures.

A function for AMP-18 is that it is a growth factor at least partly responsible for the maintenance of a functional mucosal epithelium in the pyloric antrum and possibly elsewhere in the stomach. Initially, stomach epithelial cell lines were not immediately available, but kidney epithelial cell systems (Kartha et al., 1992; Aithal et al., 1994; Lieske et al., 1994) were used. A fractionated antrum mucosal cell extract was used for these experiments. Using immunoblotting as a probe to follow fractionation, on lysis of the mucosal cells scraped from either pig or mouse antrum, the AMP-18 antigen was recovered in the 35S fraction on sucrose density gradients. Such high speed supernatant fractions served as the starting material for studies on cell growth. Unexpectedly, these extracts stimulated a 50% increase in confluent renal epithelial cells of monkey (BSC-1 cells), but had no effect on HeLa or WI-38 fibroblast cells. The stimulation of BSC-1 cells was at least as effective as that observed with diverse polypeptide mitogens, including EGF, IGF-I, aFGF, bFGF and vasopressin, assayed at their optimal concentrations. Comparable growth stimulation by the antrum extracts was observed when DNA synthesis was assessed by measuring [$^3$H]thymidine incorporation into acid-insoluble material. The biological activity of the antrum extracts survived heating for 5 minutes at 65° C., and dialysis using a membrane with $M_r$ cutoff of 10 kDa, which would eliminate most oligopeptides; this treatment removes 60-70% of polypeptide material, but spared AMP-18 as assayed by immunoblots. More importantly, mitogenic stimulation of BSC-1 cells by the mouse or pig antrum extract was inhibited when either of two different antisera to the human recombinant preAMP-18 (expressed in bacteria) was added to the culture medium. Preimmune sera (1:100 to 1:800) had no effect on cell growth, nor did they alter the mitogenic effect of the antrum extracts. These observations suggest that gastric mucosal cell AMP-18 functions as a potent mitogen for kidney epithelial cells, which do not normally express this protein.

To gain further evidence that the growth-promoting activity in the partially fractionated antrum extracts was mediated by the AMP-18 protein, an aliquot of the mouse extract was subjected to SDS-polyacrylamide gel electrophoresis; the method used previously to determine the N-terminal sequence of the natural protein. The gel was cut into 2-mm slices and each slice was extracted with 3% acetonitrile in phosphate-buffered saline containing 1% BSA. The extract supernatants were assayed for mitogenic activity. The results indicated that one slice containing protein in the 16-19 kDa range possessed growth-promoting activity. Significantly, this growth response was blocked by the immune but not the pre-immune sera. Taken together with the relatively low sedimentation rate of the protein, these findings provide additional evidence to support the conclusion that AMP-18 is an epithelial cell mitogen and that it functions as a monomer or possibly a homotypic dimer. It also implies that the structure of the protein is such that it can readily reacquire a native conformation after the denaturing conditions of SDS-gel electrophoresis.

To assess the interaction of the antrum growth factor activity with other cytokines, its activity was tested to determine if it was additive with EGF in epithelial cell cultures. EGF (50 ng/ml) added with untreated mouse antrum extract (10 μg/ml), or heated, dialyzed pig extract (10 μg/ml) exhibited additive stimulation of mitogenesis; up to 74% increase in cell number above the quiescent level; the greatest stimulation observed so far for any factor using the BSC-1 cell assay. An example of this additivity is shown for an AMP-peptide and EGF on AGS cells in FIG. 11. This observation suggests that AMP-18 and EGF initiate proliferation by acting on different cell surface receptors. It also implies that AMP-18 growth factor activity might normally collaborate with other autocrine and paracrine factors in the maintenance or restitution of the epithelium. In view of the results with EGF, it is likely that AMP-18 is secreted at and acts upon the apical face (i.e., stomach lumenal face) of the epithelial cell layer while other factors (for which EGF may serve as an example) act from the basal surface.

11. Bioactivity of Gastrokine (AMP-18) Related Peptides.

The activities of synthetic peptides of the present invention are unexpected. Peptides based on the ORF of the human cDNA clone peptides were synthesized in the University of Chicago Cancer Center Peptide Core Facility, which checks the sequence and mass spectra of the products. The peptides were further purified by HPLC. Five relatively large oligopeptides (of about 40 amino acids each) approximately spanning the length of the protein without including the signal peptide, were analyzed. One peptide 42 amino acids long spanning amino acids lys-78 to leu-119 of the pre-AMP sequence (peptide 58-99 of the matured form of the protein; see Table 1), including a predicted helix and glycine-proline (GP) turns, gave good mitogenic activity. This response was blocked by the specific antiserum, but not by the preimmune sera.

TABLE 1

BIOACTIVITY OF SYNTHETIC PEPTIDES BASED ON THE SEQUENCE OF PRE-GASTROKINE (PRE-AMP-18)

| Name of Peptide Sequence in | #AA | AMINO ACID SEQUENCE | | $K_{1/2}$, μM |
|---|---|---|---|---|
| Human | | | | |
| 78-119 | 42 | KKTCIVHKMKKEVMP-SIQSLDALVKEKKLQGKGPGGPPPKGL | (SEQ ID NO: 17) | 0.3 |
| 78-88 | 11 | KKTCIVHKMKK | (SEQ ID NO: 14) | Inactive |
| 87-105 | 19 | KKEVMPSIQSLDALVKEKK | (SEQ ID NO: 15) | Inactive |
| 104-117 | 14 | KKLQGKGPGGPPPK | (SEQ ID NO: 11) | 0.8 |
| 104-111 | 18 | KKLQGKGPGGPPPKGLMY | (SEQ ID NO: 18) | 1.0 |
| 97-117 | 21 | LDALVKEKKLQGKGPGGPPPK | (SEQ ID NO: 12) | 0.3 |
| 97-117** | 21 | GKPLGQPGKVPKLDGKEPLAK | (SEQ ID NO: 19) | Inactive |
| 97-121 | 25 | LDALVKEKKLQGKGPGGPPPKGLMY | (SEQ ID NO: 13) | 0.2 |
| 109-117 | 9 | KGPGGPPPK | (SEQ ID NO: 20) | 2.5 |
| 104-109 | 6 | KKLQGK | (SEQ ID NO: 21) | 7.4 |
| 110-113 | 4 | GPGG | (SEQ ID NO: 22) | Inactive |
| mouse | | | | |
| 97-119 | 23 | LDTMVKEQK..GKGPGGAPPKDLMY | (SEQ ID NO: 23) | 0.2 |

Table 1:
Analysis of mitogenic peptides derived from the human and mouse pre-gastrokine (pre-AMP-18) sequence.
A 14 amino acid mitogenic domain is in bold type.
*Peptides are identified by their position in the amino acid sequence of the pre-gastrokine (preAMP-18).
AA; number of amino acids in a peptide.
$K_{1/2}$; concentration for half-maximal growth stimulation.
Overlapping inactive peptides can inhibit the activity of the mitogenic peptides: that is, human peptides 78-88 and 87-105 block the activity of peptide 78-119, and while peptide 87-105 blocks the activity of peptide 104-117, the peptide 78-88 does not. Peptides 78-88 and 87-105 block the activity of the protein in stomach extracts.
**scrambled 12. The Growth Stimulatory Domain of Gastrokine (AMP-18).

Finding that a 42-amino acid peptide representing a central region of the novel antrum mucosal cell protein AMP-18 had mitogenic activity similar in character to that of the intact protein in pig and mouse antrum extracts (Table 1), has facilitated the characterization of the bio-active region of the molecule. A peptide including amino acids at positions 78-119, gave similar maximal stimulation of growth of the BSC-1 epithelial cell line to that given by the tissue extracts and was similarly inhibited by several different antisera raised in rabbits to the bacterially-expressed complete antrum protein. The mitogenic activity of a number of synthetic "deletion" peptides related to peptide "78-119" are summarized in Table 1. Growth activity determinations have so far been accomplished with the kidney epithelial cell line as well as several gastric and intestinal lines.

The original 42 amino acid sequence of peptide 78-119 was broken into three segments bounded by lysine (K) residues; N-terminal to C-terminal these are peptides with amino acids at positions 78-88, 87-105 and 104-117. Of these only peptide 104-117 possessed mitogenic activity giving a similar plateau of growth stimulation but requiring a higher molar concentration than the original peptide "78-119"; this is reflected in the higher $K_{1/2}$ value, which suggests that 14-amino acid peptide has 30-40% of the activity of the 42-amino acid peptide. A conclusion from this is that the smaller peptide has less binding affinity for a cell receptor, perhaps due to a lessened ability to form the correct conformation, or alternatively because of the loss of ancillary binding regions. The latter notion is supported by the observations that peptides "78-88" and "87-105" can antagonize the activity of intact 42-mer peptide 78-119; these peptides also antagonize the activity of antrum extracts further supporting the validity of synthetic peptides as a means to analyze the biological function of the novel protein. An additional aspect of the invention is that peptide 87-105, but NOT 68-88, antagonizes the activity of peptide 104-117; note that peptide 87-105 overlaps the adjacent 104-117 sequence by two residues.

Taken together these results suggest a relatively simple linear model for the growth-stimulatory region of AMP-18; viz, there is an N-terminal extended binding domain (predicted to be largely helix, the relative rigidity of which may explain the linear organization of the relevant sequences as determined in the cell growth studies), followed by a region high in glycine and proline with no predicted structure beyond the likelihood of turns. It is this latter region which contains the trigger for growth stimulation. The specificity of antagonism by peptides 78-88 and 87-105 may be based on whether they overlap or not the agonist peptides 78-119 and 104-117; for example 78-88 overlaps and inhibits 78-119, but does not overlap or inhibit 104-117. The specificity of competition by these peptides taken with the inactivity of the 78-119 scrambled peptide, strengthens a conclusion that AMP-18 interacts with specific cellular components. Further evidence that the receptor binding region extends N-terminally from peptide 104-117 is provided by the enhanced activity of peptide 97-117 which contains a seven amino acid N-terminal extension of 104-117. A peptide with a four amino acid extension in the C-terminal direction (peptide 104-121) appears to have slightly less activity to the parent 104-117, but does include a natural tyrosine, which makes possible labeling with radioactive iodine, which allows determination of the binding of AMP-related peptides to cells, initially by assessment of number of binding sites and subsequently detection of the receptor protein(s).

The peptide 97-107 was used for most tests because of its activity (equal to the 42-mer) and its relative economy (21 amino acids in length). However, a C-terminal extension to the tyr-121 gives the most active peptide thus far, perhaps because it stabilizes secondary structure. Even though this peptide does not match the nanomolar activity of EGF, for example, it is much more potent than reported for trefoil peptides (Podolsky, 1997). An estimate for the activity the intact AMP protein is ca. 1-10 nM.

13. Expression of Recombinant Protein (a) *E. coli*. Recombinant constructs are generally engineered by polymerase-chain-reactions using synthetic oligonucleotides complementary to the appropriate regions of the full-length cDNA sequences within the PT/CEBP vector and extended by convenient restriction enzyme sites to enable ready insertion into standard vector polylinkers. The initial experiments with expression of the AMP ORF in bacterial systems employed an expression vector PT/CEBP, which included an N-terminal His6-tag (SEQ ID NO: 16) (Jeon et al., 1994), intended to facilitate the purification of the expressed protein on Ni-NTA resin (Qiagen). Expression of the full-length human cDNA within this vector in the host BL21(DE3)pLyS gave good yields of insoluble protein, which after electrophoresis under denaturing conditions was suitable for use as an immunogen in rabbits to obtain specific high-titer antibodies, but which has not been useful for analysis of the protein's native structure and function. This insolubility is most probably due to the presence of an unnatural N-terminus, having a His6-tag (SEQ ID NO: 16) upstream of hydrophobic signal peptide, in the expressed protein. Engineering vectors which will express the ORF without the hydrophobic signal peptide sequence are also useful. These are constructed using bacterial expression vectors with and without N- or C-terminal His-tags. The human AMP-18 sequence lacking the 20 amino acid signal peptide and containing a His6-tag (SEQ ID NO: 16) was also expressed in bacteria.

(b) *Pichia pastoris*. Among the simple eukaryotes, the budding yeast *P. pastoris* is gaining wide popularity as an expression system of choice for production and secretion of functional recombinant proteins (Romanos et al., 1992; Cregg et al., 1993). In this system, secretion of the foreign protein may utilize either its own signal peptide or the highly compatible yeast mating-type alpha signal. This organism will correctly process and secrete and at least partially modify the AMP-18 protein. Vectors for constitutive and regulated expression of foreign genes are developed in *Pichia* (Sears et al., 1998). In addition to a poly-linker cloning site, these vectors contain either the high expression constitutive glyceraldehyde-3-phosphate dehydrogenase (GAP) or the methanol-regulated alcohol oxidase promoter (AOX1). The latter is an extremely stringent promoter yielding insignificant product in normal culture conditions while giving the highest expression of the vectors tested in the presence of methanol, amounting to as much as 30% of the cell protein. The advantage that the yeast *Pichia* has over the mammalian and insect alternatives is that it is continuously grown in protein-free media, thus simplifying the purification of the expressed protein and eliminating extraneous bioactivities originating in the serum or the host animal cells. A pIB4 construct (inducible by methanol-containing medium) contains the complete human preAMP-18 cDNA sequence.

(c) Baculovirus/Insect cells. An alternative, frequently successful, non-mammalian eukaryotic expression system is that using recombinant Baculovirus, such as *Autographa californica*, in an insect cell culture system. As with *Pichia*, a large repertoire of convenient vectors are available in this system, containing both glutathione S-transferase (GST)- and His6-tags (SEQ ID NO: 16) (Pharmingen). Transfections are carried out into *Spodoptera frugiperda* (Sf) cells; these cells can be slowly adapted to protein-free medium to favor the purification of secreted proteins. If an endogenous signal peptide does not function in these cells, secretion of foreign proteins can also be forced using vectors containing the viral gp67 secretion signal upstream of the cloning site. Recombinant proteins can be expressed at levels ranging from 0.1-50% total cell protein. Some protein modifications may be more favored in this insect cell system relative to yeast, but still may not duplicate the mammalian system. It appears that the insect expression system would be somewhat more onerous than *Pichia*, and not entirely substitute for expression in mammalian cells. The human AMP-18 sequence lacking the 20 amino acid signal peptide and containing a His6-tag (SEQ ID NO: 16) was expressed in Baculovirus.

(d) Mammalian cells. Modifications not detectable by immunoblot analysis may take place in mammalian cells that are not duplicated in cells of other eukaryotes. Although not as convenient as prokaryotic and simple eukaryotic systems, mammalian cells are now frequently used for both transient and continuous expression of foreign proteins. Several growth factors have been expressed and secreted in significant amounts using these systems.

The plasmid pcDNA3/human kidney 293 system: pcDNA3 contains a polylinker cloning site flanked by the strong constitutive cytomegalovirus (CMV) promoter and a SV40 polyA signal (Invitrogen). Laboratory experience is that 60-90% transient transfection levels can be achieved. To this end, PCR amplification of the human preAMP cDNA clone is performed with oligonucleotides that contain the initiation codon and native ribosome binding site (Kozak sequence) as well as suitable restriction enzyme linkers for correct orientation into pcDNA3. Favorable constructs were identified in the transient assay using the potent antibiotic blasticidin S and a vector containing the resistance gene, stable mammalian transfectant cell lines can be established "in less than one week" (Invitrogen). The available vectors also include the constitutive CMV promoter, a polylinker cloning site, an elective V5-epitope/His6-tag (SEQ ID NO: 16) and the SV40 poly(A) signal (PcDNA6/V5-His).

14. Expression and Analysis of Altered (Modified) Forms of AMP-18

Given an efficient expression system for the production of "wild-type" AMP-18, a series of mutant proteins, containing either deletions or substitutions may be created, which will permit analysis of the functional domains. The amphipathic helices, the conserved cystine (C) residues and the basic amino acids doublets, which may be cleavage sites, are attractive targets. Although not as simple as an enzyme assay, the mitogenesis assay is routine and replicable, and would enable "mutants" to be characterized as fast as they are constructed. Dominant negative (or positive) "mutants" will be as significant as mutations exhibiting simple loss of function, because these will imply interactions with other factors including possible cell receptors.

15. Biochemical and Immunoaffinity Fractionation of Expressed and Native Gastrokine Proteins In the case of some of the expressed forms of gastrokine AMP-18, the recombinant protein will contain peptide tags that will permit the rapid purification of soluble protein. The presence of these tags, if they do not severely interfere with the protein's normal functions, will also permit analysis of interactions with other relevant macromolecules. His6-tags (SEQ ID NO: 16) permit purification by binding the recombinant proteins to Ni-NTA resin beads (Janknecht et al., 1991; Ni-NTA resin from Qiagen). The tagged protein is bound with greater affinity than most antigen-antibody complexes and can be washed rigorously before the $N_i^{2+}$-histidine chelation complex is disrupted by excess imidazole to release the purified protein. GST-tagged recombinant proteins are purified on glutathione-agarose, washed and then eluted with reduced glutathione (Smith and Johnson, 1988). As with all the proposed expression systems, each protein preparation may be tested at the earliest possible stage for its growth factor activity.

Conventional fractionation procedures are used to achieve the desired purity, particularly in the case of the isolation of the natural protein from tissue. Pig antrum mucosa is a preferred starting point for the latter, using initial centrifugation and heat-treatment protocol, followed by a size-exclusion column: BioGel P60 is suitable, given the evidence that the 18 kDa protein exists, most probably as a monomer in the extracts. The eluant is loaded on an immunoaffinity matrix created by crosslinking anti-AMP antibodies purified on HiTrap Protein A to CNBr-activated Sepharose 4B (Pharmacia). Further modification of the immunoaffinity matrix may be helpful, either by extension of the linker to the matrix, which has proven useful in the past (Aithal et al., 1994), or by crosslinking the antibody to immobilized protein-A. Because active protein can be recovered by SDS-gel elution, active protein may also be recovered from the antigen-antibody complexes. Further fractionation could be achieved by C8 reversed-phase high-performance liquid chromatography (HPLC) column. A final step is the use of the SDS-gel elution technique with confirmation of identity by N-terminal sequencing. In all of these steps the immunodetectable AMP-18 and the growth factor activity should fractionate together.

16. AMP-18 Related Synthetic Peptides

AMP-18 may be precursor to one or several bioactive peptides. Synthetic peptides provide a convenient avenue to explore the function of a protein; peptides may mimic aspects of the function or antagonize them. If a peptide either duplicates or inhibits the protein's activity, then it suggests the identity of functional domains of the intact protein, and also provides the possibility of synthesizing specifically tagged probes to explore protein-cell interactions.

Finding that a synthetic 42 amino acid peptide, representing a middle region of the human protein, is capable of mimicking the growth factor activity of the partially fractionated antrum mucosal extracts has provided a short-cut to the analysis of AMP-18 function. This peptide (designated peptide 58-99; amino acids are at positions 58-99 of the mature protein after removal of the signal peptide) in addition to several possible protein processing sites at lysine pairs, contains one of the regions capable of extended helix formation as well as a glycine-proline loop. An added advantage of this peptide is that it contains epitopes recognized by both of the antisera disclosed herein. Some smaller peptides derived from this sequence were synthesized to focus on the bioactive regions. Initially sequences bounded by the lysine residues were studied because they may indicate distinct domains within the protein structure, by virtue of being exposed on the surface of the protein, as witnessed by the antigenicity of this region, and may be sites of cleavage in vivo to bioactive peptides. The glycine-proline region is important (see Table 1 illustrating the bioactive domains of AMP-18). Glycine-proline sequences are known to be involved in SH3 (src homology domain type 3) ligands (see Cohen et al., 1995; Nguyen et al., 1998); because SH domains are involved in protein-protein interactions that GP region of AMP-18 may be involved in the interaction of the protein with a cell surface receptor. The exact GPGGPPP (SEQ ID NO: 24) sequence found in AMP-18 has not been reported for the intracellular-acting SH3 domains, so the intriguing possibility exists that it represents a novel protein interaction domain for extracellular ligands. A 21-mer derived from amino acids at positions 97-117 of the mature sequence has activity similar to the 42-mer. This shorter peptide is useful for growth assays on various epithelial cell lines. This peptide does not express the epitope recognized by the antisera disclosed herein.

All of the AMP-18 derived peptides were synthesized by the Cancer Center Peptide Core Facility of the University of Chicago, which also confirmed the molecular mass and amino acid sequence of the purified peptides that are isolated by HPLC. The biological activity of peptide 78-119 not only provides the basis for seeking smaller peptides with mitogenic activity, but permits amino acid substitutions that have positive or negative effects to be found rapidly. Inactive peptides were tested for their ability to block the function of active peptides or intact AMP-18. The possible inclusion of D-amino acids in the peptides (in normal or reverse order) may stabilize them to degradation while permitting retention of biological function. Further the ability to synthesize active peptides enables tags that facilitate studies of the nature, tissue distribution and number of cellular receptors. Such tags include His-6 biotin or iodinated tyrosine residues appended to the peptide sequence (several of the bioactive peptides have a naturally occurring tyrosine at the C-terminus).

Synthetic peptides also permit assessment of the role of potential secondary structure on function. The finding that a 4 amino acid C-terminal extension of the active peptide 97-117, predicted to promote a helix similar to that for the intact AMP-18 sequence, led to a more active peptide 97-121, is interesting. The helix-propensity of these active peptides e.g. peptide 126-143, which resembles an anti-microbial magainin peptide, provides useful information. With respect to anti-microbial peptides, the function of the magain in class is related to their ability to form amphipathic helices (Boman, 1995). Synthetic peptides that can be locked in the helical form by lactam bridges (Houston et al., 1996) enhanced biological activity; at least one pair of appropriate acidic and basic amino acid residues for lactam formation already exist in potential helix regions of AMP-18.

Another equally significant aspect of the peptide studies is the potential availability of specific anti-AMP-18 peptides that antagonize its biological functions. Tissue culture studies show that sub-peptides of the growth-promoting peptide 78-119 can antagonize the activity of the intact peptide (see Table 1). Peptides that can occupy cellular binding sites but lack some essential residues for activity may block the action of AMP-18 and its active peptides. This makes available another set of reagents for the analysis of cellular receptors and for assessing receptor-ligand affinity constants. Availability of defined peptide antagonists is useful in whole animal studies, and may eventually serve to regulate the activity of the natural protein in humans.

17. Interactions of AMP-18 and Related Peptides with Cells: Assessment of Cell Growth Non-transformed monkey kidney epithelial cell line BSC-1 and other epithelial cell lines were used to assess effects on growth. In general, conditions were chosen for each line such that cells are grown to confluence in plastic dishes in supplemented growth medium with minimal calf (or fetal) serum for growth (Lieske et al., 1997); BSC-1 cells become confluent at $10^6$/60 mm dish with 1% calf serum. At the start of the growth assay the medium on the confluent culture was aspirated and replaced with fresh medium with minimal serum to maintain viability (0.01% for BSC-1) cells. AMP-18 preparations were added to the culture medium and 4 days later the cell monolayer was rinsed, detached with trypsin, and the cells were counted using a hemocytometer. Determination of the capacity of AMP-18 to initiate DNA synthesis was measured by the incorporation of [$^3$H]thymidine (Toback, 1980); to confirm the DNA synthesis assay, autoradiograms of leveled cells were counted (Kartha and Toback, 1985).

The protein AMP-18 is expressed in the antrum mucosa and to a lesser extent in the adjacent corpus mucosa. However, both antrum extracts and the active synthetic peptides stimulate proliferation of most simple epithelial cell lines. The major criterion used, apart from cells which might be natural targets for AMP-18 or its peptides, was that of growth control, particularly cell-density restriction. Many transformed stomach lines derived from human cancer patients are available from various sources, but most of these do not exhibit growth control. For example, a gastric AGS adenocarcinoma cell subline from Dr. Duane Smoot (Howard University College of Medicine) showed a greater degree of contact inhibition, and responded well to AMP-18 and its derived peptides. These cells do not naturally synthesize AMP-18. Similar responses were observed with the non-transformed rat IEC intestinal epithelial cells (provided by Dr. Mark Musch, Dept. Medicine, University of Chicago); the latter show excellent epithelial cell characteristics in culture (Quaroni et al., 1979; Digass et al., 1998).

18. Receptors for AMP-18 on the Surface of Epithelial Cells

Characterization of the target cell receptors of AMP-18 is intriguing because of the apparent existence of receptors on cells which are not expected ever to contact this protein. Initial growth response assays were performed on kidney-derived epithelial cell lines, which responded well to the stomach factor. Gastric cell lines, as well as the non-transformed rat intestinal epithelial IEC-6 cells, were used to address the receptors in cells that are likely the true physiological targets for the antrum factor. The specificity for the action of this protein in vivo likely arises from the extremely tissue specific nature of its expression, rather than that of its receptor. It is possible that AMP-18 may interact with receptors shared with other growth factors. However, the additive growth stimulus of EGF and the antrum extracts suggest that AMP-18 may have novel receptors.

Protein molecules in cell membranes that interact with AMP-18 may be sought in several different ways. Pure AMP-18 or related peptides labeled, e.g. with biotin or radioactive iodine, are used to estimate the number of saturable sites on the cell surface. Scatchard analysis of the binding values as used to determine the number and affinity of receptors. For quantitative studies, binding is measured at increasing AMP ligand concentrations, and non-specific components are identified by measuring binding in the presence of excess unlabeled factor. Iodinated growth factors have been cross-linked to cellular receptors enabling their identification (Segarini et al., 1987). Labeled AMP ligands are incubated with cells, and the bound ligand is cross-linked to the receptors by disuccinimidyl suberate. The labeled proteins are resolved by SDS-PAGE, and autodiography is used to visualize the cross-linked complex permitting an estimate of the MW of the receptor(s). Synthetic peptide mimics or antagonists permit studies of the cellular receptors, and their properties are reasonably inferred prior to future definitive identification, presumably by cloning techniques.

In addition to crosslinking studies, antibodies, or his6-tagged (SEQ ID NO: 16) AMP-18 or peptides are used to isolate cellular or mucus proteins which bind to AMP-18. As an additional approach, an immobilized AMP-18 affinity matrix can be created by using CNMBr-activated Sepharose. As a simple beginning to the analysis of the signal transduction pathway mediated by any cell receptor, a test to assay protein tyrosine kinase activity in affinity isolates is available (Yarden and Ullrich, 1988; Schlessinger and Ullrich, 1992).

19. Is AMP-18 Processed to Bioactive Peptides?

The functional molecular form(s) of AMP-18 is not known. Certainly, the ca. 18 kDa is the protein form which accumulates in antrum mucosal cells, and substantial amounts of polypeptides of lower MW are not detected with the antisera, even though they do react with pepsin fragments down to ca. 10 kDa and also with the bioactive peptide 78-119 (having only 42 amino acids). Having access to labeled or tagged AMP-18 enables a question of whether the protein is processed in antrum mucosal extracts, or by the epithelial cells which respond to it, to be explored.

20. Genes for AMP-18 in Man and Mouse

Using PCR techniques employing primers based on the sequence of the human cDNA clone, genomic clones of human and mouse preAMP-18 were obtained. The exon/intron structure (FIG. 13) is complete. Mouse AMP exons are sufficiently similar to those of human and pig to allow a sequence of the mouse gene to be assembled. Human and mouse genes have very similar structures, the mouse gene being slightly smaller. The ORF contained in exons of the mouse gene predicts a protein having 65% identity to the human and pig proteins. A 2 kb of sequence is upstream of the human gene.

21. Knockout of the AMP-18 Gene in Mouse

From the mouse map a targeting construct is designed. The construct preferably contains: [5'-TK (a functional thymidine kinase gene)—ca. 5 kb of the 5' end of AMP-18 DNA—the neomycin phosph-transferase (neo) gene under the control of the phosphoglycerate kinase (PGK) promoter-ca. 3 kb of the 3' end of the gene-3']. A considerable length of homology of the construct with the resident AMP-18 gene is required for efficient targeting. Increasing the total homology from 1.7 to 6.8 kb increases the efficiency of homologous targeting into the hrpt gene about 200-fold (Hasty et al., 1991). Beyond that total length, the efficiency increases only slightly. To facilitate the detection of homologous intergrants by a PCR reaction, it is useful to have the neo gene close to one end of the vector. The resulting transfectants can be provided by PCR with two primers, one in the neo gene and the other in the AMP-18 locus just outside of the targeting vector. Flanks extending 4 kb 5' and 4.5 kb 3' of the mouse gene have been obtained. Through homologous recombination, the coding region will be replaced by the neo gene to ensure a complete knockout of the gene are already cloned. After trimming off the plasmid sequence, the targeting cassette will be transfected into ES cells and stable transfectants obtained by selection with G418, an analog of neomycin, and gancyclovir (Mansour et al., 1988). Southern blots with the probe from the flanking sequence will be used to screen for targeted homologous recombinants. Correctly targeted ES cell clones will be injected in blastocysts from C57BL/6 mice.

Male offspring obtained from surrogate mothers that have at least 50% agouti coat (embryonic stem cell (ES) cell derived) are bred with C57BL/6 mice. F1 mice that are agouti have the paternal component derived from the ES cells (agouti is dominant over black). 50% of these mice should have the knockout preAMP-18 allele. These hemizygous mice are monitored for any effect of diminished gene dosage. Homozygous knockouts are preferable. If the sole function of AMP-18 is in the stomach following birth, then viable homozygotes are expected. If these cannot be obtained, a fetally lethal defect would be indicated, and the fetal stage of abortion would be ascertained. This result would suggest an unanticipated role of the protein in normal development.

Homozygous AMP-18 knockout mice are useful for investigations of stomach morphology and function. It is expected that such knockouts will show if AMP-18 is essential, and at which stage of gastro-intestinal development it is bioactive. It is possible that the AMP-18 knockout hemizygous mice will already show a phenotype. This could occur if reduced dosage of the protein reduces or eliminates its function, or if parental imprinting or random mono-allelic expression has a significant influence. A range of possible outcomes of the AMP-18 knockout in mice include: i) no viable homozygotes, implying an essential unanticipated developmental role; ii) viable homozygotes, but with obviously impaired gastrointestinal functions; iii) no strong phenotype, i.e. the protein is not important to the development and life of the laboratory mouse. If appropriate, the generation of AMP-18 in overexpressing mice is pursued. A truncated AMP-18 protein produced in the mice could potentially create a dominant negative phenotype; knowledge gained from the experiments will further define the functional domains of the protein.

| Abbreviations for amino acids | | |
|---|---|---|
| Amino acid | Three-letter abbreviation | One-letter symbol |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

DOCUMENTS CITED

Aithal, N. H., et al. (1994) Am. J. Physiol. 266:F612-619.
Altschul, S., (1997) et al. (1994) Nuc. Acids Res. 25:3389-3402.
Baczako, K, et al. (1995) J. Pathol. 176:77-86.
Blaser, M. J. et al. (1987) Gastroenterol. 93:371-383
Boman, H. G. (1995) Ann. Rev. Immunol. 13:61-92.
Cohen, G. B., et al. (1995) Cell 80:237-248.
Cregg, J. M., et al. (1993) Bio/Technol. 11:905-910.
Dignass, A. U., et al. (1998) Eur. J. clin. Invest. 28:554-561
Falk, P., et al. (1993) Proc. Nat. Acad. Sci. 90:2035-2039.
Goodwin, C. S., et al., (1986) J. Clin. Microbiol. 39:353-356
Hasty, P., et al. (1991) Mol. Cell. Biol. 11:5586-5591.
Houston, M. E., et al. (1996) Biochem. 35:10041-10050.
Janknecht, R., et al. (1991) Proc. Nat. Acad. Sci. USA 88:8972-8976
Jeon, C. J., et al. (1994) Proc. Nat. Acad. Sci. USA 91:9106-9110
Johnson, F. R. and McMinn, R. M. H. (1970) J. Anat. 107: 67-86.
Kartha, S. and Toback, F. G. (1985) Am. J. Physiol. 249: F967-F972
Kartha, S., et al. (1992) Exp. Cell Res. 200:219-226.
Lieske, J. C., et al. (1994) Proc. Natl. Acad. Sci. 91:6987-6991.
Lieske, J. C., et al. (1997) Am. J. Physiol. F224-F233.
Lacy, E. R. (1998) J. Clin. Gastroenterol. 10(Suppl 1):72-77.
Mansour, S., et al. (1988) Nature 336:348.
Moore, K. S., et al. (1991) J. Biol. Chem. 266:19851-19857.
Nguyen, J. T., et al. (1998) Science 282:2088-2092.
Nomura, A., et al. (1991) N. engl. J. Med. 325-1132-1136.
Nusrat, A., et al. (1992) J. Clin. Invest. 89:1501-1511.
Park, C. B., et al. (1997) FEBS Lett. 411:173-178.
Parsonnet, J., et al. (1991) N. Engl. J. Med. 325:1127-1131.
Podolsky, D. K. (1997) J. Gastroenterol. 32:122-126.
Powell, C. J., (1987) Ph.D. Dissertation, University of Chicago.
Quaroni, A., et al. (1979) J. Cell Biol. 80:248-265.
Romanos, M. A., et al. (1992) Yeast 8:423-488.
Rotimi, V. O., et al. (1990) Afr. J. Med. med. Sci. 19:275-280.
Sands, B. E. and Podolsky, D. K. (1996) Ann. Rev. Physiol. 58:253.
Schlessinger, J. and Ullrich, A. (1992) Neuron 9:383-391.
Sears, I. B., et al. (1998) Yeast 14.
Segarini, P. R., et al. (1987) J. Biol. Chem. 262:14655-14662.
Smith, D. B. and Johnson, K. S. (1988) Gene 67:31-40.
Toback, F. G. (1980) Proc. Nat. Acad. Sci. 77:6654-6656.
Yarden et al. and Ullrich (1988) Biochemistry 27:3113-3119.
Yoo, O. J. et al. (1982) PNAS 79:1049-1053.
Yoshikawa, Y., et al. (2000) Jap. J, Cancer Res. 91:459-463.

We claim:

1. A pharmaceutical composition comprising a therapeutically effective amount of a growth promoting peptide comprising the mitogenic amino acid sequence, VKE(K/Q)KLQGKGPGG(P/A)PPK (SEQ ID NO: 25) wherein there is a Q at position 4 and a P at position 14.

2. A pharmaceutical composition comprising a therapeutically effective amount of a growth promoting peptide consisting of a mitogenic amino acid sequence, selected from the group consisting of KKLQGKGPGGPPPK (SEQ ID NO: 11), LDALVKEKKLQGKGPGGPPPK (SEQ ID NO: 12), and LDALVKEKKLQGKGPGGPPPKGLMY (SEQ ID NO: 13).

3. A pharmaceutical composition comprising a therapeutically effective amount of a growth promoting peptide comprising the mitogenic amino acid sequence VKE(K/Q)KGKGPGG(P/A)PPK (SEQ ID NO: 26).

4. A pharmaceutical composition comprising a therapeutically effective amount of a growth promoting peptide consisting of the mitogenic amino acid sequence KKTCIVHKMKKEVMPSIQSLDALVKEKKLQGKGPGGPPPKGL (SEQ ID NO:17).

5. A pharmaceutical composition comprising a therapeutically effective amount of a growth promoting peptide comprising the mitogenic amino acid sequence VKE(K/Q)KLQGKGPGG(P/A)PPK (SEQ ID NO: 25) wherein there is a Q at position 4 and an A at position 14.

6. A pharmaceutical composition comprising a therapeutically effective amount of a growth promoting peptide comprising the mitogenic amino acid sequence VKE(K/Q)KLQGKGPGG(P/A)PPK (SEQ ID NO: 25) wherein there is a K at position 4 and an A at position 14.

* * * * *

SEQUENCE LISTING

<160> NUMBER OF SEQ ID NOS: 26

<210> SEQ ID NO 1
<211> LENGTH: 7995
<212> TYPE: DNA
<213> ORGANISM: Homo sapiens

<400> SEQUENCE: 1

```
agctttataa ccatgtgatc ccatcttatg gtttcaatcc atgcacagga ggaaaattgt     60
gggcacgaag tttccaaagg gaaaatttat agattggtag ttaatgaaat acagttttcc    120
tccttggcaa atttaattta ctagcttcac tgtataggaa aaagcaggaa aaaaattaaa    180
accaactcac ctccaaacct gttttgagct tttacttgtc tgcccaattg atagtttcta    240
ctctctgctt ttgatgaaaa tattttttat tattttaatg taacttctga aaactaaatt    300
atctagaagc aaataaaaag atattgcttt tatagttccc agaaggaaaa aacaaacact    360
aggaaagttc tatctatcag atgggggaga tgtgatggag gcagtgatat ttgagctgag    420
ccttgaacaa tgaacaggag tctaccaagc gagaggctag cgggtggccc tcaagataaa    480
acaacagcat gtacaaaggc atggagacat acacatcttg actcttccag gaatggtggg    540
aacgctggtg gagctagaat gtaggtacat agcataaagt ggcagacggg aagcctttgg    600
aaatcttatt acataggacc ctggatgcca ttccaatgac tttgaatttt ctgtaggctg    660
ccagcgaaat ttccaagcgt gatagagtca tgtctatcta tgcacttcag aaagacaacc    720
tcagggttaa tgaagaaaat gcattggaat ataagaaact ggtgaccaga gtgatcaatt    780
gcatgactgt tgtgaaagtc caggtgaggg gagctgtggg caaggtcaga gttgagaggc    840
atttcagaga taaaatgaca gtaactaagt agatgtcagg ctgagaagaa agggctgtac    900
cagatatatg gtgctatcat taagtgagct caacattgca gaaaaggggt aggtttggtg    960
ggagttgctc acaaaacatg tttagtctaa gcaaaaccat tgccatgggc tcagataaaa   1020
gttaagaagt ggaaaccatt cctacattcc tataggagct gctatctgga aggcctagta   1080
tacacgtggc ttttcagctg tgattttgtt tgattttagg gattattctt tttctgaatc   1140
tgagcaatgt tagcgtgtaa aatactcaca cccacagctt tgactgggtg agaagttatc   1200
ataaatcata ttgagtttgt tgtgatacct tcagcttcaa caagtgatga gtcaggtcaa   1260
ctccatgtga aagttccttg ctaagcatgc agatattctg aaaggtttcc tggtacactg   1320
gctcatggca cagataggag aaattgagga aggtaagtct tgaccccac ctgataacac    1380
ctagtttgag tcaacctggt taagtacaaa tatgagaagg cttctcattc aggtccatgc   1440
ttgcctactc ctctgtccac tgctttcgtg aagacaagat gaagttcaca gtgagtagat   1500
ttttcctttt gaatttacca ccaaatgatt ggagactgtc aatattctga gatttaggag   1560
gtttgcttct tatggcccca tcatggaaag tttgttttaa aaaaattctc tcttcaaaca   1620
catggacaca gagaggggaa caacacacac caggtcctgt tgggggtgg agagtgaggg    1680
gagggaactt agaggacagg tcaataggg cagcaaacca ccatggcaca catataccta    1740
tgtaacaaac ctgcacgttc tgcacatgta tcccttttt ttagaagaag aaataatgaa    1800
aaaaaacctt ttttctattt atataatcat ggcatttata agcatctcta tagagaagga   1860
taattgtgct gagattagac agctgtctga gcacctcaca ctgacctatt tttaacaaaa   1920
tgactttcca catcacctga tttcggctcc atgcrgggta agcagttcct aagcccctaga  1980
aagtgccgat catccctcat tcttgaattc ctcctttat ttaccaaaat tcctgagcat    2040
```

```
gttcaggaaa gatgaaaagc ttattatcaa aataagtggc tgagatagac ttcttgtcac   2100
atttgttaca gtaaaatggg tctccaagaa agaaagattt gccttgggct ctagcatggc   2160
catttattta agaaagcatc tgaaacatga agctaccaca gcatctctcc tgtggttcca   2220
gacggaagcc tgagagtcta ggaggaggtg gaccgagaaa ccctgccaaa gtaactagta   2280
gtgccgggtt tctcacaaca cgatgcaaag gggctagaat cagatgacta ttttcatgtt   2340
tcaacatact acacactgga aaacgttacg gcagactcta ctttataatg gggctgcaaa   2400
tgtaaaatga ctactagaac taggtcctct taatagcagc aaagtttaaa agggtcagag   2460
ggagctccag acacaggtta gatttgattt ctctcctagt tctgctgtga acaagaggta   2520
taagtttggc caactcactt aaccctgaa gctcagttac cttatctgta aaatgattgc   2580
attgtactag gtgttctcta aaatttcttc tacctctgac ttttttaggag actaattttt   2640 aactccttt taagctattg ggagaaaat ttaatttttt ttcaaaagtt accttgaatc   2700
tctagagcag ttctcaaaac tattttgtcc caggcaaagg aaatgagact aggtacccag   2760
aatgaggcac cctgcataaa gctctgtgct ctgaaaacca atgtcaggga ccctgtgata   2820
aataattaaa ccaagtatcc tgggacactg ctagtgacat cgcctctgct gatcactctt   2880
gccagcgaga cactctatac ttgctttctc atcattggca tccaaactgc ctactaatcc   2940
attgctttgg aaagttttt ttaataaaaa gattatttct attaggagga aaacatccca   3000
tgttaaatag gaaaattaac tgaaatcatt tcagatgtg atttttagca cttatagcca   3060
tttcaaacca tggtattcat ttatactatg ctatttattg taaaacttct ttttttttcc   3120
aaggaaaata agatagtttg ctttatttta aaacagtaac tttcttatat tggggcactg   3180
accaaaattc aatactggta caaatatgtt acctagggg tcaaaatatg tgccaggtga   3240
attttctgaa tttctctaaa gagagaattt taaaccttat aaaacaatta gaaacaagtg   3300
agtgagaggt gagcatcaac aacctgtgta acataagcca cagtacaaat ttaagctgaa   3360
taaccaagcc atgtcagtta tcccaaatca tttttgttaa tatttaggag gatacacata   3420
ttttcaataa cttaaaagtg aatcttact cctatctctt aatactcgaa gaagtataac   3480
tttcttcttt tactagattt aaataatcca atatctact caaggtagga tgctgtcatt   3540
aactatagct gagtttatcc aaaatagaaa aatcatgaag atttataaag cattttaaaa   3600
ataatcattt atagcaagtc cttgaaagct ctaaataaga aaggcagttc tctactttct   3660
aataacacct atggtttata ttacataata taattcaaca aaacagcatt ctgaccaatg   3720
ataatttata ggaaattcat ttgccaagta tatgttttat tataaagtta atattttgac   3780
caatcttaaa aattttttaaa ctctattctg acatttccag aagtattatc ttagcaagtc   3840
atctttatga taccacttat taaactgaag agaaacaaga tggtacattc tgggttttac   3900
tttaaaaggg atttgattca ataatttgat ttatcactac ttgaaaatta cattttcttc   3960
ctcagactgg atggcaatga gatgaaagca gctttcctgg ctctcaactt cccttcttca   4020 tcaattttttc cagcgtttca taaggcctac actaaaaatt ctaaaactat atatcacatt   4080
aatataatta cttataatta atcagcaatt tcacattatc gttaaaaacct ttatggttaa   4140 aaaatgcaag gtaagagaag aaaaaaacac attgaactag aactgaacac attggtaaaa   4200
ttagtgaata cttttcataa gcttggatag aggaagaaag aagacatcat tttgccatgt   4260
aacaggagac caatgttatt tgtgatttca gattgtcttt gctggacttc ttggagtctt   4320
tctagctcct gccctagcta actatgtaag tctcaccttt tcaagtttgc taccaaaatg   4380
catttgcaag gaaatgtgat attaaatcac tctcaatctc ttataaactt cagaatatca   4440
```

```
acgtcaatga tgacaacaac aatgctggaa gtgggcagca gtcagtgagt gtcaacaatg   4500
aacacaatgt ggccaatgtt gacaataaca acggatggga ctcctggaat tccatctggg   4560
attatggaaa tgtaggtagt caacgtgcaa ttttcacttt attgtttaaa aatacgactt   4620 cttttaaca aaaatgtgc atgttaacca taaagaaatt aaaaataaat tctaattaca      4680
catagcatac agttataagt aaaggtgacc attttgctca tccgattttg ttccctagag   4740
ataactactg ttaataagtg ttgcatgatc agttaaaatt caaaccaaca aacactatgt   4800
tcaagggatt gtgggtatat acaacaaata tgaacatcct tttgccttgc ctgcagatac   4860
cctcaataat gctgaaagac ttatacaaca ttactgcttc caaagcttag actatctcac   4920
tttgttttca aaggaggttt tacgaccttc taaagagatt gaaattgaca tttcacctaa   4980
aactcgggaa atgtaaatga caatattaat tggtaagaga ggaagaagaa agaaagaag    5040 gaaggaaaga aagaaagaag gaaggaagga agaaagaaaa gaaagaaaga agagagaga   5100 aagaaagaaa aagaaaaaag agagaaagag agaaggaaag aaagagagaa ggaaaggaaa   5160
agagaagcaa agaaagagag gagcaaagaa aggaacactt agcactagtt gggagaccca   5220
actctggaat tatcagctat atatttaaca aacgttatac ttttaaatag caaactcttt   5280
attgtttcaa ttttatctgg tcaattggaa aaataatttt tgtcttatct gtctccttga   5340
aatgtgagga tcaaggagaa ctaaaacatg atagctttta aagtctattt cagtaaaaca   5400
gacttatata gaggggtttt tatcatgctg gaacctggaa ataaagcaaa ccagttagat   5460
gctcagtctc tgccctcaca gaattgcagt ctgtccccac aaatgtcagc aatagatatg   5520
attgccaagc agtgccccat ccagtgctct tatcccagct catcacgatc ttggagttcc   5580
catttctctc tgcaggtgga actgacctct gataagaaaa gctcctcgga aacacatgc    5640 ctcactattt gccatctact ttaacagggc tttgctgcaa ccagactctt tcaaaagaag   5700
acatgcattg tgcacaaaat gaacaaggaa gtcatgccct ccattcaatc ccttgatgca   5760
ctggtcaagg aaaagaaggt aaaaataaaa ggcttttat ttttggtgag gggagaggtt    5820
ttacatcctt cagtaaataa cgagaagatc acagtcattc cctcttgact acagtatgtt   5880
gtagtgtgca gcacaaaggg ggaagttatt ggtgattgcc tgagggaagg caacttctgc   5940
cacatcaaat gctgtggctc acacctacct ctacaaccgc tgagcaaagc acttgaaacc   6000
ttgactgtta gaggagcaaa gctctggtca caccaatagg agcctcagta ctttgccaag   6060
gacatttttc tgcaagagtt agttagggtt attagattta gcaaatgaaa atagaagata   6120
tccagttagg tttgaatttt aggtaagcag caggtctttt tagtataata tatcctatgc   6180
aatatttggg atatactaaa aaaagatcca ttgttatctg aaattcaaat gtaactgggt   6240
attgtatatt ttgtctggcc atactaatcc aggtgagtgg aaagaagaga tccataatgt   6300
tttaaaatat ttgcctgagt tcatattcct ataactgata aatgagtacc tttcattgac   6360
aaggtagaga aaataaataa actgcattct cagaagatga ttattacata gtctaatcca   6420
aggaatctat gatgaccaaa tgaggtccaa gttgcagaat aaattaagcc tcagacttct   6480
gtgtttatga aagctgagg tttcaaacca ggtaaatccc ttaggacact tagaaatgct    6540
aagatataca gaataagcta gaaatggctc ttcttcatct tgattatgga aaaatttagc   6600
tgagcaacac tcactgttgg cctcgtatac ccctcaagtc aacaaccac tgggcttggc    6660 attcattctc tcccattctt cctttctacc tctcttttcc acactcagct tcagggtaag   6720
ggaccaggag gaccacctcc caagggcctg atgtactcag tcaacccaaa caaagtcgat   6780
gacctgagca agttcggaaa aaacattgca aacatgtgtc gtgggattcc aacatacatg   6840
```

-continued

```
gctgaggaga tgcaaggtga gtagcatccc tactgtgcac cccaagttag tgctggtggg      6900
attgtcagac tatcctcgcg cgtgtccata gtgggcacca gtgatgcagg gatggtcatc      6960
aaggccaaca tttgtgcagt gcttgctctg tgccaggtac tgttctatgt gctttaagtg      7020
tgttaactcg gttcttcaca gcaatcttat aggttctatt ttaatcctac tttatggatg      7080
aggaaactga ggtacagaga ggtcacaaaa tccttgcctg ggtcaattcc aagcattttg      7140
gctgtggatt ctgtgctctt aaatattatg gaacactgcc ttttaagtgt gaatcaagag      7200
tagactcaag tcatattcaa agaatgcat gaatggctaa atgaaagaag aatgctaata      7260
gaatctatta actttctata gctcagacaa tcacttaatt tctggacatt caagaacag      7320 ctgcacacaa acaaagtgtc tacctaggga cctaacttaa tggcaatttt ccagatctct      7380
gaattgattg atttcatcac aacaagtaga taaaccttga cattagcaca tagctagttt      7440
ggaaacccct actccccaa tcccctccaa gaaagagtc cttaaataga cattaatata      7500
ggcttcttct tttctcttta ttagaggcaa gcctgttttt ttactcagga acgtgctaca      7560
cgaccagtgt actatggatt gtggacattt ccttctgtgg agacacggtg gagaactaaa      7620 caattttta aagccactat ggatttagtc atctgaatat gctgtgcaga aaaaatatgg      7680
gctccagtgg ttttaccat gtcattctga aattttctc tactagttat gtttgatttc      7740
tttaagtttc aataaaatca tttagcattg aattcagtgt atactcacat ttcttacaat      7800
ttcttatgac ttggaatgca caggatcaaa atgcaatgt ggtggtggca agttgttgaa      7860
gtgcattaga ctcaactgct agcctatatt caagacctgt ctcctgtaaa gaacccttc      7920 aggtgcttca gacaccacta accacaaccc tgggaatggt tccaatactc tcctactcct      7980
ctgtccactg cttaa                                                       7995

<210> SEQ ID NO 2
<211> LENGTH: 752
<212> TYPE: DNA
<213> ORGANISM: Homo sapiens

<400> SEQUENCE: 2
catgcttgcc tactcctctg tccactgctt tcgtgaagac aagatgaagt tcacaattgt        60
ctttgctgga cttcttggag tctttctagc tcctgcccta gctaactata atatcaacgt       120
caatgatgac aacaacaatg ctggaagtgg gcagcagtca gtgagtgtca acaatgaaca       180
caatgtggcc aatgttgaca ataacaacgg atgggactcc tggaattcca tctgggatta       240
tggaaatggc tttgctgcaa ccagactctt tcaaaagaag acatgcattg tgcacaaaat       300
gaacaaggaa gtcatgccct ccattcaatc ccttgatgca ctggtcaagg aaaagaagct       360
tcagggtaag ggaccaggag gaccacctcc caagggcctg atgtactcag tcaacccaaa       420
caaagtcgat gacctgagca agttcggaaa aaacattgca acatgtgtc gtgggattcc       480 aacatacatg gctgaggaga tgcaagaggc aagcctgttt ttttactcag gaacgtgcta       540
cacgaccagt gtactatgga ttgtggacat ttccttctgt ggagacacgg tggagaacta       600 aacaatttt taaagccact atggatttag tcatctgaat atgctgtgca gaaaaaatat       660
gggctccagt ggttttttacc atgtcattct gaattttttc tctactagtt atgtttgatt       720
tctttaagtt tcaataaaat catttagcat tg                                    752

<210> SEQ ID NO 3
<211> LENGTH: 185
<212> TYPE: PRT
<213> ORGANISM: Homo sapiens
```

<400> SEQUENCE: 3

```
Met Lys Phe Thr Ile Val Phe Ala Gly Leu Leu Gly Val Phe Leu Ala
  1               5                  10                  15
Pro Ala Leu Ala Asn Tyr Asn Ile Asn Val Asn Asp Asp Asn Asn Asn
                 20                  25                  30
Ala Gly Ser Gly Gln Gln Ser Val Ser Val Asn Asn Glu His Asn Val
             35                  40                  45
Ala Asn Val Asp Asn Asn Asn Gly Trp Asp Ser Trp Asn Ser Ile Trp
         50                  55                  60
Asp Tyr Gly Asn Gly Phe Ala Ala Thr Arg Leu Phe Gln Lys Lys Thr
 65                  70                  75                  80
Cys Ile Val His Lys Met Asn Lys Glu Val Met Pro Ser Ile Gln Ser
                 85                  90                  95
Leu Asp Ala Leu Val Lys Glu Lys Lys Leu Gln Gly Lys Gly Pro Gly
                100                 105                 110
Gly Pro Pro Pro Lys Gly Leu Met Tyr Ser Val Asn Pro Asn Lys Val
                115                 120                 125
Asp Asp Leu Ser Lys Phe Gly Lys Asn Ile Ala Asn Met Cys Arg Gly
            130                 135                 140
Ile Pro Thr Tyr Met Ala Glu Glu Met Gln Glu Ala Ser Leu Phe Phe
145                 150                 155                 160
Tyr Ser Gly Thr Cys Tyr Thr Thr Ser Val Leu Trp Ile Val Asp Ile
                165                 170                 175
Ser Phe Cys Gly Asp Thr Val Glu Asn
                180                 185
```

<210> SEQ ID NO 4
<211> LENGTH: 7226
<212> TYPE: DNA
<213> ORGANISM: Mus sp.
<220> FEATURE:
<221> NAME/KEY: modified_base
<222> LOCATION: (7030)..(7030)
<223> OTHER INFORMATION: a, c, t, g, other or unknown
<220> FEATURE:
<221> NAME/KEY: modified_base
<222> LOCATION: (7084)..(7084)
<223> OTHER INFORMATION: a, c, t, g, other or unknown

<400> SEQUENCE: 4

```
gaattcaaac agcaggccat ctttcaccag cactatccga atctagccat accagcattc      60
tagaagagat gcaggcagtg agctaagcat cagaccectg cagccctgta agctccagac     120
catggagaag aggaaggttg tgggttcaag gagcttttca gagtggaaat ctgtggatca     180
gtgatttata aaacacagtt tccccettta ttagatttga accaccagct tcagttgtag     240
aagagaacag gttaaaaaat aataagtgtc agtcagttct ccttcaaaac tattttaaac     300
gtttacttat tttgccaagt gacagtctct gcttcctctc ctaggagaag tcttccctta     360
ttttaatata atatttgaaa gttttcatta tctagagcag tggttctcat cctgtgggcc     420
atgagccctt tgggggggtt gaacgaccct tcacagggg tcacatatca gatatcctgc      480
atcttagcta tttacattat gattcataac agtagcaaaa ttagttagga agtaggaaca     540
aaataacgtt atggttgtgg tcaccactat gttagagggt ccgcagcatt cagagggttg     600
agaactgttg ttctagaggc aaataagaag acagagttcc ttgatagggc ccagaggcag     660
tgaaagaagt ttccacgtag aaagtgaaga aggtctggtg tccgaagcag tgaggaactt     720
aaaaaaagaa aaccaaaaac attgccaact aacagtccag gagaagagcg gggcatgaaa     780
```

```
ggctgagttc ccatgggatg ccttgaatgg aatcagagtg tgggaaaatt ggtgtggctg      840
gaaggcaggt gccgggcatc tcagacgctg gtagctgggg aaacaggaaa ccccttttagg     900 atcccaagat gccattccaa tgagcttgag attttttctca tggactgcca gtgaatgttt    960
ctacgctccg gaaattaatg tttacttatt ttccatattc taggggagaa ccctgggaaa    1020
aatggaggac attcattgaa atatctgagt cctgggataa ggcaggcttg gtcctacaac    1080
tctggtaaaa gtccatcagg caaggtttag ttgctagata tgtagatggc aagatggtgc    1140
tgccaacagc ccccagagct ctaacccact gagaaaccca ggaatgaatg atgggagatg    1200
gctttggtgc cagctgctag tgacatggct ggaaagctgc actggcttcg aggccagaca    1260
attcctcaag gaaacatctg gccagggtgc aagggccagt ttccttcctt ggagttcctt    1320
tcacagctaa gaacatcatc ccccaaccac tggttttgtt aaaaagtttt cagtatgact    1380
tgagcatggt caagaagcat agagagggggg aaataagggt ggaaggagct ggagaaagct    1440
tacaatagga ctgggtaaag ggaaggagaa gaaaccattc ccgcattccc ataggagcca    1500
gtaccaggaa gggcaggtgt acacacagat ctcatctaag gccatgtttg gtttagggat    1560
tactcttctc ccgaatctga gcagcagcaa tacgtaaaat acccacaccc atggcttcca    1620
tattccagaa cttatcacaa accgtgtaga gtttactgag ataccttcgt cagaggatga    1680
gtcagaggcc tcctgcctaa gggccctact gagcaggcag ctaaaggctt ccgggcctct    1740
gcagctccac agatacagga gagggaagca gataagccgt ggactccacc tgagcacacc    1800
tagcttgagc aaagctggtc aggtacaaat agcagagggc tgaatgtctg tgagcacgcc    1860
gcctgatcct ctgctccacc acactcctgc cgccatgaag ctcacagtaa gtcagatctt    1920
cttttcaatg cagcaccata caacattaat agtcaggggt gaggggggtct gactcttacg    1980 gcactgttac catagtggaa atattctcct ttcttttcat ggaatcatgg tgtttacaag    2040
catgtccata gagaagaaga attgccccgg aagagcctgt cacaggctga atactgtaga    2100
attgtctttc acaccatctg ttccaaggtt ctacttaaga cgagcagtct ctgggctcca    2160
gaaagagtct ttcttagcct tgatctcttt cttatttctg atttctcctt tcttatccat    2220
gatttccact tttaccagtt ctgggcatcc ggtcagactg gaagatcact gttgtcaaaa    2280
ctagtcttca acactcttgg ctgttaacat gaaaacaacg gtccttgggc cctgtgcaag    2340
catttcttgg agaaagtctc tggggatgaa gctatctcag tttcccccact gaagtcctag    2400 gatacagagg ctcaaacaga gtgcacatat tcaatttcag catactctat tggcgctgct    2460
ttatgaatca tatgaattta tggaattgga aatgtaaact atgaccaaga agcgtccacc    2520
tcagaacagg ttgggtgggg aactccaagc acaggccaga gggctgcgtt tctcttctag    2580
ttctgtctag aggagtggtt ctcgaccttc ctaatgctgt gaccctttaa tacagttcct    2640
cacgttgtcg tgactcccag ccataaaatt actttcattg ctactgcata actgtaattt    2700
tgctaccatt atgagttgta atgtaaatat ctgatatgca agataccaga taacctaaga    2760
aacggttgtt tgacctttaa aggggtcaca acccacaggt ggagaactac tggtctaggg    2820
tcctttacag tcctttagct gcctcattta caggagataa catcatgctc aaaaactccc    2880
tccacatttg gctttttggg ttgttttgtt ttgtttttca agacagggtt tctctgtgta    2940
gccctggctg tcctggaact caccttgta gaccaggctg gcctcgaact cagaaatccg    3000
cctgcttctg cctcctgagc gctgggatta aaggcgtgcg ccaccatgtc tggctcacat    3060
ctggcttttt aagagaccga tttaacttc ttgcattgaa aataaatata gtagaaatgc    3120
ttaacctact aagacaataa aaacaggatt ccttctgcta ggaagaacac gttccagact    3180
```

```
aaggaaaaaa accttttcag ggctttcatt acactgtgcc atgcactaat tttatgtttt    3240
cttcatcagt tttcagtgtc tgaaattcag tgtcaaaatt ctaagactac atatgatatc    3300
attacagtaa ctcagcaatt ctatgttacc agtaagtttt tctgtagttt aaaaaaaagg    3360
tggaagaaga aagcacagat agtttagcac atgggtaaaa tcagtaacta tttctgatga    3420
gcttggtgaa gatgctgtaa accatgcgac caccagtcct gttctctgtg ctttcagatg    3480
ttcgtcgtgg gtctgcttgg cctccttgca gctcctggtt ttgcttacgt aagtctcatt    3540
tttctgaagt tcattgtcaa aactgcattt acagtgaaat gtgatcttaa gtcaccctct    3600
gcttcttatg aacattagac ggtcaacatc aatggtaatg atggcaatgt agacggaagt    3660
ggacagcatt cggtgagcat caatggtgtg cacaacgtgg ccaatatcga caacaataac    3720
ggctgggact cctggaatag cctctgggac tatgaaaacg tatgtaatgg acacacaggg    3780
taaagatatg gtgtagccac cacccattaa aatttctgag gtgaattcta gctgttcatg    3840
aacattaaaa gctaccagta aaagtgccca ttccactcaa aacaatttta cttttttgca    3900
tataattatt gctaataagt attacacaat aggtcgaaat tcaagggat caatagtaag     3960
gataaaaact atgtacaaag acaaacacag catccttttgg tcttccctgc agagagtctc    4020
catgatgtta aaggtccaat gttttatgga ggctgaatga aatacgaatg cctctgtgat    4080
ggaaaaggcc caacatctta tggagaatga gtgaagtatg aatgctatta gttgtaagag    4140
aaggcgatgc aaagcaacac ttggcaccac ctgccaatta ctactttcct atttaaatgt    4200
agtttaaaaa gcaaagcctg tcttccctgc ctcctggaaa cactgcggat ggaggtagac    4260
caaggtatga cagcctttaa aagtttgtca gcaaaacact cccccataca cacatacaca    4320
cacccctccta ctacactgga actgaagcaa aggcagtggg ttagatatat ccaccctcta    4380
agagtttgca ggtcatctat atatgatagc cagagacaca actgcaggac agccagactc    4440
tgagcactct ccccagctcc ttgtagctct gtttcagtgg tgacttgtga caagaatcct    4500
ggggaacctg tgcctcactg ttctctgtct tctttaatag agtttcgctg ccacgagact    4560
cttctccaag aagtcatgca ttgtgcacag aatgaacaag gatgccatgc cctcccttca    4620
ggacctcgat acaatggtca aggaacagaa ggtaaagtcc tgccttcttc tttggagtga    4680
caggaagtct tacagtctcc agtacacagt gaagtcaccc ccattccctc tttggtggag    4740
catgacagca tgtttgtcat gataaatgcc acaaacatgt aaaactgttc agtgtctgcc    4800
tgaatggagg gtggcttcca ctgtgtcaga tgccgtggcc cacatctgcc tctgcagggt    4860
ccagtaaagc actggctatc ttgagtgtca gagacccaaa ggtctgtaca cttcagtaca    4920
agccctccat atttcaaggg cacactccta cagtcgttgg ggttatcaga actagcaaac    4980
atagagactg gattttcaga tgaaagaaa tccttttttaa agtctaagta tgccttatac    5040
aatgtttgag atattctcaa tactaaaaaa aaaaaaattg ttgcttgctt gaaaatcaaa    5100
tgtaaccaag tgtcctatat ccagtgtcaa tcatggctgt agtagatggg aagagggagc    5160
ccgtggtttt cacagtcaga cgcctgagtt attcttctaa gtgataaatt ggttcctata    5220
acaagcaagc cagtgaatat aaataagctc tatctcagaa gttatcctgt agtgctaccc    5280
tagaatctaa gagagcaaaa gtgcttcaaa tttcagaata gttttgcttt tggacttctg    5340
tttttctaaa caactataac ttcaaaccat ctaagcctcg tgggacactt agaaatacca    5400
agccattcaa agctagaatt gtttcttcac cttacttgaa aacaaaatga caaccaaaaa    5460
ttgtccccac tgcccttgta catcttcaga tcagtaaagt cctgggctca gggatcattc    5520
actttctttc tttcctttca cactcaactt cagggtaaag ggcctggagg agctcctccc    5580
```

-continued

```
aaggacttga tgtactccgt caaccctacc agagtggagg acctgaatac attcggacca    5640
aagattgctg gcatgtgcag gggcatccct acctatgtgg ccgaggagat tccaggtgtg    5700
taccctgaga tgctgtatat cccaatgcag tactgagaga ccatcagac actctaaagt     5760 gtgaccacag acggaccaat catgtggatt atcagagcaa acacttgctt gctccttgtc    5820
agacagttgt ccatgcttca aaagttcatt aaaaaaaata gttcacaggc tcctcacaga    5880
aaccttagta gaatccacag cttctgctct tagtcttact tttagaaaac tgagacccag    5940
agaaaggtca caaaactttt gtctggctca ggttctatgt cttaactttt atagaatacc    6000
gtctttctgg gtgggtgggc tctagagtaa acttcaagtg agttcaagga aagcatgaga    6060
agtagggaag accaaatgaa aggagaatgc caatgaaatc tatcgattct atagcgccaa    6120
tgcttaactc ctaggcgttc aaagaatagt atccacaagg tgtcagccta agatcctaat    6180
ctaacagcaa gttttcagat tctgaagtg aaaagagaaa gcaagagagg aacagagaca     6240
gaaacagtaa gagacagaga ggcagagaca aagagacagg gagaatagag agggattaaa    6300
attaatatat agtttagaaa ttacgactcc tcacagtccc tgcagagtcc taggataggc    6360
actgatttgg acttctttc ttctcactag gaccaaacca gcctttgtac tcaaagaagt      6420
gctacacagc tgacatactc tggattctgc ggatgtcctt ctgtggaaca tcagtggaga    6480
catactagaa gtcacaggaa acaacccgt gggctctgac catcgcaatg cttgattatg      6540
agagtgttct ctgggggttg tgattagctt ctttaaggct caataaaccc acgtggcagc    6600
acatccagtt tgtaatgaca tgcctcatga cttctatggg agtccaatgt ggcacctgcc    6660
agcctgtatt caggacctct ccgctataaa gcatccctcc agagttttca aatactacaa    6720
agcacagcct gggtttgggc tcagataggc cactgctgcc tgactacatt acagacaaac    6780 aagtttaaa agaaagaaaa aagagctcag agtggctgga atcagcaagg gtgttttcc       6840 tgcaaggagc cagaagtatc aataatcacc caaggaggag acactgggaa tgagagacta    6900
gaacacacgc ctgcagatac ggagaacctc agcattgccg ctctctccca taactgcaca    6960 ccccttctg taaactctgc ttctttcttt cacctgaaga tggcccttgc tttttttat      7020 tataggacan gataactaga ccagaaagtc aacctgactc tctacattta tatgtcttcc    7080
cagntcaaga aatattattt actggtgaat ggcacttcta tattcccttg gttcaataag    7140
tctacaggat ccattcattg acaggccaag agtgagatca catgataccc aagcacatgg    7200
gtctttcctt gaaggagaag gatcca                                         7226
```

<210> SEQ ID NO 5
<211> LENGTH: 543
<212> TYPE: DNA
<213> ORGANISM: Mus sp.

<400> SEQUENCE: 5

```
atgttcgtcg tgggtctgct tggcctcctt gcagctcctg gttttgctta cacggtcaac     60
atcaatggta atgatggcaa tgtagacgga agtggacagc attcggtgag catcaatggt    120
gtgcacaacg tggccaatat cgacaacaat aacggctggg actcctggaa tagcctctgg    180
gactatgaaa acagtttcgc tgccacgaga ctcttctcca agaagtcatg cattgtgcac    240
agaatgaaca aggatgccat gccctccctt caggacctcg atacaatggt caaggaacag    300
aagggtaaag ggcctggagg agctcctccc aaggacttga tgtactccgt caaccctacc    360
agagtggagg acctgaatac attcggacca aagattgctg gcatgtgcag gggcatccct    420
acctatgtgg ccgaggagat tccaggacca aaccagcctt tgtactcaaa gaagtgctac    480
```

```
acagctgaca tactctggat tctgcggatg tccttttgtg aacatcagt ggagacatac      540 tag                                                                   543

<210> SEQ ID NO 6
<211> LENGTH: 184
<212> TYPE: PRT
<213> ORGANISM: Mus sp.

<400> SEQUENCE: 6

Met Lys Leu Thr Met Phe Val Val Gly Leu Gly Leu Leu Ala Ala
 1               5                  10                  15

Pro Gly Phe Ala Tyr Thr Val Asn Ile Asn Gly Asn Asp Gly Asn Val
                20                  25                  30

Asp Gly Ser Gly Gln Gln Ser Val Ser Ile Asn Gly Val His Asn Val
            35                  40                  45

Ala Asn Ile Asp Asn Asn Asn Gly Trp Asp Ser Trp Asn Ser Leu Trp
        50                  55                  60

Asp Tyr Glu Asn Ser Phe Ala Ala Thr Arg Leu Phe Ser Lys Lys Ser
 65                 70                  75                  80

Cys Ile Val His Arg Met Asn Lys Asp Ala Met Pro Ser Leu Gln Asp
                85                  90                  95

Leu Asp Thr Met Val Lys Glu Gln Lys Gly Lys Gly Pro Gly Gly Ala
            100                 105                 110

Pro Pro Lys Asp Leu Met Tyr Ser Val Asn Pro Thr Arg Val Glu Asp
        115                 120                 125

Leu Asn Thr Phe Gly Pro Lys Ile Ala Gly Met Cys Arg Gly Ile Pro
    130                 135                 140

Thr Tyr Val Ala Glu Glu Ile Pro Gly Pro Asn Gln Pro Leu Tyr Ser
145                 150                 155                 160

Lys Lys Cys Tyr Thr Ala Asp Ile Leu Trp Ile Leu Arg Met Ser Phe
                165                 170                 175

Cys Gly Thr Ser Val Glu Thr Tyr
            180

<210> SEQ ID NO 7
<211> LENGTH: 597
<212> TYPE: DNA
<213> ORGANISM: Sus scrofa

<400> SEQUENCE: 7
atgcctgact ctcacttca ttgcattggt gaagccaaga tgaagttcac aattgccttt       60
gctggacttc ttggtgtctt cctgactcct gcccttgctg actatagtat cagtgtcaac      120
gacgacggca acagtggtgg aagtgggcag cagtcagtga gtgtcaacaa tgaacacaac      180
gtggccaacg ttgacaataa caatggatgg aactcctgga atgccctctg ggactataga      240
actggctttg ctgtaaccag actcttcgag aagaagtcat gcattgtgca aaaatgaag      300 aaggaagcca tgccctccct tcaagccctt gatgcgctgg tcaaggaaaa gaagcttcag      360
ggtaagggcc caggggggacc acctcccaag agcctgaggt actcagtcaa ccccaacaga      420
gtcgacaacc tggacaagtt tggaaaatcc atcgttgcca tgtgcaaggg gattccaaca      480
tacatggctg aagagattca aggagcaaac ctgatttcgt actcagaaaa gtgcatcagt      540
gccaatatac tctggattct taacattttcc ttctgtggag aatagcgga gaactaa        597

<210> SEQ ID NO 8
<211> LENGTH: 185
<212> TYPE: PRT
```

-continued

```
<213> ORGANISM: Sus scrofa

<400> SEQUENCE: 8

Met Lys Phe Thr Ile Ala Phe Ala Gly Leu Leu Gly Val Phe Leu Thr
 1               5                  10                  15

Pro Ala Leu Ala Asp Tyr Ser Ile Ser Val Asn Asp Asp Gly Asn Ser
            20                  25                  30

Gly Gly Ser Gly Gln Gln Ser Val Ser Val Asn Asn Glu His Asn Val
        35                  40                  45

Ala Asn Val Asp Asn Asn Asn Gly Trp Asn Ser Trp Asn Ala Leu Trp
    50                  55                  60

Asp Tyr Arg Thr Gly Phe Ala Val Thr Arg Leu Phe Glu Lys Lys Ser
65                  70                  75                  80

Cys Ile Val His Lys Met Lys Lys Glu Ala Met Pro Ser Leu Gln Ala
                85                  90                  95

Leu Asp Ala Leu Val Lys Glu Lys Lys Leu Gln Gly Lys Gly Pro Gly
            100                 105                 110

Gly Pro Pro Pro Lys Ser Leu Arg Tyr Ser Val Asn Pro Asn Arg Val
        115                 120                 125

Asp Asn Leu Asp Lys Phe Gly Lys Ser Ile Val Ala Met Cys Lys Gly
    130                 135                 140

Ile Pro Thr Tyr Met Ala Glu Glu Ile Gln Gly Ala Asn Leu Ile Ser
145                 150                 155                 160

Tyr Ser Glu Lys Cys Ile Ser Ala Asn Ile Leu Trp Ile Leu Asn Ile
                165                 170                 175

Ser Phe Cys Gly Gly Ile Ala Glu Asn
            180                 185

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met Arg Gly Ser His His His His His His Gly Ser
 1               5                  10

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (4)..(4)
<223> OTHER INFORMATION: Lys or Gln
<220> FEATURE:
<221> NAME/KEY: MOD_RES
<222> LOCATION: (6)..(7)
<223> OTHER INFORMATION: This region is 0 or 2 residues in length and
      encompasses "Leu Gln" or is absent
<220> FEATURE:
<221> NAME/KEY: MOD_RES
<222> LOCATION: (14)..(14)
<223> OTHER INFORMATION: Pro or Ala

<400> SEQUENCE: 10

Val Lys Glu Xaa Lys Xaa Xaa Gly Lys Gly Pro Gly Gly Xaa Pro Pro
 1               5                  10                  15
```

Lys

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Lys Leu Gln Gly Lys Gly Pro Gly Gly Pro Pro Pro Lys
 1               5                  10

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Asp Ala Leu Val Lys Glu Lys Lys Leu Gln Gly Lys Gly Pro Gly
 1               5                  10                  15

Gly Pro Pro Pro Lys
            20

<210> SEQ ID NO 13
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Asp Ala Leu Val Lys Glu Lys Lys Leu Gln Gly Lys Gly Pro Gly
 1               5                  10                  15

Gly Pro Pro Pro Lys Gly Leu Met Tyr
            20                  25

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Lys Thr Cys Ile Val His Lys Met Lys Lys
 1               5                  10

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Lys Glu Val Met Pro Ser Ile Gln Ser Leu Asp Ala Leu Val Lys
 1               5                  10                  15

Glu Lys Lys

```
<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: 6-His tag

<400> SEQUENCE: 16

His His His His His His
 1               5

<210> SEQ ID NO 17
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Lys Thr Cys Ile Val His Lys Met Lys Glu Val Met Pro Ser
 1               5                  10                  15

Ile Gln Ser Leu Asp Ala Leu Val Lys Glu Lys Lys Leu Gln Gly Lys
             20                  25                  30

Gly Pro Gly Gly Pro Pro Pro Lys Gly Leu
         35                  40

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Lys Leu Gln Gly Lys Gly Pro Gly Gly Pro Pro Pro Lys Gly Leu
 1               5                  10                  15

Met Tyr

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Lys Pro Leu Gly Gln Pro Gly Lys Val Pro Lys Leu Asp Gly Lys
 1               5                  10                  15

Glu Pro Leu Ala Lys
             20

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Gly Pro Gly Gly Pro Pro Pro Lys
 1               5
```

```
              <210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Lys Leu Gln Gly Lys
 1               5

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Pro Gly Gly
 1

<210> SEQ ID NO 23
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Asp Thr Met Val Lys Glu Gln Lys Gly Lys Gly Pro Gly Gly Ala
 1               5                  10                  15

Pro Pro Lys Asp Leu Met Tyr
            20

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence:
      Glycine-proline synthetic peptide

<400> SEQUENCE: 24

Gly Pro Gly Gly Pro Pro Pro
 1               5

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys or Gln
<220> FEATURE:
<221> NAME/KEY: MOD_RES
<222> LOCATION: (14)..(14)
<223> OTHER INFORMATION: Pro or Ala

<400> SEQUENCE: 25

Val Lys Glu Xaa Lys Leu Gln Gly Lys Gly Pro Gly Gly Xaa Pro Pro
```

Lys

```
<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys or Gln
<220> FEATURE:
<221> NAME/KEY: MOD_RES
<222> LOCATION: (12)..(12)
<223> OTHER INFORMATION: Pro or Ala

<400> SEQUENCE: 26

Val Lys Glu Xaa Lys Gly Lys Gly Pro Gly Gly Xaa Pro Pro Lys
 1               5                  10                  15
```